(12) United States Patent
Williams et al.

(10) Patent No.: US 6,291,220 B1
(45) Date of Patent: Sep. 18, 2001

(54) POLYNUCLEOTIDES ENCODING PHOSPHATIDYLINOSITOL 3-KINASES

(75) Inventors: Lewis T. Williams, Tiburon; Lisa Molz; Yen-Wen Chen, both of San Francisco, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/170,996

(22) Filed: Oct. 13, 1998

Related U.S. Application Data

(62) Division of application No. 08/609,049, filed on Feb. 12, 1996, now Pat. No. 5,948,664.

(51) Int. Cl.[7] .................................................. C12N 9/12
(52) U.S. Cl. ..................... 435/194; 435/320.1; 435/325; 435/252.3; 435/419; 435/254.11; 536/23.2
(58) Field of Search ........................ 435/15, 194, 252.3, 435/254.11, 320.1, 325; 424/94.5; 530/387.1, 387.9, 388.26; 536/23.1, 23.2, 23.4, 23.5, 24.3, 24.31

(56) References Cited

U.S. PATENT DOCUMENTS 5,948,664 * 9/1999 Williams et al. .................... 435/194

FOREIGN PATENT DOCUMENTS

WO 9321328   10/1993  (WO) .

OTHER PUBLICATIONS

Auger, K. R., et al., "PDGF–Dependent Tyrosine Phosphorylation Stimulates Production of Novel Polyphosphoinositides in Intact Copy," Cell, vol. 57, Apr. 7, 1989, pp. 167–175.
Brown, N. H., et al., "Functional cDNA Libraries from Drosophila Embryos ," J. Miol. Biol., vol. 203, 1988, pp. 425–437.
Carpenter, C. L. et al., "Purification and Characterization of Phosphoinositide 3–Kinase from Rat Liver," Journal of Biological Chemistry, vol. 265, No. 32, Nov. 15, 1990, pp. 19704–19711.
Carter, A. N., et al., "Phosphatidylinositol 3,4,5–trisphosphate is formed from phosphatidylinositol 4,5–bisphosphate in thrombin–stimulated platelets," Biochem. J., vol. 301, 1994, pp. 415–420.
Databases EST–STS and n–geneseq. Apr. 1997, relevant his.
Dhand, R., et al., "PI 3–kinase is a dual specificity enzyme: autoregulation by an intrinsic protein–serine kinase activity," EMBO Journal, vol. 13, No. 3, 1994, pp. 522–533.
Franke, T. F., et al., "The Protein Kinase Encoded by the Akt Proto–Oncogene Is a Target of the PDGF–Activated Phosphatidylinositol 3–Kinase," Cell, vol. 81, Jun. 2, 1995, pp. 727–736.

Fry, M. J. et al., "Purification and characterization of a phosphatidylinositol 3–kinase complex from bovine brain by using phosphopeptide affinity columns," Biochem. J., vol. 288. 1992, pp. 383–393.
Hawkins, P. T., et al., "Platelet–derived growth factor stimulates synthesis of PtdIns(3,4,5)$P_3$ by activating a PtdIns(4,5)$P_2$ 3–OH kinase," Nature, vol. 358, Jul. 9, 1992, pp. 157–159.
Herman, P. K., et al., "Characterization of VPS34, a Gene Required for Vacuolar Protein Sorting and Vacuole Segregation in *Saccharomyces cerevisiae*," Molecular and Cellular Biology, vol. 10, No. 12, Dec. 1990, pp. 6742–6754.
Hiles, I. D., et al., "Phosphatidylinositol 3–Kinase: Structure and Expression of the 110 kd Catalytic Subunit," Cell, vol. 70, Aug. 7, 1992, pp. 419–429.
Holt, K. H., et al., "Phosphatidylinositol 3–Kinase Activation Is Mediated by High–Affinity Interactions between Distinct Domains within the p110 and p85 Subunits," Molecular and Cellular Biology, vol. 14, No. 1, Jan. 1994, pp. 42–49.
Hu, P., et al., "Interaction of Phosphatidylinositol 3–Kinase–Associated p85 with Epidermal Growth Factor and Platelet–Derived Growth Factor Receptors," Molecular and Cellular Biology, vol. 12, No. 3, Mar. 1992, pp. 981–990.
Hu, Q., et al., "Ras–Dependent Induction of Cellular Responses by Constitutively Active Phosphatidylinositol–3 Kinase" Science, vol. 268, Apr. 7, 1995 pp. 100–102.
Kapeller, R., et al., "Phosphatidylinositol 3–Kinase," Bioessays, vol. 16, No. 8, Aug. 1994, pp. 565–576.
Kaplan, D. R., et al., "Common Elements in Growth Factor Stimulation and Oncogenic Transformation: 85 kd Phosphoprotein and Phosphatidylinositol Kinase Activity," Cell, vol. 50, Sep. 25, 1987, pp. 1021–1029.
Klippel, A., et al., "The Interaction of Small Domains between the Subunits of Phosphatidylinositol 3–Kinase Determines Enzyme Activity," Molecular and Cellular Biology, vol. 14, No. 4, Apr. 1994, pp. 2675–2685.
Kunz, J., et al., "Target of Rapamycin in Yeast, TOR2, Is an Essential Phosphatidylinositol Kinase Homolog Required for $G_1$ Progression," Cell, vol. 73, May 7, 1993, pp. 585–596.

(List continued on next page.)

*Primary Examiner*—Ponnathapu Achutamurthy
*Assistant Examiner*—Kathleen Kerr
(74) *Attorney, Agent, or Firm*—Townsend & Townsend & Crew

(57) ABSTRACT

The present invention generally provides nucleic acids and polypeptides that are phosphatidylinositol 3-kinases, also known as 1-phosphatidylinositol 3-kinases. The nucleic acids and polypeptides disclosed are derived from Drosophila and mouse. These polypeptides are generally involved in cell signaling cascades which control, e.g., cell cycle progression and intracellular protein sorting. The family of PI3-kinases from which the polypeptides of the invention are derived are generally characterized by their structure as well as their unique substrate specificity.

9 Claims, 22 Drawing Sheets

MacDougall, L. K., et al., "A family of phosphoinositide 3–kinases in Drosophila identifies a new mediator of signal transduction," Current Biology, vol. 5., No. 12, 1995, pp. 1404–1415.

MacDougall, L. K., et al., "Characterization of a Novel Phosphatidylinositol 3–Kinase in Drosophila, Abstract in Abstract of papers presented at the 1995 meeting on Tyrosine Phosphorylation & Cell Signaling," May 3–7, 1995,Cold Spring Habor, New York, p. 113.

McGlade, C. J., et al., "SH2 Domains of the p85 Subunit of Phosphatidylinositol 3–Kinase Regulate Binding to Growth Factor Receptors," Molecular and Cellular Biology, vol. 12, No. 3, Mar. 1992, pp. 991–997.

Metzger, D., "The human oestrogen receptor functions in yeast," Nature, vol. 334, Jul. 7, 1988, pp. 31–36.

Molz, L., et al., "Identification of A P13 Kinase Homologue in *Drosophila melanogastor*," Abstract of papers presented at the 1995 meeting on Tyrosine Phosphorylation & Cell Signaling, May 3–7, 1995, p. 123.

Molz, L., et al., "Identification of a P13 Kinase Homologue in *Drosophila melanogastor*," 36th Annual Drosophila Research Conference, The Westin Peachtree Plaza, Atlanta, Georgia, Program and Abstracts Volume, Apr. 5–9, 1995, p. 60.

Molz, L., et al., "Cpk Is a Novel Class of Drosophila PtdIns 3–Kinase Containing a C2 Domain," Journal of Biological Chemistry, vol. 271, No. 23, Jun. 7, 1996, pp. 13892–13899.

Morgan, S. J., et al., "Purification and characterization of bovine brain type I phosphatidylinositol kinase," European Journal of Biochemistry, vol. 1990, pp. 761–767.

Nakanishi, H., et al., "Activation of the ξ Isozyme of Protein Kinase C by Phosphatidylinositol 3,4,5–Trisphosphate," Journal of Biological Chemistry, vol. 268, No. 1, Jan. 5, 1993, pp. 13–16.

Reedijk, M., et al., "Tyr721 regulates specific binding of the CSF–1 receptor kinase insert to PI''–kinase SH2 domains: a model for SH2–medicated receptor—target interactions," EMBO Journal, vol. 11, No. 4, 1992, pp. 1365–1372.

Schu, P. V., et al., "Phosphatidylinositol 3–Kinase Encoded by Yeast VPS34 Gene Essential for Protein Sorting," Science, vol. 260, Apr. 1993, pp. 88–91.

Shibaski, F., et al., "Two Types of Phosphatidylinositol 3–Kinase from Bovine Thymus," Journal of Biological Chemistry, vol. 266, No. 13, May 5, 1991, pp. 8108–8114.

Stephens, L. R., et al., "Agonist–stimulated synthesis of phosphatidylinositol(3,4,5)–trisphosphate: a new intracellular signalling system?" Biochimica et Biophysica Acta, vol. 1179, 1993, pp. 27–75.

Stephens, L. R., et al., "Pathway of phosphatidylinositol(3, 4,5)–trisphosphate synthesis in activated neutrophils," Nature, vol. 351, May 2, 1991, pp. 33–39.

Stoyanov, B., et al., "Cloning and Characterization of a G Protein–Activated Human Phosphoinositide–3 Kinase," Science, vol. 269, Aug. 4, 1995, pp. 690–693.

Toker, A., et al., "Activation of Protein Kinase C Family Members by the Novel Polyphosphoinositides PtdIns–3, 4–$P_2$ and PtdIns–3,4,5–$P_3$," Journal of Biological Chemistry, vol. 269, No. 51, Dec. 23, 1994, pp. 32358–32367.

Traynor–Kaplan, A. E., et al., "An inositol tetrakisphosphate–containing phospholipid in activated neutrophils," Nature, vol. 334, Jul. 28, 1988, pp. 353–356.

Traynor–Kaplan, A. E., et al., "Transient Increase in Phosphatidylinositol 3,4–Bisphospate and Phosphatidylinositol Trisphosphate during Activation of Human Neutrophils," Journal of Biological Chemistry, vol. 264, No. 26, Sep. 15, 1989, pp. 15668–15673.

Vanhaesebroeck, B., et al., "The Study of Phosphoinositide 3–kinase Function," Cancer Surveys, vol. 27, Cell Signalling, 1996, pp. 249–270.

Virbasius, J., et al., "Mouse p170 Is a Novel Phosphatidylinositol 3–Kinase Containing a C2 Domain," Journal of Biological Chemistry, vol. 271, No. 23, Jun. 7, 1996, pp. 13304–13307.

Volinia, S., et al., "A human phosphatidylinositol 3–Kinase complex related to the yeast Vps34–Vps15p protein sorting system," EMBO Journal, vol. 14, No. 14, 1995, pp. 3339–3348.

Whitman, M., et al., "Type I phosphatidylinositol kinase makes a novel inositol phospholipid, phosphatidylinositol–3–phosphate," Nature, vol. 332, Apr. 14, 1988, pp. 644–646.

Yoakim, M., et al., "Interactions of Polyomavirus Middle T with the SH2 Domains of the pp85 Subunit of Phosphatidylinositol–3–Kinase," Journal of Virology, vol. 66, No. 9, Sep. 1992, pp. 5485–5491.

Yonezawa, K., et al., "Insulin–dependent Formation of a Complex Containing an 85–kDa Subunit of Phosphatidylinositol 3–kinase and Tyrosine–phosphorylated Insulin Receptor Substrate 1," Journal of Biological Chemistry, vol. 267, No. 36, Dec. 25, 1992, pp. 25958–25965.

Zvelebil, M. J., et al., "Structural and functional diversity of phosphoinositide 3–kinases," Phil. Trans. R. Soc. Lond. B. vol. 351, 1996, pp. 217–223.

* cited by examiner

```
cpk    MSNQAHIDYDKQFQDDLAKATALSLEQHALDDYRRNKKYGSYQQSSTVAGRDYQAAQRSQSLHQPRRHSEVHQVAISPENAERSRTPPAQ    91
cpk-m  ..........................................................................................MAQ      3 cpk    GTDNDLICFASPTSKQPESSSFGKLIEDLQRMQPTNPQSALVFMGPVAGASIPPQYGFPPHQQRPTAACPTFYGMVAGGVVGGPAYG..D    180
cpk-m  ISNWSEF.......KQCSSSHPEPIRTKDVNKAEA......LQMEAPAIAKL........QKDRQMTDSPRGEPLSSSTRQRTQGFNKQD     72 cpk    LQLVPYQFNAQDQRPLNSEEIQRLYSMPAQMAVVPVPQPNAYMYYFGAMVTPYTAPIVPGSAAFMPPQYPAQGYGFGGAYTHMDLRRPQSQ    271
cpk-m  YDLMVEPEDDSQKRAVDI.DVEKL.TQAELEKILLDDNFETRKPEALFVTPVLSPSFS.....................IDLMLRPSGQR    139 cpk    PAPQQTAPTTSHHHSQPSNHSTSSPAEANGVAFPARRQVPSTVGVSSSSHTGNNGHSSMPRRGNDLIDLNHEDYSRVSVLEAFDPLLNDNT    362
cpk-m  GQWPPGLCGPSTYTLPSTYPSAYSKQATFQNGFSPRMPTFPSTESVYLRLPGQSPYFSPELTPA.......TPFHPQGSLPVYRPLVSPDM    223 cpk    G...NDTASDSTSYYAEYDPFDFLYSGDAATQYS...DPMYEAVNRWDKTVATVSPNMGIIGARQDFLSQPSTSSSQYGVAPPEESLKLAE    447
cpk-m  AKLFEKIASTSEFLKNGKARTDLEIANSKASVCNLQISPKSEDINKFDW........LDLDPWDAVLLEERS.PSCHLERKVNGKSL....    301 cpk    NGSGTISPPPPLPPRNQQCYESNQAAMPVSRPPQSSVLTDSYTSSIPANVVLDRRKTCTRLYELTSDQRTDDPELIEFYHMVKEVRARYTH    538
cpk-m  .SGATVIRSQSUIIRTAGFTKADGQVSQKDPNGTSSLPTKS....................SLIQEFEVQNDEVAAECQSLMKLKTKFEY    370 cpk    DDAPTNVGHVVAAEFNYHYMMDTSIKVIVHPAINTIQSTVLAASMGKEQVKGYGMPVTFTCDIDSVVAQVVAQALASDEGQV.KGTVTDYA    628
cpk-m  TDHQTNFGYLLSP.............VTMQRNMCGENASV....KVSIELDGLQLPVTFTCDVSSTVEILIMQALCWMHDDLNQVDVGSYI    444 cpk    VRPIGLIEWLAPTSRLSQLEQVHNSFQLEKDVHLGICLSTAANMQAIARTERDDEHDADILP.EHLLPNEVVQIVTYDNMMILIETLEMED    718
cpk-m  LKVCGQPEVLQNNHCLGSHEHIDNCRKWDTEIKLQL.LTLSAMCQNLARTAEDDEAPVDLNKYLYQIEKPYKEVMIRHPVEFLLDSYHYQV    534 cpk    DKLESAADGVPGRSVVSCSGVVQAVRAICALLGSIDTMEIARCVADLKRICEMEQKRYSTGASNPEIVSDYGDYAQVVLRPRSMLEQIKVK    809
cpk-m  ...DLALQTENQHRAV..DQVIKAVRKICSALDGVETPSVTEAVKKLKRAVNLPRNKSADVTS....LSGSDTRKNSTKGSLNPENPVQMS    616 cpk    CNEIRDAVQELVQDIYANVFRVAFSVKTPDYSTTPIPISCVSKPLVVCISCLHRPLPNW..KFDDMSICVQIVYGTRLISKPNMLTCSNDTS    898
cpk-m  MDHLTTAIMDLIRLHANSSRC..STGCERGSRNIKEAWTATEQLQFTMYAAHGISSNWVSNYEKMYLICSLSHNGKDLFKP.IKQSKKVGTY    704 cpk    GGIFPRDNFSAWLTFDQHPTCTLPREARLITFVLYGKQAASEGEPNADQNGERRQVTTELGWCSTQLFDFKRVMICGPYLISLWPPMTDKML    989
cpk-m  KNFEYILKWDEIHIFPIQ.DSQLFLESVLHLTLFGVLNQSSG..SSPDSNKQRKGPEALGKVSITLFDFKRFLTCGTKLLYLWTSSHTNSL    792 cpk    GPAPARGCHPQPDFCPVISIEVPPYGGRIEFPEHQEVPKPAPHYDFASLDANLQEELLDTA..ELGYTGATERREVFWEKRLMLQSYPNAL    1078
cpk-m  PGAIPMKSYVMERI..VLQVDFESPAFDDILYTSPGIDRNIIQQDKLETLESDLKGKLLDIIHRDSSEGLSKEDKVFLWENRMYCLKHPNCL     881 cpk    PKVIHAAHSWDYANLIDLHALIHSMAPISPIQSLELILPRYPDAKVREKAVEWISKMPNDQLVDFLPQLVQSLKHDTMEGSAMARFLLSKC    1169
cpk-m  PKIIASAPNWKWANLAKTYSLLHQWPPILCPIAALELILDAKFADQGVRSLAVSWMEAUSDDELADIILPQFVQALKYEIMLNSSLVRFLLSRA     972 cpk    IESPRFAHHMYWLIVHSIPDDPHNSIGAAMVDQEYDESQVTQVRYYRRNKMMIHALMAITGEKMLQRFMYQHRMLQKLTTIAESVKEAKES    1260
cpk-m  IGNIQIAHSLYWLIKDALHDTHFGS.................RYEHVLGALISVGGKGLREELSKQMKLVQILGGVAEKVRQASGS         1041 cpk    MRQKSIAAGMDEMHQDLIEQPTCLPLGPELEVTGVSVRNCSYFNSNILPLKINFVGPD..AESLPAIFKCGDDILQQDQLTIQLIRIMNKMW    1349
cpk-m  TRQVVLQKSMERVQSFFLRNKCRLPLKESLVAKELNIKSCSFFSSNAMPLKVTMVNADPLGEFINVMFKVGEDLRQDMIALQMIKIMDKIW    1132 cpk    LADRLDLKMVTFNCVPTGYKSGMIELVSEAETLRKIQVEQGLTGSFKDRPIAEWIGKQNPSPLEYQSPAVRNFTILSCAGYSVATYVLGICDR    1440
cpk-m  LAEGLDLRMVIFRCLSTGRDRGMVELVPASDTLRKIQVEYGVTGSFKDKPLAEWIRKYNPSEFEYEKASPNFIYSCAGCCVATYVLGICDR    1223 cpk    HNDNIMLKTSGHLFHRIDFGKFLGDAQMFGNFKRDRIPFVLTSDMAYVINGGDKPSTDFHYFVDLCQRAFNIVRRKNADLLLHTIAHMATAGM    1531
cpk-m  HNDNIMLRSTGHMFRIDFGKFLGHAQMFGSFKRDRAPFVLTSDMAYVINGGEKPTIRFQIFVDLCCQAYNLIRKQTNLFLNLLSLMIPSGL    1314 cpk    PGVNSL.NAMQYVRRAILESQSNPEAARATFAKMIQSSLKSWFIQFNFFIHNLAQMRFTPDEGSGE.LLLSFMPRKYTMQQDGRLKIVKWVCFQ    1620
cpk-m  PPLISKQLLKYVRDAIQEQTDDAEAITIFFTRLIESSLGSIATKFNFFIHNLAQLRFSGLPSNDEPILSFSPKTYSFRQDGRIKEVSVFTYH    1405 cpk    RHVSMEKEYMYILEVTRHGQPDPTHLFRSYREFTDFHQKLCMHFPIMKLHSLPAGVHVGRSN.RSVAEKRLPLTQRFIKSLFDASEEIIAH    1710
cpk-m  KKYNPDKHYIYVVRLLSEGHLEPSFVFRTEDEFQELHNKLSUIFPLWKLPGFENRMVLGRTHIKDVAAKRKIELNSYLQSLMNASTDVAEC    1496 cpk    SELVMTFFHPLLRDQQEAKTGMPKIKEVKQOPSRDNPHEIRQTRLSLQYQRGVLTVMIHHAKGLPMLQGGQEPNTYVRCYLKPDPKKETKR    1801
cpk-m  .DLVCTFFHPLLRDEKAEGIARS...AGAVPFSPTLGQIGAVKLSVSYRNGTLFIMVMHIKDL.MTEDGADPNPYVKTYLIPDTHKTSKR    1583 cpk    KTKVVRKTCVPSFMETILEVR.MPLNIIQEFRRLQVTVMSHDTILQENELLGGFDMDLSKMQDLRQELMDWYRLQGAVSRN*              1876
cpk-m  KTKIJSRKTRNPTFNEMLVYSGYSKETLRQHELQLSVLSAESLRENFFLGGITLPLKDFNLSKETVKHWYQLTAATYL*              1658
```

Fig. 1

```
cpk      A FKQGDDIQDQLT QLIRIMNKMI AERI ....      DLKMVTFNQVPTGYKSGMIELVSEAETLRKIQV...    ECGLTGSFKDRPTAEWIGKQ..N  1408
cpk-m    VMFKVGDDIRQDML AIQMIRIMKMIWIKEGI ....     DIFMIERCLSTGRDRGMELVPASDTLRKIQV...      EYGMTGSFKDKPTAEWIRKY..N  1191
p110α    I IFKNGDDIRQDML TIQMIQLRIMENIMQNGI ....   DIFRMLPYGCLSIGDCVGLIEWSTIMQIQ.C.        KGGLKGALQFNSHTLHQWIKDK.N  870
p110β    V IFKNGDDIRQDML TIQMIQLRIMENIMKEAGI ....   DIFRMLPYGCLATGDHSGLIEWVSTSETIADIQLN.    SSNVAAAAENKDALLNWIKEY..N  888
p110γ    I LFKHGDDIRQDMI IQLRIMESINETESL ....       DICLLPYGCISTGDKGMIEIMKDATTIAKIQ.        QSTVGNTGAEKDEVLNHWIKEK.S  881
Vps34    LMEKVGDDIRQDQI VQLILSIMNELLKNENV ....       DLKLTPYKILATGPQEGALEEFIPN.DTIASILS...   KYHGILGYIKLH..Y          696
Pik1     L FANTGDDIRQDIP EAFAYQMIQAMANIMKEKV ....    DIVWVKRMKILITNSANTLVETITNAMSVHSIKKALTKKMIEDAELDDKGGIASLNDHFLR  883
Tor2     YVLKGHEDIRQDSIVMQQIFGLVNTLIQNDAECFRRHIDIQQYPAIPLSPLKSGLLGWMPNSDIFHVLIREHREAKKIPLNIEHWMLQ.MAPDYDN  2218 cpk       PSPLEY.....QSAVRN.                                FTLSCAGYSVATYVLGICDRHNDNIMLKT.SGHLFHIDFGKFLGDAQMFGNFKRDRTPFVLTSDMAYVINGGDKP  1594
cpk-m     PSEDEY.....EKASEN.                                FIYSCAGCVATYVLGICDRHNDNIMLRS.TGHMFHIDFGKFLGFIDHKKKKFGYKREAPFVLTSDMAYVINGGEKP  1277
p110α     KGEI.Y.....DAAIDL.                                FTRSCAGYCVATYVLGIGDRHNSDNIMVKD.DGQLFHIDFGHILGNFKSKFGIKREFVPFELTMDFIHVISKGAQE..K  955
p110β     SGDD.L.....DRAIEE.                                FLLSCAGYVASYVLGIGDRHSDNIMVKK.TGQLFHIDFGHILGNYKSFLGINKEBVPFVLPDFLFMDFIHVJQOG..K  972
p110γ     ETEEKF.....QAAVER.                                FVKSCAGYVATEVLGYLLTYIQLLQVGDRHLDNLLVTP.DGHFFEHADFGYILG.                         967
Vps34     EDENATLGVQGWVLDN.                                 EASSIAALSVICYILLQVKDRHNGNIMLDN.EGHVSHIDFGFMISNSPGSVGE..EAAFFKLTYEYIELLGGVEGE..S 781
Pik1      AFGNPNGFKYRRAQDN.                                 KVKSCAGYOMITYFLGIGDRHNDN (appears partial)                                       971
Tor2      LTTLDQKVEVFTYALN.(26) YTRSIAVMSMTCYILGLGDRHPSNIMIDRITGKVIHIDFEGDCFEAAILREKE.PEKVPFRLTRMLTYAMEVSGIE  2335
```

Fig. 2C

```
   1 GCTTGTTGCATTCCGTTTTGTGTTATTTCGTGCTCCCCGTCAAGGGAAAACCTCAACCAA
  61 AAAGAGACTAGCAACGGGTGTAAAAAGCAGCGGAGGTGACACCTCAAAAAGCAACTCAAC
 121 GGACCGGACGCTTTAGACGAGGGGATAATGTCAAATCAAGCGCATATCGACTACGACAAA
   1                                 M  S  N  Q  A  H  I  D  Y  D  K
 181 CAATTCCAGGATGACCTGGCCAAGGCGACCGCCCTGAGTCTAGAGCAGCATGCCCTCGAT
  12  Q  F  Q  D  D  L  A  K  A  T  A  L  S  L  E  Q  H  A  L  D
 241 GACTACAGGCGAAACAAGAAGTACGGCTCCGGGTATCAGCAAAGCTCCACCGTTGCTGGC
  32  D  Y  R  R  N  K  K  Y  G  S  G  Y  Q  Q  S  S  T  V  A  G
 301 CGAGATTACCAGGCGGCGCAACGTAGTCAGAGCCTACATCAACCACGACGGCACTCGGAG
  52  R  D  Y  Q  A  A  Q  R  S  Q  S  L  H  Q  P  R  R  H  S  E
 361 GTGCATCAGGTGGCCATCAGTCCGGAGAATGCGGAACGATCGCGCACACCGCCGGCCCAG
  72  V  H  Q  V  A  I  S  P  E  N  A  E  R  S  R  T  P  P  A  Q
 421 GGAACGGATAACGATCTGATCTGCTTCGCAAGTCCCACCAGCAAGCAGCCAGAGAGTAGC
  92  G  T  D  N  D  L  I  C  F  A  S  P  T  S  K  Q  P  E  S  S
 481 AGTCCCTTTGGCAAACTTATAGAGGATCTGCAGCGGATGCAGCCGACCAATCCGCAGTCG
 112  S  P  F  G  K  L  I  E  D  L  Q  R  M  Q  P  T  N  P  Q  S
 541 GCCCTGGTGCCAATGGGTCCAGTTGCGTCGGCTTCGATTCCTCCTCAATACGGCTTTCCA
 132  A  L  V  P  M  G  P  V  A  S  A  S  I  P  P  Q  Y  G  F  P
 601 CCTCATCAGCAACGTCCAACGGCTGCTCAGCCCACACCGTACGGCATGGTTGCAGGTGGA
 152  P  H  Q  Q  R  P  T  A  A  Q  P  T  P  Y  G  M  V  A  G  G
 661 GTTGTTGGTGGACCGGCTTACGGTGACCTGCAGTTGGTGCCTTACCAACCAGCTGCCCAG
 172  V  V  G  G  P  A  Y  G  D  L  Q  L  V  P  Y  Q  P  A  A  Q
 721 CAACAGAGGCCACTAAACAGCGAGGAGCTGCAGCGGCTGTACAGCATGCCCGCTCAAATG
 192  Q  Q  R  P  L  N  S  E  E  L  Q  R  L  Y  S  M  P  A  Q  M
 781 GCCGTGGTTCCAGTGCCGCAGCCAAACGCCTATATGTACTATCCCGGAGCTGTGGTTACT
 212  A  V  V  P  V  P  Q  P  N  A  Y  M  Y  Y  P  G  A  V  V  T
 841 CCATACACGGCTCCCATTGTTCCCGGATCGGCTGCTTTTATGCCGCCGCAGTATCCCGCA
 232  P  Y  T  A  P  I  V  P  G  S  A  A  F  M  P  P  Q  Y  P  A
 901 CAGGGATATGGCTTTGGAGGTGCTTACACGCACATGGATTTGCGTCGACCCCAATCGCAA
 252  Q  G  Y  G  F  G  G  A  Y  T  H  M  D  L  R  R  P  Q  S  Q
 961 CCAGCTCCCCAACAAACAGCACCGACAACAAGTCATCATCACAGCCAACCGTCCAACCAT
 272  P  A  P  Q  Q  T  A  P  T  T  S  H  H  H  S  Q  P  S  N  H
1021 TCCACTTCCTCCCCCGCAGAGGCCAATGGAGTAGCCTTCCCAGCGCGTCGCCAAGTGCCC
 292  S  T  S  S  P  A  E  A  N  G  V  A  F  P  A  R  R  Q  V  P
1081 TCGACTGTCGGGGTTAGCTCTAGTAGCCACACTGGAAACAATGGTCATTCCTCGGTCCCA
 312  S  T  V  G  V  S  S  S  S  H  T  G  N  N  G  H  S  S  V  P
1141 CGCAGGGGCAACGATTTGATCGACCTCAACCACGAGGACTACTCCCGTGTGAGTGTGCTG
 332  R  R  G  N  D  L  I  D  L  N  H  E  D  Y  S  R  V  S  V  L
1201 GAGGCATTCGATCCCCTGCTAAACGACAATACTGGCAACGACACCGCCTCCGACAGCACT
 352  E  A  F  D  P  L  L  N  D  N  T  G  N  D  T  A  S  D  S  T
1261 TCCTACTATGCGGAATACGATCCCTTTGATTTTCTGTACAGCGGAGATGCAGCAACCCAA
 372  S  Y  Y  A  E  Y  D  P  F  D  F  L  Y  S  G  D  A  A  T  Q
1321 TATTCCGATCCAATGTATGAGGCAGTCAACAGGTGGGACAAAACTGTGGCCACCGTGAGT
 392  Y  S  D  P  M  Y  E  A  V  N  R  W  D  K  T  V  A  T  V  S
1381 CCGAATGTTGGTCTAATCGGTTGGCGCCAAGATTTTCTGAGCCAGCCATCTACATCTTCA
 412  P  N  V  G  L  I  G  W  R  Q  D  F  L  S  Q  P  S  T  S  S
1441 TCGCAATATGGTGTTGCGCCGCCAGAGGAGAGTCTGAAGCTTGCGGAGAACGGATCTGGA
 432  S  Q  Y  G  V  A  P  P  E  E  S  L  K  L  A  E  N  G  S  G
1501 ACTATCTCGCCTCCTCCGCCGTTGCCGCCCCGGAACCAGCAGTGCTATGAATCAAACCAG
 452  T  I  S  P  P  P  L  P  P  R  N  Q  Q  C  Y  E  S  N  Q
1561 GCAGCCATGCCGGTCTCCAGGCCTCCTCAGTCTTCTGTTTTGACGGACAGCTACACCTCC
 472  A  A  M  P  V  S  R  P  P  Q  S  S  V  L  T  D  S  Y  T  S
1621 AGCATTCCGGCCAACGTGGTGCTGGACCGGCGGAAAACTTGTACACGACTGTACGAATTG
 492  S  I  P  A  N  V  V  L  D  R  R  K  T  C  T  R  L  Y  E  L
1681 ATCAGCGACCAGCGCACTGATGATCCCGAACTTTTGGAATTTTACCACATGGTAAAGGAG
 512  I  S  D  Q  R  T  D  D  P  E  L  L  E  F  Y  H  M  V  K  E
1741 GTGAGGGCACGCTATCCGCATGACGATGCGCCCACCAATGTGGGACATGTTGTGGCCGCC
```

Fig. 9
Page 1 of 4

```
 532        V  R  A  R  Y  P  H  D  D  A  P  T  N  V  G  H  V  V  A  A
1801        GAGTTTAATTATCACTACATGATGGACACCAGCATCAAAGTGATTGTGCATCCGGCTCTA
 552        E  F  N  Y  H  Y  M  M  D  T  S  I  K  V  I  V  H  P  A  L
1861        AATACACTTCAATCAACGGTCCTGGCTGCGTCCATGGGCAAGGAACAGGTGAAGGGATAT
 572        N  T  L  Q  S  T  V  L  A  A  S  M  G  K  E  Q  V  K  G  Y
1921        GGAATGCCAGTAACATTCACTTGCGATATTGATTCGGTTGTGGCACAGGTGGTGGCACAA
 592        G  M  P  V  T  F  T  C  D  I  D  S  V  V  A  Q  V  V  A  Q
1981        GCTTTGGCCTCGCTGGAGGGACAAGTCAAGGGTACCGTCACAGATTATGCGGTCAAGCCC
 612        A  L  A  S  L  E  G  Q  V  K  G  T  V  T  D  Y  A  V  K  P
2041        ATTGGTCTTCTGGAGTGGCTGGCACCCACCTCGAGACTGAGTCAGCTGGAGTGCGTGCAC
 632        I  G  L  L  E  W  L  A  P  T  S  R  L  S  Q  L  E  C  V  H
2101        AATAGCTTCCAATTGGAGAAGGATGTACATTTGGGCCTGTGCCTTAGTACGGCGGCAAAC
 652        N  S  F  Q  L  E  K  D  V  H  L  G  L  C  L  S  T  A  A  N
2161        ATGCAGGCTATTGCACGAACAGAGCGGGATGATGAGCACGATGCGGATTTGCTGCCGGAA
 672        M  Q  A  I  A  R  T  E  R  D  D  E  H  D  A  D  L  L  P  E
2221        CATCTTCTTCCAAACGAGGTTGTGCAAATTGTGACCTACGACAATATGATGATACTCATC
 692        H  L  L  P  N  E  V  V  Q  I  V  T  Y  D  N  M  M  I  L  I
2281        GAAACGCTGGAGATGGAGATTGACAAGCTGGAATCGGCGGCCGACGGAGTACCCGGACGG
 712        E  T  L  E  M  E  I  D  K  L  E  S  A  A  D  G  V  P  G  R
2341        AGTGTCGTGAGCTGCTCCGGAGTTGTCCAAGCAGTGAAGGCCATATGCGCACTGCTCGGT
 732        S  V  V  S  C  S  G  V  V  Q  A  V  K  A  I  C  A  L  L  G
2401        TCAATCGACACAATGGAAATTGCACGATGTGTTGCCGATCTGAAGCGCATTTGCGAGGTG
 752        S  I  D  T  M  E  I  A  R  C  V  A  D  L  K  R  I  C  E  V
2461        GAGCAAAAGAAGTACTCGACGGGCGCTAGCAACCCAGAGATTGTGAGTGACTATGGTGAT
 772        E  Q  K  K  Y  S  T  G  A  S  N  P  E  I  V  S  D  Y  G  D
2521        TACGCTCAAGTTGTACTCCGCCCGCGCTCCATGCTGGAGCAGATCAAGGTCAAGTGCAAC
 792        Y  A  Q  V  V  L  R  P  R  S  M  L  E  Q  I  K  V  K  C  N
2581        GAGCTGCGAGATGCAGTGCAAGAGCTGGTTGAATTGTATGCGAATGTTTTCCGGGTGGCA
 812        E  L  R  D  A  V  Q  E  L  V  E  L  Y  A  N  V  F  R  V  A
2641        TTCTCCGTGAAGACGCCCGATTACTCAACAACACCCATACCCATTTCCTGCGTGTCCAAA
 832        F  S  V  K  T  P  D  Y  S  T  T  P  I  P  I  S  C  V  S  K
2701        CCAATTGTGGTATGCATTAGCTGCCTACACAGGCCGCTGCCGAATTGGAAGTTCGACGAT
 852        P  I  V  V  C  I  S  C  L  H  R  P  L  P  N  W  K  F  D  D
2761        TATTCCCTGTGCGTACAAATCGTTTATGGAACGCGCCTGCTGTCGAAGCCGAATGTGCTG
 872        Y  S  L  C  V  Q  I  V  Y  G  T  R  L  L  S  K  P  N  V  L
2821        ACCTGCTCCAACGATACAAGTGGAGGCCTGTTTCCTCGTCTTAACTTCAGTGCCTGGCTG
 892        T  C  S  N  D  T  S  G  G  L  F  P  R  L  N  F  S  A  W  L
2881        ACTTTCGATCAGCATCCCATCTGCACTCTGCCCAGGGAGGCGCGCCTTACGTTCGTGTTG
 912        T  F  D  Q  H  P  I  C  T  L  P  R  E  A  R  L  T  F  V  L
2941        TATGGAAAACAGGCGGCCAGCGAAGGCGAACCCAACGCCGATCAGAATGGAGAGAGGCGT
 932        Y  G  K  Q  A  A  S  E  G  E  P  N  A  D  Q  N  G  E  R  R
3001        CAGGTGACCACTGAACTGGGTTGGTGTTCGATCCAACTGTTTGACTTTAAGCGAGTGATG
 952        Q  V  T  T  E  L  G  W  C  S  I  Q  L  F  D  F  K  R  V  M
3061        ATCTGCGGCCCCTACTTACTGTCTTTATGGCCACCAATGACGGACAAAATGCTTGGACCA
 972        I  C  G  P  Y  L  L  S  L  W  P  P  M  T  D  K  M  L  G  P
3121        GCTCCGGCTCGAGGCTGTCATCCGCAACCCGACTTTTGCCCCGTTTTGAGCATTGAAGTA
 992        A  P  A  R  G  C  H  P  Q  P  D  F  C  P  V  L  S  I  E  V
3181        CCTCCGTATGGAGGACGCATTGAGTTTCCTGAGCACCAGGAGGTGCCAAAACCTGCACCA
1012        P  P  Y  G  G  R  I  E  F  P  E  H  Q  E  V  P  K  P  A  P
3241        CACTACGATTTTGCCTCTCTGGATGCCAATCTTCAAGAGGAGCTGCTGGACACCGCAGAG
1032        H  Y  D  F  A  S  L  D  A  N  L  Q  E  E  L  L  D  T  A  E
3301        CTGGGCTACACAGGAGCCACAGAACGACGTGAAGTGTTCTGGGAAAAACGGCTCTACCTG
1052        L  G  Y  T  G  A  T  E  R  R  E  V  F  W  E  K  R  L  Y  L
3361        CAGAGCTATCCCAATGCCCTGCCAAAGGTTCTTCATGCCGCTCACAGTTGGGATTATGCC
1072        Q  S  Y  P  N  A  L  P  K  V  L  H  A  A  H  S  W  D  Y  A
3421        AATTTGATCGATTTGCATGCGCTGCTGCACTCCTGGGCACCACTCTCGCCATTGCAGTCG
1092        N  L  I  D  L  H  A  L  L  H  S  W  A  P  L  S  P  L  Q  S
3481        TTGGAGTTACTTCTGCCACGATATCCGGATGCTAAGGTTCGCGAGAAAGCCGTGGAGTGG
```

Fig. 9

```
1112  L  E  L  L  L  P  R  Y  P  D  A  K  V  R  E  K  A  V  E  W
3541  ATCTCCAAGATGCCCAACGACCAGCTCGTCGACTTTCTGCCTCAATTGGTGCAAAGTTTA
1132  I  S  K  M  P  N  D  Q  L  V  D  F  L  P  Q  L  V  Q  S  L
3601  AAACATGACACATACGAAGGCTCGGCAATGGCTCGATTCTTGCTGTCCAAATGCCTGGAG
1152  K  H  D  T  Y  E  G  S  A  M  A  R  F  L  L  S  K  C  L  E
3661  TCACCGCGCTTTGCCCATCACATGTATTGGCTGCTTGTACACAGTCTGCCTGACGATCCC
1172  S  P  R  F  A  H  H  M  Y  W  L  L  V  H  S  L  P  D  D  P
3721  CACAACTCTATTGGAGCAGCGATGGTGGATCAGGAGTATGACGAGTCTCAGGTTACCCAG
1192  H  N  S  I  G  A  A  M  V  D  Q  E  Y  D  E  S  Q  V  T  Q
3781  GTCCGTTACTACCGCCGGAACAAAATGATGCTGCGTGCTTTAATGGCGATTTGCGGCGAA
1212  V  R  Y  Y  R  R  N  K  M  M  L  R  A  L  M  A  I  C  G  E
3841  AAGATGCTTCAGCGATTTATGTACCAGCACCGAATGTGTCAGAAACTTACTACTATTGCG
1232  K  M  L  Q  R  F  M  Y  Q  H  R  M  C  Q  K  L  T  T  I  A
3901  GAGTCGGTTAAAGAGGCTAAGGAGTCGATGCGTCAAAAAAGCCTAGCCGCAGGCATGGAC
1252  E  S  V  K  E  A  K  E  S  M  R  Q  K  S  L  A  A  G  M  D
3961  GAGGTGCACCAAGACTTACTGGAGCAACCCACTTGCCTACCGCTGGGACCAGAACTGGAG
1272  E  V  H  Q  D  L  L  E  Q  P  T  C  L  P  L  G  P  E  L  E
4021  GTAACTGGAGTGAGTGTGCGTAACTGTAGCTACTTTAACTCCAACACGCTGCCGCTGAAG
1292  V  T  G  V  S  V  R  N  C  S  Y  F  N  S  N  T  L  P  L  K
4081  ATCAACTTTGTGGGACCTGATGCCGAATCTTTACCGGCTATCTTTAAGTGCGGAGATGAC
1312  I  N  F  V  G  P  D  A  E  S  L  P  A  I  F  K  C  G  D  D
4141  TTGCAGCAGGATCAGTTAACTATACAGCTAATTAGGATTATGAACAAAATGTGGTTGGCC
1332  L  Q  Q  D  Q  L  T  I  Q  L  I  R  I  M  N  K  M  W  L  A
4201  GAACGATTGGACCTGAAGATGGTCACCTTTAATTGTGTGCCTACGGGATACAAGAGCGGT
1352  E  R  L  D  L  K  M  V  T  F  N  C  V  P  T  G  Y  K  S  G
4261  ATGATTGAGCTGGTTAGCGAGGCGGAAACGTTGAGAAAAATTCAAGTAGAGTGCGGTCTG
1372  M  I  E  L  V  S  E  A  E  T  L  R  K  I  Q  V  E  C  G  L
4321  ACGGGGTCCTTTAAGGATCGCCCGATCGCTGAGTGGTTAGGCAAGCAGAATCCCAGTCCT
1392  T  G  S  F  K  D  R  P  I  A  E  W  L  G  K  Q  N  P  S  P
4381  CTCGAGTACCAGAGTGCTGTGCGAAATTTTACGCTATCCTGTGCTGGATACAGTGTGGCC
1412  L  E  Y  Q  S  A  V  R  N  F  T  L  S  C  A  G  Y  S  V  A
4441  ACGTATGTGCTAGGCATCTGTGATCGCCACAATGACAACATCATGTTAAAGACTTCGGGT
1432  T  Y  V  L  G  I  C  D  R  H  N  D  N  I  M  L  K  T  S  G
4501  CACTTGTTTCACATTGACTTTGGCAAGTTTCTTGGCGATGCTCAGATGTTTGGAAACTTT
1452  H  L  F  H  I  D  F  G  K  F  L  G  D  A  Q  M  F  G  N  F
4561  AAGAGAGATCGCACTCCATTTGTCCTGACTTCCGACATGGCTTATGTCATAAATGGCGGC
1472  K  R  D  R  T  P  F  V  L  T  S  D  M  A  Y  V  I  N  G  G
4621  GATAAGCCCTCCACAGACTTTCACTATTTCGTGGACCTATGTTGTCGAGCCTTTAATATC
1492  D  K  P  S  T  D  F  H  Y  F  V  D  L  C  C  R  A  F  N  I
4681  GTGCGGAAAAATGCTGATCTACTCTTGCACACCCTGGCCCACATGGCTACAGCAGGCATG
1512  V  R  K  N  A  D  L  L  L  H  T  L  A  H  M  A  T  A  G  M
4741  CCGGGAGTAAACTCCAATGCTGTGCAATATGTACGACGCGCCCTATTGCCATCTCAATCG
1532  P  G  V  N  S  N  A  V  Q  Y  V  R  R  A  L  L  P  S  Q  S
4801  AATCCCGAGGCAGCTGCCACATTTGCCAAGATGATTCAATCCTCTTTGAAAAGCTGGTTC
1552  N  P  E  A  A  A  T  F  A  K  M  I  Q  S  S  L  K  S  W  F
4861  ACGCAATTCAATTTCTTTCTGCACAATCTGGCCCAGATGCGTTTCACCCCAGACGAGGGA
1572  T  Q  F  N  F  F  L  H  N  L  A  Q  M  R  F  T  P  D  E  G
4921  TCAGGAGAGCTGCTATCGTTCGTGCCACGAAAATATACAATGCAGCAGGATGGTCGCTTG
1592  S  G  E  L  L  S  F  V  P  R  K  Y  T  M  Q  Q  D  G  R  L
4981  AAGATTGTAAAGGTGGTGTGTTTCCAGAAGCATTACAGCATGGAAAAGTTTTATATGTAT
1612  K  I  V  K  V  V  C  F  Q  K  H  Y  S  M  E  K  F  Y  M  Y
5041  ATTCTGGAAGTGACGCGACATGGACAGCCCGATCCGACACATTTGTTCCGGTCATATCGG
1632  I  L  E  V  T  R  H  G  Q  P  D  P  T  H  L  F  R  S  Y  R
5101  GAATTCACGGAATTCCATCAGAAGTTATGCATGCACTTTCCTTTGGTTAAACTGCACAGT
1652  E  F  T  E  F  H  Q  K  L  C  M  H  F  P  L  V  K  L  H  S
5161  CTGCCGGCTGGTGTGCATGTGGGCCGTTCCAATATCAAATCCGTGGCAGAAAAACGACTA
1672  L  P  A  G  V  H  V  G  R  S  N  I  K  S  V  A  E  K  R  L
5221  CCTCTTATACAGCGATTTTTGAAATCGTTGTTCGATGCGTCCGAGGAAATAGCCCATTCC
```

Fig. 9

```
1692 P  L  I  Q  R  F  L  K  S  L  F  D  A  S  E  E  I  A  H  S
5281 GAGCTCGTTTACACATTCTTTCACCCGCTGCTGCGCGATCAGCAGGAAGCCAAGCTTGGG
1712 E  L  V  Y  T  F  F  H  P  L  L  R  D  Q  Q  E  A  K  L  G
5341 ATGCCGAAGATAAAGGAGGTGAAGCAACAACCGTCGCGGGATAATCCCCACGAGATTGGC
1732 M  P  K  I  K  E  V  K  Q  Q  P  S  R  D  N  P  H  E  I  G
5401 CAAATACGACTATCGCTGCAATATCAACGCGGCGTACTTACTGTGATGATACACCACGCC
1752 Q  I  R  L  S  L  Q  Y  Q  R  G  V  L  T  V  M  I  H  H  A
5461 AAAGGACTGCCCATGTTACAGGGCGGTCAGGAGCCCAACACATATGTGAAGTGCTACCTA
1772 K  G  L  P  M  L  Q  G  G  Q  E  P  N  T  Y  V  K  C  Y  L
5521 AAACCGGATCCCAAAAAGGAGACCAAACGCAAGACCAAAGTGGTGCGCAAGACCTGTGTG
1792 K  P  D  P  K  K  E  T  K  R  K  T  K  V  V  R  K  T  C  V
5581 CCCAGTTTCATGGAAACTTTGGAGTACCGAATGCCACTGAATATTATTCAAGAGCGCCGC
1812 P  S  F  M  E  T  L  E  Y  R  M  P  L  N  I  I  Q  E  R  R
5641 CTTCAGGTTACGGTTTGGTCGCACGACACCCTGCAGGAGAACGAGCTGCTTGGAGGCTTC
1832 L  Q  V  T  V  W  S  H  D  T  L  Q  E  N  E  L  L  G  F
5701 GATATGGATCTGTCGAAGTACGACCTGCGACAGGAGCTCGTCGACTGGTATCGCCTGGGC
1852 D  M  D  L  S  K  Y  D  L  R  Q  E  L  V  D  W  Y  R  L  G
5761 GCGGTGTCCAGGAACTGACCAGATCCTAGGGACGAGCTATTTTGAACCTCTTGGGACACT
1872 A  V  S  R  N  *
5821 CTGCCTACCGACAATCAGGCCTAGGATAATGCAATACTAATATATGTTTGTGCCTGTCTT
5881 CTTTCGATCGCAATAATACTTACTTACTCGAAGTGATTGTACATTCCATATACCAATATT
5941 AAAAATAACATAACAGTAGTAGTATTATTTCGTAAAATGTGTGCCTCAAATGTAAATATT
6001 TTATAATGACCGCAAACAACATTCTTTTGGACATCTGAATGTAATTATAACTATAAAGTA
6061 TAGAACATGCTTACTCTATTTACATTTAAAATCAATCAATTTTATTGTGCACCTTGGGAA
6121 TTCAGAAAATGAATTATATTGGTAGTTTGTTTGAATCGTTCTGTCGTCGGCACCTGGCAA
6181 TTGTTCTTTTGAAGTAGTTAAATATAAAAGTTCAGTATTATGGCTTAAATTCTATAAGAG
6241 ATTATTAAAAACCTTCTAGCTCGCTGGTCTGTAATATCTAAAATTAAAACTTGCACGAAG
6301 AATAATCATTACTAACTTTTTGCACTTTTCTAATTACTTAAAGTAAAAAGAGAACTAAA
6361 ATTTCCTAAAGAAATTAGGCATTGCAAGCAGAATAACGCACAGATACAGATTCTTTCTGA
6421 TTGTATTTTGTTTGTCACTTAATATTCACAAAATTGCTTTGTCAAAAGCAAACGCCTGAC
6481 TGGGTCTAAAACAAATTTACAAAGTTATAGGGAATTACTATCAGAGAGAACAAGAACTAA
6541 AAGTGTCTTAAAAATGAAACGAATATTGTAAAATATATAATAAGAGCACACACACACCGC
6601 AAACAACAAATTATATTTTATAGAAAAAAGAAACATTCAAAAGCTACTTCTGCCTGAGC
6661 ATTTCAAATAGTACTTTGATACTGATTAAAAACTACCTAAGACGTATCTGATGTTTTCAT
6721 AAAATTATAATTAATAGGAAAAAATTAAATTTCTGAAGTGTTGAGGAATCGTAAAAATGT
6781 TAGCTGGCGGTAATCACTTTTGGCACAAATATATGAGCATAAAAAAAGGCA
```

Fig. 9
Page 4 of 4

Sequence Range: 1 to 5285

```
            10          20          30          40          50
     *       *     *     *     *     *     *     *     *     *
  TG CAG AGC TCG GCT GGC CGC GGA GTC AGT CGA AGC TCT CCT CAG CGG CCG
     Q   S   S   A   G   R   G   V   S   R   S   S   P   Q   R   P>

60          70          80          90
     *       *     *     *     *     *     *     *     *
  GCT GAG CCA GCT GAG GCG GGA GAA AAA CAT GGC TCG GAC CTT GGA GGG
   A   E   P   A   E   A   G   E   K   H   G   S   D   L   G   G>

100         110         120         130         140
   *     *     *     *     *     *     *     *     *     *
  CGC GAA GGC TCG GGT TGC GGT GAA GAC CAA GAC TCC CGC AGC GTG AGG
   R   E   G   S   G   C   G   E   D   Q   D   S   R   S   V   R>

150         160         170         180         190
      *     *     *     *     *     *     *     *     *
  TCC TGG TAT TTT GGA AGC TAC AAG AAA AAA AGA TTA AGA GGT TTG TTC
   S   W   Y   F   G   S   Y   K   K   K   R   L   R   G   L   F>

200         210         220         230         240
   *     *     *     *     *     *     *     *     *     *
  TCT TTT GTG GAC ATG GCT CAG ATT TCC AAC AAC AGT GAA TTT AAA CAA
   S   F   V   D   M   A   Q   I   S   N   N   S   E   F   K   Q>

250         260         270         280         290
     *       *     *     *     *     *     *     *     *     *
  TGT TCA TCT TCA CAT CCA GAA CCA ATA AGA ACC AAA GAT GTG AAC AAA
   C   S   S   S   H   P   E   P   I   R   T   K   D   V   N   K>

300         310         320         330
     *       *     *     *     *     *     *     *     *
  GCA GAA GCG TTA CAG ATG GAA GCA GAA GCC TTA GCA AAA CTG CAG AAG
   A   E   A   L   Q   M   E   A   E   A   L   A   K   L   Q   K>

340         350         360         370         380
   *     *     *     *     *     *     *     *     *     *
  GAT AGA CAA ATG ACT GAC AGC CCA AGA GGC TTT GAG CTG TCT AGC AGC
   D   R   Q   M   T   D   S   P   R   G   F   E   L   S   S   S>

390         400         410         420         430
      *     *     *     *     *     *     *     *     *
  ACT AGA CAA AGA ACA CAA GGT TTT AAC AAA CAG GAT TAT GAT CTC ATG
   T   R   Q   R   T   Q   G   F   N   K   Q   D   Y   D   L   M>

440         450         460         470         480
   *     *     *     *     *     *     *     *     *     *
  GTG TTT CCT GAG TTG GAT TCC CAA AAA AGA GCA GTA GAT ATT GAT GTA
   V   F   P   E   L   D   S   Q   K   R   A   V   D   I   D   V>

490         500         510         520         530
     *       *     *     *     *     *     *     *     *     *
  GAA AAG CTC ACC CAG GCT GAA CTT GAG AAG ATA TTG CTG GAC GAC AAT
   E   K   L   T   Q   A   E   L   E   K   I   L   L   D   D   N>

540         550         560         570
     *       *     *     *     *     *     *     *     *
  TTT GAA ACT AGA AAA CCT CCT GCA TTG CCA GTT ACT CCT GTT CTG AGC
   F   E   T   R   K   P   P   A   L   P   V   T   P   V   L   S>
```

Fig. 10
Page 1 of 9

```
        580              590              600              610              620
         *        *       *        *       *        *       *        *       *        *
        CCT TCG TTC TCA ACA CAG CTG TAT CTT AGA CCT AGT GGT CAA AGA GGC
         P   S   F   S   T   Q   L   Y   L   R   P   S   G   Q   R   G>

630              640              650              660              670
                  *        *       *        *       *        *       *        *       *
                 CAG TGG CCC CCT GGA TTA TGC GGG CCT TCC ACG TAC ACT TTA CCT TCT
                  Q   W   P   P   G   L   C   G   P   S   T   Y   T   L   P   S>

680              690              700              710              720
             *        *       *        *       *        *       *        *       *
            ACT TAT CCT TCA GCA TAC AGT AAA CAG GCC ACA TTC CAG AAT GGC TTC
             T   Y   P   S   A   Y   S   K   Q   A   T   F   Q   N   G   F>

730              740              750              760              770
                     *        *       *        *       *        *       *        *       *
                    AGT CCA AGG ATG CCC ACT TTT CCA TCA ACA GAG TCT GTA TAT TTA AGA
                     S   P   R   M   P   T   F   P   S   T   E   S   V   Y   L   R>

780              790              800              810
                          *        *       *        *       *        *       *        *       *
                         CTT CCT GGA CAG TCT CCA TAT TTT TCA TAT CCT TTG ACA CCT GCC ACA
                          L   P   G   Q   S   P   Y   F   S   Y   P   L   T   P   A   T>

820              830              840              850              860
         *        *       *        *       *        *       *        *       *
        CCA TTT CAT CCA CAA GGA AGT TTA CCA GTC TAT CGG CCA CTA GTC AGT
         P   F   H   P   Q   G   S   L   P   V   Y   R   P   L   V   S>

870              880              890              900              910
             *        *       *        *       *        *       *        *       *
            CCT GAC ATG GCA AAA CTA TTT GAA AAA ATA GCA AGT ACC TCA GAA TTT
             P   D   M   A   K   L   F   E   K   I   A   S   T   S   E   F>

920              930              940              950              960
                 *        *       *        *       *        *       *        *       *
                TTA AAA AAT GGG AAA GCA AGG ACT GAT TTG GAG ATA GCA AAC TCG AAA
                 L   K   N   G   K   A   R   T   D   L   E   I   A   N   S   K>

970              980              990             1000             1010
                         *        *       *        *       *        *       *        *       *
                        GCT TCA GTC TGC AAT CTA CAG ATA TCT CCA AAG TCT GAA GAC ATC AAT
                         A   S   V   C   N   L   Q   I   S   P   K   S   E   D   I   N>

1020             1030             1040             1050
                             *       *        *       *        *       *        *       *
                            AAG TTT GAT TGG TTA GAC TTG GAT CCT TGG GAT GCT GTT CTT CTT GAA
                             K   F   D   W   L   D   L   D   P   W   D   A   V   L   L   E>

1060             1070             1080             1090             1100
          *       *        *       *        *       *        *       *        *
         GAG AGA TCG CCA AGT TGT CAC CTA GAA AGA AAG GTG AAT GGA AAA TCC
          E   R   S   P   S   C   H   L   E   R   K   V   N   G   K   S>

1110             1120             1130             1140             1150
             *       *        *       *        *       *        *       *        *
            CTT TCT GGG GCA ACT GTA ACA AGA AGC CAG TCT TTA ATC ATT CGG ACA
             L   S   G   A   T   V   T   R   S   Q   S   L   I   I   R   T>

1160             1170             1180             1190             1200
             *       *        *       *        *       *        *       *        *
```

Fig. 10
Page 2 of 9

```
             GCT CAA TTT ACA AAA GCC CAG GGC CAA GTA TCT CAG AAA GAC CCA AAT
              A   Q   F   T   K   A   Q   G   Q   V   S   Q   K   D   P   N>

1210          1220          1230          1240          1250
                     *             *             *             *             *
             GGG ACC AGT AGT TTG CCA ACT GGA AGT TCT CTT CTA CAA GAA TTT GAA
              G   T   S   S   L   P   T   G   S   S   L   L   Q   E   F   E>

1260          1270          1280          1290
                     *             *             *             *
             GTA CAG AAT GAC GAG GTG GCA GCT TTT TGT CAA TCC ATT ATG AAA TTG
              V   Q   N   D   E   V   A   A   F   C   Q   S   I   M   K   L>

1300          1310          1320          1330          1340
        *             *             *             *             *
       AAG ACC AAA TTT CCA TAT ACT GAT CAC TGC ACA AAT CCA GGC TAT TTG
        K   T   K   F   P   Y   T   D   H   C   T   N   P   G   Y   L>

1350          1360          1370          1380          1390
              *             *             *             *             *
             TTA AGT CCA GTG ACA GTG CAA AGA AAC ATG TGT GGG GAG AAT GCC AGT
              L   S   P   V   T   V   Q   R   N   M   C   G   E   N   A   S>

1400          1410          1420          1430          1440
                     *             *             *             *             *
             GTG AAG GTC TCC ATT GAA ATT GAA GGG CTT CAA CTA CCA GTT ACT TTT
              V   K   V   S   I   E   I   E   G   L   Q   L   P   V   T   F>

1450          1460          1470          1480          1490
                           *             *             *             *             *
             ACA TGT GAT GTG AGT TCT ACT GTA GAA ATA ATT ATA ATG CAA GCC CTT
              T   C   D   V   S   S   T   V   E   I   I   I   M   Q   A   L>

1500          1510          1520          1530
                     *             *             *             *
             TGC TGG GTA CAT GAT GAC TTG AAT CAA GTG GAT GTT GGC AGC TAC ATT
              C   W   V   H   D   D   L   N   Q   V   D   V   G   S   Y   I>

1540          1550          1560          1570          1580
        *             *             *             *             *
       CTG AAA GTT TGT GGT CAA GAG GAG GTT CTA CAG AAT AAT CAT TGC CTT
        L   K   V   C   G   Q   E   E   V   L   Q   N   N   H   C   L>

1590          1600          1610          1620          1630
              *             *             *             *             *
             GGA AGT CAC GAA CAT ATT CAA AAT TGT CGA AAA TGG GAC ACA GAG ATT
              G   S   H   E   H   I   Q   N   C   R   K   W   D   T   E   I>

1640          1650          1660          1670          1680
                     *             *             *             *             *
             AAA TTA CAG CTC TTG ACC TTG AGT GCA ATG TGC CAG AAT CTG GCT CGA
              K   L   Q   L   L   T   L   S   A   M   C   Q   N   L   A   R>

1690          1700          1710          1720          1730
                           *             *             *             *             *
             ACA GCA GAA GAT GAT GAA GCA CCT GTG GAT TTA AAC AAA TAC TTG TAT
              T   A   E   D   D   E   A   P   V   D   L   N   K   Y   L   Y>

1740          1750          1760          1770
                                 *             *             *             *
             CAA ATA GAA AAA CCT TAT AAA GAA GTC ATG ACA AGA CAC CCT GTT GAA
              Q   I   E   K   P   Y   K   E   V   M   T   R   H   P   V   E>
```

Fig. 10
Page 3 of 9

```
      1780            1790            1800            1810            1820
       *       *       *       *       *       *       *       *       *       *
      GAG     CTC     TTA     GAT     TCC     TAT     CAC     TAC     CAA     GTA     GAA     CTG     GCT     CTT     CAA     ACT
       E       L       L       D       S       Y       H       Y       Q       V       E       L       A       L       Q       T>

1830            1840            1850            1860            1870
       *       *       *       *       *       *       *       *       *       *
      GAA     AAC     CAG     CAC     CGA     GCT     GTT     GAT     CAA     GTG     ATT     AAA     GCA     GTA     AGA     AAA
       E       N       Q       H       R       A       V       D       Q       V       I       K       A       V       R       K>

1880            1890            1900            1910            1920
       *       *       *       *       *       *       *       *       *       *
      ATT     TGT     AGT     GCT     TTA     GAT     GGG     GTG     GAG     ACC     CCC     TCC     GTT     ACA     GAA     GCA
       I       C       S       A       L       D       G       V       E       T       P       S       V       T       E       A>

1930            1940            1950            1960            1970
       *       *       *       *       *       *       *       *       *       *
      GTG     AAG     AAG     TTA     AAG     CGA     GCA     GTT     AAC     CTT     CCA     AGG     AAT     AAA     AGT     GCT
       V       K       K       L       K       R       A       V       N       L       P       R       N       K       S       A>

1980            1990            2000            2010
       *       *       *       *       *       *       *       *       *
      GAT     GTG     ACT     TCA     TTA     TCT     GGA     AGT     GAC     ACA     AGG     AAG     AAC     TCA     ACT     AAG
       D       V       T       S       L       S       G       S       D       T       R       K       N       S       T       K>

2020            2030            2040            2050            2060
       *       *       *       *       *       *       *       *       *       *
      GGG     TCA     CTG     AAT     CCT     GAA     AAT     CCT     GTT     CAA     GTA     AGC     ATG     GAT     CAC     CTA
       G       S       L       N       P       E       N       P       V       Q       V       S       M       D       H       L>

2070            2080            2090            2100            2110
       *       *       *       *       *       *       *       *       *       *
      ACA     ACA     GCG     ATT     TAT     GAT     CTT     CTC     AGG     CTC     CAT     GCA     AAT     TCT     AGT     AGG
       T       T       A       I       Y       D       L       L       R       L       H       A       N       S       S       R>

2120            2130            2140            2150            2160
       *       *       *       *       *       *       *       *       *       *
      TGT     TCT     ACA     GGC     TGT     CCC     CGA     GGG     AGC     AGG     AAC     ATC     AAG     GAA     GCA     TGG
       C       S       T       G       C       P       R       G       S       R       N       I       K       E       A       W>

2170            2180            2190            2200            2210
       *       *       *       *       *       *       *       *       *       *
      ACT     GCA     ACG     GAG     CAG     CTC     CAG     TTC     ACT     GTC     TAT     GCC     GCA     CAC     GGA     ATT
       T       A       T       E       Q       L       Q       F       T       V       Y       A       A       H       G       I>

2220            2230            2240            2250
       *       *       *       *       *       *       *       *       *
      TCC     AGT     AAC     TGG     GTA     TCA     AAT     TAT     GAA     AAA     TAC     TAC     TTG     ATA     TGT     TCC
       S       S       N       W       V       S       N       Y       E       K       Y       Y       L       I       C       S>

2260            2270            2280            2290            2300
       *       *       *       *       *       *       *       *       *       *
      CTG     TCT     CAC     AAT     GGG     AAG     GAT     CTT     TTT     AAG     CCT     ATT     CAG     TCA     AAG     AAG
       L       S       H       N       G       K       D       L       F       K       P       I       Q       S       K       K>

2310            2320            2330            2340            2350
       *       *       *       *       *       *       *       *       *       *
      GTT     GGC     ACG     TAC     AAG     AAT     TTC     TTC     TAT     CTT     ATT     AAA     TGG     GAT     GAA     CTA
       V       G       T       Y       K       N       F       F       Y       L       I       K       W       D       E       L>

```
     *         *         *         *         *         *         *         *         *         *
ATC ATT TTT CCT ATC CAG ATA TCG CAG TTG CCA TTA GAA TCA GTT CTT
 I   I   F   P   I   Q   I   S   Q   L   P   L   E   S   V   L>
         2410      2420      2430      2440      2450
     *         *         *         *         *         *         *         *         *         *
CAT CTT ACT CTG TTT GGA GTT TTA AAT CAG AGC AGT GGA AGT TCC CCT
 H   L   T   L   F   G   V   L   N   Q   S   S   G   S   S   P>
         2460      2470      2480      2490
     *         *         *         *         *         *         *         *         *
GAT TCT AAT AAA CAG AGA AAG GGG CCA GAA GCT CTG GGC AAA GTT TCT
 D   S   N   K   Q   R   K   G   P   E   A   L   G   K   V   S>
2500      2510      2520      2530      2540
     *         *         *         *         *         *         *         *         *         *
TTA ACT CTA TTT GAT TTT AAA CGG TTT TTA ACA TGT GGA ACT AAA CTT
 L   T   L   F   D   F   K   R   F   L   T   C   G   T   K   L>
     2550      2560      2570      2580      2590
     *         *         *         *         *         *         *         *         *
CTC TAC CTT TGG ACT TCA TCA CAT ACA AAT TCT ATT CCT GGA GCA ATC
 L   Y   L   W   T   S   S   H   T   N   S   I   P   G   A   I>
         2600      2610      2620      2630      2640
     *         *         *         *         *         *         *         *         *         *
CCC AAA AAA AGC TAT GTC ATG GAA AGA ATT GTG CTA CAG GTT GAT TTT
 P   K   K   S   Y   V   M   E   R   I   V   L   Q   V   D   F>
         2650      2660      2670      2680      2690
     *         *         *         *         *         *         *         *         *         *
CCT TCT CCT GCG TTT GAC ATT ATT TAT ACA TCT CCT CAA ATT GAT AGA
 P   S   P   A   F   D   I   I   Y   T   S   P   Q   I   D   R>
         2700      2710      2720      2730
     *         *         *         *         *         *         *         *         *
AAC ATT ATA CAG CAA GAC AAG TTG GAA ACA CTG GAG AGT GAT ATA AAG
 N   I   I   Q   Q   D   K   L   E   T   L   E   S   D   I   K>
2740      2750      2760      2770      2780
     *         *         *         *         *         *         *         *         *         *
GGG AAA CTT CTG GAT ATT ATT CAC AGA GAT TCA TCA TTT GGA CTT TCT
 G   K   L   L   D   I   I   H   R   D   S   S   F   G   L   S>
     2790      2800      2810      2820      2830
     *         *         *         *         *         *         *         *         *
AAA GAA GAT AAG GTC TTT TTG TGG GAA AAC CGC TAT TAY TGC CTA AAA
 K   E   D   K   V   F   L   W   E   N   R   Y   Y   C   L   K>
         2840      2850      2860      2870      2880
     *         *         *         *         *         *         *         *         *         *
CAT CCA AAT TGT CTT CCG AAG ATA TTA GCA AGT GCT CCA AAC TGG AAG
 H   P   N   C   L   P   K   I   L   A   S   A   P   N   W   K>
         2890      2900      2910      2920      2930
     *         *         *         *         *         *         *         *         *         *
TGG GCT AAT CTT GCC AAA ACT TAC TCA TTG CTG CAT CAG TGG CCG CCA
 W   A   N   L   A   K   T   Y   S   L   L   H   Q   W   P   P>
         2940      2950      2960      2970
     *         *         *         *         *         *         *         *         *
TTG TGC CCA CTA GCT GCA TTG GAG CTC CTT GAT GCA AAA TTT GCT GAT
```

Fig. 10

```
              L   C   P   L   A   A   L   E   L   L   D   A   K   F   A   D>
     2980        2990        3000        3010        3020
       *           *           *           *           *
     CAG GGG GTG CGA TCG CTT GCT GTG AGC TGG ATG GAG GCC ATT AGT GAT
      Q   G   V   R   S   L   A   V   S   W   M   E   A   I   S   D>

3030        3040        3050        3060        3070
         *           *           *           *           *
     GAT GAG CTA GCA GAT CTG CTC CCA CAG TTC GTA CAG GCT TTG AAA TAT
      D   E   L   A   D   L   L   P   Q   F   V   Q   A   L   K   Y>

3080        3090        3100        3110        3120
         *           *           *           *           *
     GAA ATT TAT TTG AAT AGT TCA CTA GTG CGC TTC CTT CTG TCC AGG GCA
      E   I   Y   L   N   S   S   L   V   R   F   L   L   S   R   A>

3130        3140        3150        3160        3170
           *           *           *           *           *
     TTG GGA AAC ATC CAG ATA GCA CAC AGT TTG TAT TGG CTT CTC AAG GAT
      L   G   N   I   Q   I   A   H   S   L   Y   W   L   L   K   D>

3180        3190        3200        3210
                *           *           *           *
     GCT TTG CAT GAT ACA CAC TTT GGA AGC AGA TAT GAA CAT GTG TTG GGT
      A   L   H   D   T   H   F   G   S   R   Y   E   H   V   L   G>

3220        3230        3240        3250        3260
     *           *           *           *           *
     GCT CTC CTC TCT GTA GGA GGA AAA GGA CTC AGA GAA GAG CTT TCT AAG
      A   L   L   S   V   G   G   K   G   L   R   E   E   L   S   K>

3270        3280        3290        3300        3310
         *           *           *           *           *
     CAG ATG AAA CTT GTA CAG CTT TTA GGA GGA GTG GCA GAA AAA GTA AGG
      Q   M   K   L   V   Q   L   L   G   G   V   A   E   K   V   R>

3320        3330        3340        3350        3360
           *           *           *           *           *
     CAG GCT AGT GGA TCA ACA AGA CAG GTT GTC CTC CAA AAG AGT ATG GAA
      Q   A   S   G   S   T   R   Q   V   V   L   Q   K   S   M   E>

3370        3380        3390        3400        3410
           *           *           *           *           *
     CGG GTA CAG TCC TTT TTT CTG AGA AAT AAA TGC CGT CTT CCT CTC AAA
      R   V   Q   S   F   F   L   R   N   K   C   R   L   P   L   K>

3420        3430        3440        3450
                *           *           *           *
     CCA AGT CTA GTG GCA AAA GAA CTA AAT ATT AAG TCA TGT TCG TTC TTC
      P   S   L   V   A   K   E   L   N   I   K   S   C   S   F   F>

3460        3470        3480        3490        3500
     *           *           *           *           *
     AGT TCT AAT GCT ATG CCT CTG AAA GTC ACA ATG GTG AAT GCT GAC CCT
      S   S   N   A   M   P   L   K   V   T   M   V   N   A   D   P>

3510        3520        3530        3540        3550
         *           *           *           *           *
     CTG GGG GAA GAA ATT AAT GTC ATG TTT AAG GTT GGT GAA GAT CTT CGG
      L   G   E   E   I   N   V   M   F   K   V   G   E   D   L   R>
```

Fig. 10

```
       3560           3570           3580           3590           3600
  *      *       *      *      *      *       *      *      *       *
CAA GAT ATG TTA GCT TTA CAG ATG ATA AAG ATT ATG GAT AAG ATC TGG
 Q   D   M   L   A   L   Q   M   I   K   I   M   D   K   I   W>

3610           3620           3630           3640           3650
  *      *       *      *      *      *       *      *      *       *
CTT AAA GAG GGA CTG GAT CTG AGG ATG GTG ATA TTC AGA TGC CTG TCA
 L   K   E   G   L   D   L   R   M   V   I   F   R   C   L   S>

3660           3670           3680           3690
  *      *       *      *      *      *       *      *
ACT GGC CGA GAT CGA GGC ATG GTG GAG CTA GTT CCT GCT TCA GAT ACC
 T   G   R   D   R   G   M   V   E   L   V   P   A   S   D   T>

3700           3710           3720           3730           3740
  *      *       *      *      *      *       *      *      *
CTC AGG AAA ATC CAA GTG GAA TAT GGT GTA ACA GGA TCC TTT AAA GAT
 L   R   K   I   Q   V   E   Y   G   V   T   G   S   F   K   D>

3750           3760           3770           3780           3790
  *      *       *      *      *      *       *      *      *
AAA CCA CTT GCT GAG TGG CTG AGG AAA TAC AAT CCT TCT GAA GAA GAA
 K   P   L   A   E   W   L   R   K   Y   N   P   S   E   E   E>

3800           3810           3820           3830           3840
  *      *       *      *      *      *       *      *      *       *
TAT GAA AAG GCT TCT GAG AAC TTT ATC TAC TCT TGT GCT GGG TGC TGT
 Y   E   K   A   S   E   N   F   I   Y   S   C   A   G   C   C>

3850           3860           3870           3880           3890
  *      *       *      *      *      *       *      *      *       *
GTA GCC ACC TAT GTT TTA GGC ATT TGT GAT CGG CAC AAT GAC AAT ATA
 V   A   T   Y   V   L   G   I   C   D   R   H   N   D   N   I>

3900           3910           3920           3930
        *      *       *      *      *      *       *      *
ATG CTT CGA AGC ACA GGA CAC ATG TTC CAC ATT GAC TTT GGA AAG TTT
 M   L   R   S   T   G   H   M   F   H   I   D   F   G   K   F>

3940           3950           3960           3970           3980
  *      *       *      *      *      *       *      *      *
TTG GGC CAT GCA CAG ATG TTT GGT AGC TTC AAA AGG GAC CGA GCT CCT
 L   G   H   A   Q   M   F   G   S   F   K   R   D   R   A   P>

3990           4000           4010           4020           4030
  *      *       *      *      *      *       *      *      *
TTT GTG CTT ACC TCT GAC ATG GCG TAT GTC ATT AAT GGA GGT GAA AAG
 F   V   L   T   S   D   M   A   Y   V   I   N   G   G   E   K>

4040           4050           4060           4070           4080
  *      *       *      *      *      *       *      *      *
CCC ACC ATT CGT TTC CAG TTG TTT GTG GAC CTC TGC TGT CAA GCC TAC
 P   T   I   R   F   Q   L   F   V   D   L   C   C   Q   A   Y>

4090           4100           4110           4120           4130
  *      *       *      *      *      *       *      *      *       *
AAC TTG ATA AGA AAG CAA ACA AAC CTC TTT CTT AAC CTT CTC TCA CTG
 N   L   I   R   K   Q   T   N   L   F   L   N   L   L   S   L>

Page 7 of 9

```
ATG ATT CCT TCA GGA TTG CCA GAA CTC ACA AGT ATT CAG GAT CTG AAA
 M   I   P   S   G   L   P   E   L   T   S   I   Q   D   L   K>

4180      4190      4200      4210      4220
  *    *    *    *    *    *    *    *    *    *
TAT GTT AGA GAT GCA CTT CAG CCC CAA ACT ACA GAT GCT GAA GCT ACT
 Y   V   R   D   A   L   Q   P   Q   T   T   D   A   E   A   T>

4230      4240      4250      4260      4270
   *    *    *    *    *    *    *    *    *    *
ATT TTC TTT ACT AGG CTG ATT GAG TCA AGT TTG GGA AGC ATT GCC ACA
 I   F   F   T   R   L   I   E   S   S   L   G   S   I   A   T>

4280      4290      4300      4310      4320
     *    *    *    *    *    *    *    *    *    *
AAG TTT AAT TTC TTC ATT CAT AAC CTT GCT CAG CTA CGT TTT TCT GGC
 K   F   N   F   F   I   H   N   L   A   Q   L   R   F   S   G>

4330      4340      4350      4360      4370
       *    *    *    *    *    *    *    *    *    *
CTT CCT TCT AAT GAT GAG CCC ATC CTT TCA TTC TCA CCG AAA ACA TAC
 L   P   S   N   D   E   P   I   L   S   F   S   P   K   T   Y>

4380      4390      4400      4410
         *    *    *    *    *    *    *    *    *    *
TCC TTT AGA CAA GAT GGC CGG ATC AAG GAA GTC TCT GTT TTC ACA TAT
 S   F   R   Q   D   G   R   I   K   E   V   S   V   F   T   Y>

4420      4430      4440      4450      4460
  *    *    *    *    *    *    *    *    *    *
CAT AAG AAA TAC AAC CCA GAT AAA CAC TAT ATT TAT GTG GTT CGA ATT
 H   K   K   Y   N   P   D   K   H   Y   I   Y   V   V   R   I>

4470      4480      4490      4500      4510
   *    *    *    *    *    *    *    *    *    *
CTA AGA GAA GGA CAC CTT GAA CCA TCA TTT GTA TTC CGG ACA TTT GAT
 L   R   E   G   H   L   E   P   S   F   V   F   R   T   F   D>

4520      4530      4540      4550      4560
     *    *    *    *    *    *    *    *    *    *
GAA TTT CAG GAA CTT CAC AAT AAG CTC AGT ATT ATT TTT CCT CTT TGG
 E   F   Q   E   L   H   N   K   L   S   I   I   F   P   L   W>

4570      4580      4590      4600      4610
       *    *    *    *    *    *    *    *    *    *
AAA TTA CCT GGC TTT CCT AAT AGG ATG GTT CTT GGA AGA ACA CAC ATA
 K   L   P   G   F   P   N   R   M   V   L   G   R   T   H   I>

4620      4630      4640      4650
         *    *    *    *    *    *    *    *    *
AAA GAT GTT GCA GCC AAG AGG AAA ATT GAA TTA AAC AGT TAT TTA CAG
 K   D   V   A   A   K   R   K   I   E   L   N   S   Y   L   Q>

4660      4670      4680      4690      4700
  *    *    *    *    *    *    *    *    *    *
AGT TTG ATG AAT GCA TCA ACA GAT GTA GCA GAG TGT GAT CTT GTT TGT
 S   L   M   N   A   S   T   D   V   A   E   C   D   L   V   C>

4710      4720      4730      4740      4750
   *    *    *    *    *    *    *    *    *    *
ACT TTT TTC CAC CCT TTA CTT CGT GAT GAG AAA GCT GAA GGA ATA GCT
 T   F   F   H   P   L   L   R   D   E   K   A   E   G   I   A>
```

Fig. 10

```
        4760            4770            4780            4790            4800
   *      *       *      *       *      *       *      *       *      *
 AGG    TCT    GCA    GGT    GCA    GTT    CCC    TTC    AGC    CCA    ACT    CTG    GGC    CAA    ATA    GGA
  R      S      A      G      A      V      P      F      S      P      T      L      G      Q      I      G>

4810            4820            4830            4840            4850
    *      *       *      *       *      *       *      *       *      *
 GGA    GCA    GTG    AAG    TTA    TCT    GTT    TCT    TAC    CGA    AAT    GGC    ACC    CTC    TTC    ATC
  G      A      V      K      L      S      V      S      Y      R      N      G      T      L      F      I>

4860            4870            4880            4890
    *      *       *      *       *      *       *      *       *
 ATG    GTG    ATG    CAC    ATC    AAA    GAT    CTT    GTG    ACT    GAA    GAT    GGG    GCT    GAC    CCA
  M      V      M      H      I      K      D      L      V      T      E      D      G      A      D      P>

4900           4910            4920            4930            4940
   *      *       *      *       *      *       *      *       *      *
 AAT    CCC    TAT    GTC    AAA    ACA    TAC    CTG    CTT    CCA    GAT    ACC    CAC    AAA    ACG    TCA
  N      P      Y      V      K      T      Y      L      L      P      D      T      H      K      T      S>

4950           4960            4970            4980            4990
   *      *       *      *       *      *       *      *       *
 AAA    CGT    AAA    ACC    AAA    ATT    TCA    CGT    AAA    ACT    AGG    AAC    CCA    ACA    TTC    AAT
  K      R      K      T      K      I      S      R      K      T      R      N      P      T      F      N>

5000            5010            5020            5030            5040
   *      *       *      *       *      *       *      *       *      *
 GAA    ATG    CTT    GTA    TAT    AGT    GGA    TAC    AGC    AAA    GAA    ACT    CTG    AGG    CAG    AGA
  E      M      L      V      Y      S      G      Y      S      K      E      T      L      R      Q      R>

5050            5060            5070            5080            5090
    *      *       *      *       *      *       *      *       *      *
 GAA    CTT    CAA    CTG    AGT    GTA    CTC    AGT    GCA    GAA    TCA    CTG    CGG    GAG    AAT    TTC
  E      L      Q      L      S      V      L      S      A      E      S      L      R      E      N      F>

5100            5110            5120            5130
    *      *       *      *       *      *       *      *       *
 TTC    TTG    GGT    GGA    ATA    ACC    CTG    CCA    CTG    AAA    GAT    TTC    AAC    TTG    AGC    AAA
  F      L      G      G      I      T      L      P      L      K      D      F      N      L      S      K>

5140           5150            5160            5170            5180
   *      *       *      *       *      *       *      *       *      *
 GAG    ACA    GTT    AAG    TGG    TAT    CAG    CTG    ACT    GCG    GCA    ACG    TAT    CTA    TAA    ACT
  E      T      V      K      W      Y      Q      L      T      A      A      T      Y      L      (*)    T>

5190            5200            5210            5220            5230
   *      *       *      *       *      *       *      *       *      *
 TCC    GAC    TTC    TGA    GCT    TTG    GAA    ACA    AGG    AGT    TAT    AAA    TGT    GTG    CGC    ATG
  S      D      F      *      A      L      E      T      R      S      Y      K      C      V      R      M>

5240            5250            5260            5270            5280
   *      *       *      *       *      *       *      *       *      *
 CGC    ACA    TAC    ACA    CAC    TTG    GGA    ACT    TTG    TAT    AAT    TTC    ATA    CTT    TGG    CAG
  R      T      Y      T      H      L      G      T      L      Y      N      F      I      L      W      Q>

*
 CCC
  P>
```

Fig. 10

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:1:

GANGAYHTNM GNCARGA                                    17

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO:2:

CCRAARTCDA TRTGDAW                                                                                17

(2) INFORMATION FOR SEQ ID NO:3:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (probe)

(ix) FEATURE:
             (A) NAME/KEY: modified_base
             (B) LOCATION: one-of(5,6,9,12,17,20)
             (D) OTHER INFORMATION: /note= "inosine"

(xi) SEQUENCE DESCRIPTION: SEQ ID NO:3:

AARRNNGGNG ANGAYTNMGN CARGA                                                                       25

(2) INFORMATION FOR SEQ ID NO:4:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: DNA (probe)

(ix) FEATURE:
             (A) NAME/KEY: modified_base
             (B) LOCATION: one-of(3,12,18,21)
             (D) OTHER INFORMATION: /note= "inosine"

(xi) SEQUENCE DESCRIPTION: SEQ ID NO:4:

TVNCCRAART CNRYRTGNAW NA                                                                          22

(2) INFORMATION FOR SEQ ID NO:5:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Region
             (B) LOCATION: one-of(1)
             (D) OTHER INFORMATION: /note= "Xaa is Asp or Glu."

(ix) FEATURE:
             (A) NAME/KEY: Region
             (B) LOCATION: one-of(3)
             (D) OTHER INFORMATION: /note= "Xaa is Leu or Ile."

(xi) SEQUENCE DESCRIPTION: SEQ ID NO:5:

Xaa Asp Xaa Arg Gln Asp
1               5

(2) INFORMATION FOR SEQ ID NO:6:

```
    (i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(1)
        (D) OTHER INFORMATION: /note= "Xaa is Phe or Ile."

(xi) SEQUENCE DESCRIPTION: SEQ ID NO:6:

Xaa His Ile Asp Phe Gly
1               5

(2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Cys Arg Gln Asp Phe Leu Ser Gln Pro Ser Thr Ser Ser Ser Gln Tyr
1               5                  10                  15

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Cys Gln Gly Gln Val Ser Gln Lys Asp Pro Asn Gly Thr Ser Ser
1               5                  10                  15

(2) INFORMATION FOR SEQ ID NO:9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:9:

CCCCGGGTCA GCGGCCGCCG TTCCTGGACA CCGCGCCCAG                          40

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:10:

TTAGACGAGA CTAGTATGTC AAATCAAGCG                                     30
```

(2) INFORMATION FOR SEQ ID NO:11:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:11:

```
GTGGGACCTG ATGCCGAATC TTTACCGGCT ATCTTTAGGT GCGGA          45
```

(2) INFORMATION FOR SEQ ID NO:12:

(i) SEQUENCE CHARACTERISTICS:
        (A) LENGTH: 1876 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Met Ser Asn Gln Ala His Ile Asp Tyr Asp Lys Gln Phe Gln Asp Asp
1               5                   10                  15

Leu Ala Lys Ala Thr Ala Leu Ser Leu Glu Gln His Ala Leu Asp Asp
            20                  25                  30

Tyr Arg Arg Asn Lys Lys Tyr Gly Ser Gly Tyr Gln Ser Ser Thr
        35                  40                  45

Val Ala Gly Arg Asp Tyr Gln Ala Ala Gln Arg Ser Gln Ser Leu His
    50                  55                  60

Gln Pro Arg Arg His Ser Glu Val His Gln Val Ala Ile Ser Pro Glu
65                  70                  75                  80

Asn Ala Glu Arg Ser Arg Thr Pro Pro Ala Gln Gly Thr Asp Asn Asp
                85                  90                  95

Leu Ile Cys Phe Ala Ser Pro Thr Ser Lys Gln Pro Glu Ser Ser Ser
            100                 105                 110

Pro Phe Gly Lys Leu Ile Glu Asp Leu Gln Arg Met Gln Pro Thr Asn
        115                 120                 125

Pro Gln Ser Ala Leu Val Pro Met Gly Pro Val Ala Ser Ala Ser Ile
    130                 135                 140

Pro Pro Gln Tyr Gly Phe Pro Pro His Gln Gln Arg Pro Thr Ala Ala
145                 150                 155                 160

Gln Pro Thr Pro Tyr Gly Met Val Ala Gly Val Val Gly Gly Pro
                165                 170                 175

Ala Tyr Gly Asp Leu Gln Leu Val Pro Tyr Gln Pro Ala Ala Gln Gln
            180                 185                 190

Gln Arg Pro Leu Asn Ser Glu Glu Leu Gln Arg Leu Tyr Ser Met Pro
        195                 200                 205

Ala Gln Met Ala Val Val Pro Val Gln Pro Asn Ala Tyr Met Tyr
    210                 215                 220

Tyr Pro Gly Ala Val Val Thr Pro Tyr Thr Ala Pro Ile Val Pro Gly
225                 230                 235                 240

Ser Ala Ala Phe Met Pro Pro Gln Tyr Pro Ala Gln Gly Tyr Gly Phe
                245                 250                 255

Gly Gly Ala Tyr Thr His Met Asp Leu Arg Arg Pro Gln Ser Gln Pro
            260                 265                 270
```

-continued

```
Ala Pro Gln Gln Thr Ala Pro Thr Thr Ser His His His Ser Gln Pro
            275                 280                 285

Ser Asn His Ser Thr Ser Ser Pro Ala Glu Ala Asn Gly Val Ala Phe
            290                 295                 300

Pro Ala Arg Arg Gln Val Pro Ser Thr Val Gly Val Ser Ser Ser Ser
305                 310                 315                 320

His Thr Gly Asn Asn Gly His Ser Ser Val Pro Arg Arg Gly Asn Asp
                325                 330                 335

Leu Ile Asp Leu Asn His Glu Asp Tyr Ser Arg Val Ser Val Leu Glu
            340                 345                 350

Ala Phe Asp Pro Leu Leu Asn Asp Asn Thr Gly Asn Asp Thr Ala Ser
            355                 360                 365

Asp Ser Thr Ser Tyr Tyr Ala Glu Tyr Asp Pro Phe Asp Phe Leu Tyr
            370                 375                 380

Ser Gly Asp Ala Ala Thr Gln Tyr Ser Asp Pro Met Tyr Glu Ala Val
385                 390                 395                 400

Asn Arg Trp Asp Lys Thr Val Ala Thr Val Ser Pro Asn Val Gly Leu
                405                 410                 415

Ile Gly Trp Arg Gln Asp Phe Leu Ser Gln Pro Ser Thr Ser Ser Ser
            420                 425                 430

Gln Tyr Gly Val Ala Pro Pro Glu Glu Ser Leu Lys Leu Ala Glu Asn
            435                 440                 445

Gly Ser Gly Thr Ile Ser Pro Pro Pro Leu Pro Pro Arg Asn Gln
            450                 455                 460

Gln Cys Tyr Glu Ser Asn Gln Ala Ala Met Pro Val Ser Arg Pro Pro
465                 470                 475                 480

Gln Ser Ser Val Leu Thr Asp Ser Tyr Thr Ser Ser Ile Pro Ala Asn
                485                 490                 495

Val Val Leu Asp Arg Arg Lys Thr Cys Thr Arg Leu Tyr Glu Leu Ile
            500                 505                 510

Ser Asp Gln Arg Thr Asp Asp Pro Glu Leu Leu Glu Phe Tyr His Met
            515                 520                 525

Val Lys Glu Val Arg Ala Arg Tyr Pro His Asp Asp Ala Pro Thr Asn
            530                 535                 540

Val Gly His Val Val Ala Ala Glu Phe Asn Tyr His Tyr Met Met Asp
545                 550                 555                 560

Thr Ser Ile Lys Val Ile Val His Pro Ala Leu Asn Thr Leu Gln Ser
                565                 570                 575

Thr Val Leu Ala Ala Ser Met Gly Lys Glu Gln Val Lys Gly Tyr Gly
            580                 585                 590

Met Pro Val Thr Phe Thr Cys Asp Ile Asp Ser Val Val Ala Gln Val
            595                 600                 605

Val Ala Gln Ala Leu Ala Ser Leu Glu Gly Gln Val Lys Gly Thr Val
            610                 615                 620

Thr Asp Tyr Ala Val Lys Pro Ile Gly Leu Leu Glu Trp Leu Ala Pro
625                 630                 635                 640

Thr Ser Arg Leu Ser Gln Leu Glu Cys Val His Asn Ser Phe Gln Leu
                645                 650                 655

Glu Lys Asp Val His Leu Gly Leu Cys Leu Ser Thr Ala Ala Asn Met
            660                 665                 670

Gln Ala Ile Ala Arg Thr Glu Arg Asp Glu His Asp Ala Asp Leu
            675                 680                 685
```

-continued

```
Leu Pro Glu His Leu Leu Pro Asn Glu Val Val Gln Ile Val Thr Tyr
    690                 695                 700
Asp Asn Met Met Ile Leu Ile Glu Thr Leu Glu Met Glu Ile Asp Lys
705                 710                 715                 720
Leu Glu Ser Ala Ala Asp Gly Val Pro Gly Arg Ser Val Val Ser Cys
                725                 730                 735
Ser Gly Val Val Gln Ala Val Lys Ala Ile Cys Ala Leu Leu Gly Ser
                740                 745                 750
Ile Asp Thr Met Glu Ile Ala Arg Cys Val Ala Asp Leu Lys Arg Ile
            755                 760                 765
Cys Glu Val Glu Gln Lys Lys Tyr Ser Thr Gly Ala Ser Asn Pro Glu
    770                 775                 780
Ile Val Ser Asp Tyr Gly Asp Tyr Ala Gln Val Val Leu Arg Pro Arg
785                 790                 795                 800
Ser Met Leu Glu Gln Ile Lys Val Lys Cys Asn Glu Leu Arg Asp Ala
                805                 810                 815
Val Gln Glu Leu Val Glu Leu Tyr Ala Asn Val Phe Arg Val Ala Phe
                820                 825                 830
Ser Val Lys Thr Pro Asp Tyr Ser Thr Thr Pro Ile Pro Ile Ser Cys
            835                 840                 845
Val Ser Lys Pro Ile Val Val Cys Ile Ser Cys Leu His Arg Pro Leu
    850                 855                 860
Pro Asn Trp Lys Phe Asp Asp Tyr Ser Leu Cys Val Gln Ile Val Tyr
865                 870                 875                 880
Gly Thr Arg Leu Leu Ser Lys Pro Asn Val Leu Thr Cys Ser Asn Asp
                885                 890                 895
Thr Ser Gly Gly Leu Phe Pro Arg Leu Asn Phe Ser Ala Trp Leu Thr
                900                 905                 910
Phe Asp Gln His Pro Ile Cys Thr Leu Pro Arg Glu Ala Arg Leu Thr
            915                 920                 925
Phe Val Leu Tyr Gly Lys Gln Ala Ala Ser Glu Gly Glu Pro Asn Ala
    930                 935                 940
Asp Gln Asn Gly Glu Arg Arg Gln Val Thr Thr Glu Leu Gly Trp Cys
945                 950                 955                 960
Ser Ile Gln Leu Phe Asp Phe Lys Arg Val Met Ile Cys Gly Pro Tyr
                965                 970                 975
Leu Leu Ser Leu Trp Pro Pro Met Thr Asp Lys Met Leu Gly Pro Ala
                980                 985                 990
Pro Ala Arg Gly Cys His Pro Gln Pro Asp Phe Cys Pro Val Leu Ser
            995                 1000                1005
Ile Glu Val Pro Pro Tyr Gly Gly Arg Ile Glu Phe Pro Glu His Gln
    1010                1015                1020
Glu Val Pro Lys Pro Ala Pro His Tyr Asp Phe Ala Ser Leu Asp Ala
1025                1030                1035                1040
Asn Leu Gln Glu Glu Leu Leu Asp Thr Ala Glu Leu Gly Tyr Thr Gly
                1045                1050                1055
Ala Thr Glu Arg Arg Glu Val Phe Trp Glu Lys Arg Leu Tyr Leu Gln
                1060                1065                1070
Ser Tyr Pro Asn Ala Leu Pro Lys Val Leu His Ala Ala His Ser Trp
            1075                1080                1085
Asp Tyr Ala Asn Leu Ile Asp Leu His Ala Leu Leu His Ser Trp Ala
    1090                1095                1100
Pro Leu Ser Pro Leu Gln Ser Leu Glu Leu Leu Leu Pro Arg Tyr Pro
```

-continued

```
               1105                1110                1115                1120

Asp Ala Lys Val Arg Glu Lys Ala Val Glu Trp Ile Ser Lys Met Pro
                1125                1130                1135

Asn Asp Gln Leu Val Asp Phe Leu Pro Gln Leu Val Gln Ser Leu Lys
                1140                1145                1150

His Asp Thr Tyr Glu Gly Ser Ala Met Ala Arg Phe Leu Leu Ser Lys
                1155                1160                1165

Cys Leu Glu Ser Pro Arg Phe Ala His His Met Tyr Trp Leu Leu Val
                1170                1175                1180

His Ser Leu Pro Asp Asp Pro His Asn Ser Ile Gly Ala Ala Met Val
1185                1190                1195                1200

Asp Gln Glu Tyr Asp Glu Ser Gln Val Thr Gln Val Arg Tyr Tyr Arg
                1205                1210                1215

Arg Asn Lys Met Met Leu Arg Ala Leu Met Ala Ile Cys Gly Glu Lys
                1220                1225                1230

Met Leu Gln Arg Phe Met Tyr Gln His Arg Met Cys Gln Lys Leu Thr
                1235                1240                1245

Thr Ile Ala Glu Ser Val Lys Glu Ala Lys Glu Ser Met Arg Gln Lys
                1250                1255                1260

Ser Leu Ala Ala Gly Met Asp Glu Val His Gln Asp Leu Leu Glu Gln
1265                1270                1275                1280

Pro Thr Cys Leu Pro Leu Gly Pro Glu Leu Glu Val Thr Gly Val Ser
                1285                1290                1295

Val Arg Asn Cys Ser Tyr Phe Asn Ser Asn Thr Leu Pro Leu Lys Ile
                1300                1305                1310

Asn Phe Val Gly Pro Asp Ala Glu Ser Leu Pro Ala Ile Phe Lys Cys
                1315                1320                1325

Gly Asp Asp Leu Gln Gln Asp Gln Leu Thr Ile Gln Leu Ile Arg Ile
                1330                1335                1340

Met Asn Lys Met Trp Leu Ala Glu Arg Leu Asp Leu Lys Met Val Thr
1345                1350                1355                1360

Phe Asn Cys Val Pro Thr Gly Tyr Lys Ser Gly Met Ile Glu Leu Val
                1365                1370                1375

Ser Glu Ala Glu Thr Leu Arg Lys Ile Gln Val Glu Cys Gly Leu Thr
                1380                1385                1390

Gly Ser Phe Lys Asp Arg Pro Ile Ala Glu Trp Leu Gly Lys Gln Asn
                1395                1400                1405

Pro Ser Pro Leu Glu Tyr Gln Ser Ala Val Arg Asn Phe Thr Leu Ser
                1410                1415                1420

Cys Ala Gly Tyr Ser Val Ala Thr Tyr Val Leu Gly Ile Cys Asp Arg
1425                1430                1435                1440

His Asn Asp Asn Ile Met Leu Lys Thr Ser Gly His Leu Phe His Ile
                1445                1450                1455

Asp Phe Gly Lys Phe Leu Gly Asp Ala Gln Met Phe Gly Asn Phe Lys
                1460                1465                1470

Arg Asp Arg Thr Pro Phe Val Leu Thr Ser Asp Met Ala Tyr Val Ile
                1475                1480                1485

Asn Gly Gly Asp Lys Pro Ser Thr Asp Phe His Tyr Phe Val Asp Leu
                1490                1495                1500

Cys Cys Arg Ala Phe Asn Ile Val Arg Lys Asn Ala Asp Leu Leu Leu
1505                1510                1515                1520

His Thr Leu Ala His Met Ala Thr Ala Gly Met Pro Gly Val Asn Ser
                1525                1530                1535
```

Asn Ala Val Gln Tyr Val Arg Arg Ala Leu Leu Pro Ser Gln Ser Asn
        1540                1545                1550

Pro Glu Ala Ala Ala Thr Phe Ala Lys Met Ile Gln Ser Ser Leu Lys
        1555                1560                1565

Ser Trp Phe Thr Gln Phe Asn Phe Leu His Asn Leu Ala Gln Met
        1570                1575                1580

Arg Phe Thr Pro Asp Glu Gly Ser Gly Glu Leu Leu Ser Phe Val Pro
1585                1590                1595                1600

Arg Lys Tyr Thr Met Gln Gln Asp Gly Arg Leu Lys Ile Val Lys Val
                1605                1610                1615

Val Cys Phe Gln Lys His Tyr Ser Met Glu Lys Glu Tyr Met Tyr Ile
                1620                1625                1630

Leu Glu Val Thr Arg His Gly Gln Pro Asp Pro Thr His Leu Phe Arg
                1635                1640                1645

Ser Tyr Arg Glu Phe Thr Glu Phe His Gln Lys Leu Cys Met His Phe
        1650                1655                1660

Pro Leu Val Lys Leu His Ser Leu Pro Ala Gly Val His Val Gly Arg
1665                1670                1675                1680

Ser Asn Lys Ser Val Ala Glu Lys Arg Leu Pro Leu Ile Gln Arg Phe
                1685                1690                1695

Leu Lys Ser Leu Phe Asp Ala Ser Glu Glu Ile Ile Ala His Ser Glu
                1700                1705                1710

Leu Val Tyr Thr Phe Phe His Pro Leu Leu Arg Asp Gln Gln Glu Ala
                1715                1720                1725

Lys Leu Gly Met Pro Lys Ile Lys Glu Val Lys Gln Gln Pro Ser Arg
        1730                1735                1740

Asp Asn Pro His Glu Ile Gly Gln Ile Arg Leu Ser Leu Gln Tyr Gln
1745                1750                1755                1760

Arg Gly Val Leu Thr Val Met Ile His Ala Lys Gly Leu Pro Met
                1765                1770                1775

Leu Gln Gly Gly Gln Glu Pro Asn Thr Tyr Val Lys Cys Tyr Leu Lys
        1780                1785                1790

Pro Asp Pro Lys Lys Glu Thr Lys Arg Lys Thr Lys Val Val Arg Lys
        1795                1800                1805

Thr Cys Val Pro Ser Phe Met Glu Thr Leu Glu Tyr Arg Met Pro Leu
        1810                1815                1820

Asn Ile Ile Gln Glu Arg Arg Leu Gln Val Thr Val Trp Ser His Asp
1825                1830                1835                1840

Thr Leu Gln Glu Asn Glu Leu Leu Gly Gly Phe Asp Met Asp Leu Ser
                1845                1850                1855

Lys Tyr Asp Leu Arg Gln Glu Leu Val Asp Trp Tyr Arg Leu Gly Ala
                1860                1865                1870

Val Ser Arg Asn
        1875

(2) INFORMATION FOR SEQ ID NO:13:

(i) SEQUENCE CHARACTERISTICS:
        (A) LENGTH: 1658 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

-continued

```
Met Ala Gln Ile Ser Asn Asn Ser Glu Phe Lys Gln Cys Ser Ser Ser
1               5                   10                  15

His Pro Glu Pro Ile Arg Thr Lys Asp Val Asn Lys Ala Glu Ala Leu
            20                  25                  30

Gln Met Glu Ala Glu Ala Leu Ala Lys Leu Gln Lys Asp Arg Gln Met
            35                  40                  45

Thr Asp Ser Pro Arg Gly Phe Glu Leu Ser Ser Thr Arg Gln Arg
        50                  55              60

Thr Gln Gly Phe Asn Lys Gln Asp Tyr Asp Leu Met Val Phe Pro Glu
65                  70                  75                  80

Leu Asp Ser Gln Lys Arg Ala Val Asp Ile Asp Val Glu Lys Leu Thr
                85                  90                  95

Gln Ala Glu Leu Glu Lys Ile Leu Leu Asp Asp Asn Phe Glu Thr Arg
            100                 105                 110

Lys Pro Pro Ala Leu Pro Val Thr Pro Val Leu Ser Pro Ser Phe Ser
            115                 120                 125

Thr Gln Leu Tyr Leu Arg Pro Ser Gly Gln Arg Gly Gln Trp Pro Pro
            130                 135                 140

Gly Leu Cys Gly Pro Ser Thr Tyr Thr Leu Pro Ser Thr Tyr Pro Ser
145                 150                 155                 160

Ala Tyr Ser Lys Gln Ala Thr Phe Gln Asn Gly Phe Ser Pro Arg Met
                165                 170                 175

Pro Thr Phe Pro Ser Thr Glu Ser Val Tyr Leu Arg Leu Pro Gly Gln
            180                 185                 190

Ser Pro Tyr Phe Ser Tyr Pro Leu Thr Pro Ala Thr Pro Phe His Pro
            195                 200                 205

Gln Gly Ser Leu Pro Val Tyr Arg Pro Leu Val Ser Pro Asp Met Ala
    210                 215                 220

Lys Leu Phe Glu Lys Ile Ala Ser Thr Ser Glu Phe Leu Lys Asn Gly
225                 230                 235                 240

Lys Ala Arg Thr Asp Leu Glu Ile Ala Asn Ser Lys Ala Ser Val Cys
                245                 250                 255

Asn Leu Gln Ile Ser Pro Lys Ser Glu Asp Ile Asn Lys Phe Asp Trp
            260                 265                 270

Leu Asp Leu Asp Pro Trp Asp Ala Val Leu Leu Glu Glu Arg Ser Pro
    275                 280                 285

Ser Cys His Leu Glu Arg Lys Val Asn Gly Lys Ser Leu Ser Gly Ala
    290                 295                 300

Thr Val Thr Arg Ser Gln Ser Leu Ile Ile Arg Thr Ala Gln Phe Thr
305                 310                 315                 320

Lys Ala Gln Gly Gln Val Ser Gln Lys Asp Pro Asn Gly Thr Ser Ser
                325                 330                 335

Leu Pro Thr Gly Ser Ser Leu Leu Gln Glu Phe Glu Val Gln Asn Asp
            340                 345                 350

Glu Val Ala Ala Phe Cys Gln Ser Ile Met Lys Leu Lys Thr Lys Phe
            355                 360                 365

Pro Tyr Thr Asp His Cys Thr Asn Pro Gly Tyr Leu Leu Ser Pro Val
    370                 375                 380

Thr Val Gln Arg Asn Met Cys Gly Glu Asn Ala Ser Val Lys Val Ser
385                 390                 395                 400

Ile Glu Ile Glu Gly Leu Gln Leu Pro Val Thr Phe Thr Cys Asp Val
                405                 410                 415
```

-continued

```
Ser Ser Thr Val Glu Ile Ile Met Gln Ala Leu Cys Trp Val His
            420                 425                 430

Asp Asp Leu Asn Gln Val Asp Val Gly Ser Tyr Ile Leu Lys Val Cys
            435                 440                 445

Gly Gln Glu Glu Val Leu Gln Asn Asn His Cys Leu Gly Ser His Glu
        450                 455                 460

His Ile Gln Asn Cys Arg Lys Trp Asp Thr Glu Ile Lys Leu Gln Leu
465                 470                 475                 480

Leu Thr Leu Ser Ala Met Cys Gln Asn Leu Ala Arg Thr Ala Glu Asp
                485                 490                 495

Asp Glu Ala Pro Val Asp Leu Asn Lys Tyr Leu Tyr Gln Ile Glu Lys
            500                 505                 510

Pro Tyr Lys Glu Val Met Ile Arg His Pro Val Glu Glu Leu Leu Asp
            515                 520                 525

Ser Tyr His Tyr Gln Val Glu Leu Ala Leu Gln Thr Glu Asn Gln His
    530                 535                 540

Arg Ala Val Asp Gln Val Ile Lys Ala Val Arg Lys Ile Cys Ser Ala
545                 550                 555                 560

Leu Asp Gly Val Glu Thr Pro Ser Val Thr Glu Ala Val Lys Lys Leu
                565                 570                 575

Lys Arg Ala Val Asn Leu Pro Arg Asn Lys Ser Ala Asp Val Thr Ser
            580                 585                 590

Leu Ser Gly Ser Asp Thr Arg Lys Asn Ser Thr Lys Gly Ser Leu Asn
        595                 600                 605

Pro Glu Asn Pro Val Gln Val Ser Met Asp His Leu Thr Thr Ala Ile
    610                 615                 620

Tyr Asp Leu Leu Arg Leu His Ala Asn Ser Ser Arg Cys Ser Thr Gly
625                 630                 635                 640

Cys Pro Arg Gly Ser Arg Asn Ile Lys Glu Ala Trp Thr Ala Thr Glu
                645                 650                 655

Gln Leu Gln Phe Thr Val Tyr Ala Ala His Gly Ile Ser Ser Asn Trp
            660                 665                 670

Val Ser Asn Tyr Glu Lys Tyr Tyr Leu Ile Cys Ser Leu Ser His Asn
            675                 680                 685

Gly Lys Asp Leu Phe Lys Pro Ile Gln Ser Lys Val Gly Thr Tyr
        690                 695                 700

Lys Asn Phe Phe Tyr Leu Ile Lys Trp Asp Glu Leu Ile Ile Phe Pro
705                 710                 715                 720

Ile Gln Ile Ser Gln Leu Pro Leu Glu Ser Val Leu His Leu Thr Leu
                725                 730                 735

Phe Gly Val Leu Asn Gln Ser Ser Gly Ser Ser Pro Asp Ser Asn Lys
            740                 745                 750

Gln Arg Lys Gly Pro Glu Ala Leu Gly Lys Val Ser Leu Thr Leu Phe
            755                 760                 765

Asp Phe Lys Arg Phe Leu Thr Cys Gly Thr Lys Leu Leu Tyr Leu Trp
770                 775                 780

Thr Ser Ser His Thr Asn Ser Ile Pro Gly Ala Ile Pro Lys Lys Ser
785                 790                 795                 800

Tyr Val Met Glu Arg Ile Val Leu Gln Val Asp Phe Pro Ser Pro Ala
                805                 810                 815

Phe Asp Ile Ile Tyr Thr Ser Pro Gln Ile Asp Arg Asn Ile Ile Gln
            820                 825                 830

Gln Asp Lys Leu Glu Thr Leu Glu Ser Asp Ile Lys Gly Lys Leu Leu
```

-continued

```
            835                 840                 845
Asp Ile Ile His Arg Asp Ser Ser Phe Gly Leu Ser Lys Glu Asp Lys
    850                 855                 860
Val Phe Leu Trp Glu Asn Arg Tyr Tyr Cys Leu Lys His Pro Asn Cys
865                 870                 875                 880
Leu Pro Lys Ile Leu Ala Ser Ala Pro Asn Trp Lys Trp Ala Asn Leu
                885                 890                 895
Ala Lys Thr Tyr Ser Leu Leu His Gln Trp Pro Pro Leu Cys Pro Leu
            900                 905                 910
Ala Ala Leu Glu Leu Leu Asp Ala Lys Phe Ala Asp Gln Gly Val Arg
            915                 920                 925
Ser Leu Ala Val Ser Trp Met Glu Ala Ile Ser Asp Asp Glu Leu Ala
            930                 935                 940
Asp Leu Leu Pro Gln Phe Val Gln Ala Leu Lys Tyr Glu Ile Tyr Leu
945                 950                 955                 960
Asn Ser Ser Leu Val Arg Phe Leu Leu Ser Arg Ala Leu Gly Asn Ile
                965                 970                 975
Gln Ile Ala His Ser Leu Tyr Trp Leu Leu Lys Asp Ala Leu His Asp
            980                 985                 990
Thr His Phe Gly Ser Arg Tyr Glu His Val Leu Gly Ala Leu Leu Ser
            995                 1000                1005
Val Gly Gly Lys Gly Leu Arg Glu Glu Leu Ser Lys Gln Met Lys Leu
        1010                1015                1020
Val Gln Leu Leu Gly Gly Val Ala Glu Lys Val Arg Gln Ala Ser Gly
1025                1030                1035                1040
Ser Thr Arg Gln Val Val Leu Gln Lys Ser Met Glu Arg Val Gln Ser
                1045                1050                1055
Phe Phe Leu Arg Asn Lys Cys Arg Leu Pro Leu Lys Pro Ser Leu Val
            1060                1065                1070
Ala Lys Glu Leu Asn Ile Lys Ser Cys Ser Phe Phe Ser Ser Asn Ala
            1075                1080                1085
Met Pro Leu Lys Val Thr Met Val Asn Ala Asp Pro Leu Gly Glu Glu
        1090                1095                1100
Ile Asn Val Met Phe Lys Val Gly Glu Asp Leu Arg Gln Asp Met Leu
1105                1110                1115                1120
Ala Leu Gln Met Ile Lys Ile Met Asp Lys Ile Trp Leu Lys Glu Gly
                1125                1130                1135
Leu Asp Leu Arg Met Val Ile Phe Arg Cys Leu Ser Thr Gly Arg Asp
            1140                1145                1150
Arg Gly Met Val Glu Leu Val Pro Ala Ser Asp Thr Leu Arg Lys Ile
        1155                1160                1165
Gln Val Glu Tyr Gly Val Thr Gly Ser Phe Lys Asp Lys Pro Leu Ala
    1170                1175                1180
Glu Trp Leu Arg Lys Tyr Asn Pro Ser Glu Glu Tyr Glu Lys Ala
1185                1190                1195                1200
Ser Glu Asn Phe Ile Tyr Ser Cys Ala Gly Cys Cys Val Ala Thr Tyr
                1205                1210                1215
Val Leu Gly Ile Cys Asp Arg His Asn Asp Asn Ile Met Leu Arg Ser
            1220                1225                1230
Thr Gly His Met Phe His Ile Asp Phe Gly Lys Phe Leu Gly His Ala
            1235                1240                1245
Gln Met Phe Gly Ser Phe Lys Arg Asp Arg Ala Pro Phe Val Leu Thr
        1250                1255                1260
```

-continued

Ser Asp Met Ala Tyr Val Ile Asn Gly Gly Glu Lys Pro Thr Ile Arg
1265                1270                1275                1280

Phe Gln Leu Phe Val Asp Leu Cys Cys Gln Ala Tyr Asn Leu Ile Arg
            1285                1290                1295

Lys Gln Thr Asn Leu Phe Leu Asn Leu Leu Ser Leu Met Ile Pro Ser
        1300                1305                1310

Gly Leu Pro Glu Leu Thr Ser Ile Gln Asp Leu Lys Tyr Val Arg Asp
    1315                1320                1325

Ala Leu Gln Pro Gln Thr Thr Asp Ala Glu Ala Thr Ile Phe Phe Thr
1330                1335                1340

Arg Leu Ile Glu Ser Ser Leu Gly Ser Ile Ala Thr Lys Phe Asn Phe
1345                1350                1355                1360

Phe Ile His Asn Leu Ala Gln Leu Arg Phe Ser Gly Leu Pro Ser Asn
            1365                1370                1375

Asp Glu Pro Ile Leu Ser Phe Ser Pro Lys Thr Tyr Ser Phe Arg Gln
        1380                1385                1390

Asp Gly Arg Ile Lys Glu Val Ser Val Phe Thr Tyr His Lys Lys Tyr
    1395                1400                1405

Asn Pro Asp Lys His Tyr Ile Tyr Val Val Arg Ile Leu Arg Glu Gly
1410                1415                1420

His Leu Glu Pro Ser Phe Val Phe Arg Thr Phe Asp Glu Phe Gln Glu
1425                1430                1435                1440

Leu His Asn Lys Leu Ser Ile Ile Phe Pro Leu Trp Lys Leu Pro Gly
            1445                1450                1455

Phe Pro Asn Arg Met Val Leu Gly Arg Thr His Ile Lys Asp Val Ala
        1460                1465                1470

Ala Lys Arg Lys Ile Glu Leu Asn Ser Tyr Leu Gln Ser Leu Met Asn
    1475                1480                1485

Ala Ser Thr Asp Val Ala Glu Cys Asp Leu Val Cys Thr Phe Phe His
1490                1495                1500

Pro Leu Leu Arg Asp Glu Lys Ala Glu Gly Ile Ala Arg Ser Ala Gly
1505                1510                1515                1520

Ala Val Pro Phe Ser Pro Thr Leu Gly Gln Ile Gly Gly Ala Val Lys
            1525                1530                1535

Leu Ser Val Ser Tyr Arg Asn Gly Thr Leu Phe Ile Met Val Met His
        1540                1545                1550

Ile Lys Asp Leu Val Thr Glu Asp Gly Ala Asp Pro Asn Pro Tyr Val
    1555                1560                1565

Lys Thr Tyr Leu Leu Pro Asp Thr His Lys Thr Ser Lys Arg Lys Thr
1570                1575                1580

Lys Ile Ser Arg Lys Thr Arg Asn Pro Thr Phe Asn Glu Met Leu Val
1585                1590                1595                1600

Tyr Ser Gly Tyr Ser Lys Glu Thr Leu Arg Gln Arg Glu Leu Gln Leu
            1605                1610                1615

Ser Val Leu Ser Ala Glu Ser Leu Arg Glu Asn Phe Phe Leu Gly Gly
        1620                1625                1630

Ile Thr Leu Pro Leu Lys Asp Phe Asn Leu Ser Lys Glu Thr Val Lys
    1635                1640                1645

Trp Tyr Gln Leu Thr Ala Ala Thr Tyr Leu
    1650                1655

(2) INFORMATION FOR SEQ ID NO:14:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Gln Gln Pro Ser Arg Asp Asn Pro His Glu Ile Gly Gln Ile Arg Leu
1               5                   10                  15

Ser Leu Gln Tyr Gln Arg Gly Val Leu Thr Val Met Ile His His Ala
            20                  25                  30

Lys Gly Leu Pro Met Leu Gln Gly Gly Gln Glu Pro Asn Thr Tyr Val
        35                  40                  45

Lys Cys Tyr Leu Lys Pro Asp Pro Lys Lys Glu Thr Lys Arg Lys Thr
50                  55                  60

Lys Val Val Arg Lys Thr Cys Val Pro Ser Phe Met Glu Thr Leu Glu
65                  70                  75                  80

Tyr Arg Met Pro Leu Asn Ile Ile Gln Glu Arg Arg Leu Gln Val Thr
                85                  90                  95

Val Trp Ser His Asp Thr Leu Gln Glu Asn Glu Leu Leu Gly Gly Phe
            100                 105                 110

Asp Met Asp Leu Ser Lys Tyr Asp Leu Arg Gln Glu Leu Val Asp Trp
        115                 120                 125

Tyr Arg Leu Gly Ala Val Ser Arg Asn
    130                 135

(2) INFORMATION FOR SEQ ID NO:15:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Val Pro Phe Ser Pro Thr Leu Gly Gln Ile Gly Gly Ala Val Lys Leu
1               5                   10                  15

Ser Val Ser Tyr Arg Asn Gly Thr Leu Phe Ile Met Val Met His Ile
            20                  25                  30

Lys Asp Leu Val Thr Glu Asp Gly Ala Asp Pro Asn Pro Tyr Val Lys
        35                  40                  45

Thr Tyr Leu Leu Pro Asp Thr His Lys Thr Ser Lys Arg Lys Thr Lys
50                  55                  60

Ile Ser Arg Lys Thr Arg Asn Pro Thr Phe Asn Glu Met Leu Val Tyr
65                  70                  75                  80

Ser Gly Tyr Ser Lys Glu Thr Leu Arg Gln Arg Glu Leu Gln Leu Ser
            85                  90                  95

Val Leu Ser Ala Glu Ser Leu Arg Glu Asn Phe Phe Leu Gly Gly Ile
            100                 105                 110

Thr Leu Pro Leu Lys Asp Phe Asn Leu Ser Lys Glu Thr Val Lys Trp
        115                 120                 125

Tyr Gln Leu Thr Ala Ala Thr Tyr Leu
    130                 135

(2) INFORMATION FOR SEQ ID NO:16:

(i) SEQUENCE CHARACTERISTICS:
   (A) LENGTH: 140 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:16:

```
Asn Ser Tyr Asp Ser Asp Glu Ala Thr Thr Leu Gly Ala Leu Glu Phe
1               5                   10                  15

Ser Leu Leu Tyr Asp Gln Asp Asn Ser Ser Leu His Cys Thr Ile Ile
                20                  25                  30

Lys Ala Lys Gly Leu Lys Pro Met Asp Ser Asn Gly Leu Ala Asp Pro
            35                  40                  45

Tyr Val Lys Leu His Leu Leu Pro Gly Ala Ser Lys Ser Asn Lys Leu
        50                  55                  60

Arg Thr Lys Thr Leu Arg Asn Thr Arg Asn Pro Ile Trp Asn Glu Thr
65                  70                  75                  80

Leu Val Tyr His Gly Ile Thr Asp Glu Asp Met Gln Arg Lys Thr Leu
                85                  90                  95

Arg Ile Ser Val Cys Asp Glu Asp Lys Phe Gly His Asn Glu Phe Ile
            100                 105                 110

Gly Glu Thr Arg Phe Ser Leu Lys Lys Leu lys Pro Asn Gln Arg Lys
        115                 120                 125

Asn Phe Asn Ile Cys Leu Glu Arg Val Ile Pro Met
130                 135                 140
```

(2) INFORMATION FOR SEQ ID NO:17:

(i) SEQUENCE CHARACTERISTICS:
   (A) LENGTH: 138 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:17:

```
Gln Gly Gly Glu Lys Glu Pro Glu Lys Leu Gly Asp Ile Cys Thr
1               5                   10                  15

Ser Leu Arg Tyr Val Pro Thr Ala Gly Lys Leu Thr Val Cys Ile Leu
                20                  25                  30

Glu Ala Lys Asn Leu Lys Lys Met Asp Val Gly Gly Leu Ser Asp Pro
            35                  40                  45

Tyr Val Lys Ile His Leu Met Gln Asn Gly Lys Arg Leu Lys Lys Lys
        50                  55                  60

Lys Thr Thr Val Lys Lys Thr Leu Asn Pro Tyr Phe Asn Glu Ser
65                  70                  75                  80

Phe Ser Phe Glu Ile Pro Phe Glu Gln Ile Gln Lys Val Gln Val Val
                85                  90                  95

Val Thr Val Leu Asp Tyr Asp Lys Leu Gly Lys Asn Glu Ala Ile Gly
            100                 105                 110

Lys Ile Phe Val Gly Ser Asn Ala Thr Gly Thr Glu Leu Arg His Trp
        115                 120                 125

Ser Asp Met Leu Ala Asn Pro Arg Arg Pro
130                 135
```

(2) INFORMATION FOR SEQ ID NO:18:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Ser Leu Cys Gly Cys Asp His Thr Glu Arg Arg Gly Arg Ile Tyr Leu
1               5                  10                  15

Glu Ile Asn Val Lys Glu Asn Leu Leu Thr Val Gln Ile Lys Glu Gly
            20                  25                  30

Arg Asn Leu Ile Pro Met Asp Pro Asn Gly Leu Ser Asp Pro Tyr Val
        35                  40                  45

Lys Val Lys Leu Ile Pro Asp Asp Lys Asp Gln Ser Lys Lys Lys Thr
    50                  55                  60

Arg Thr Ile Lys Ala Cys Leu Asn Pro Val Trp Asn Glu Thr Leu Thr
65                  70                  75                  80

Tyr Asp Leu Lys Pro Glu Asp Lys Asp Arg Arg Ile Leu Ile Glu Val
                85                  90                  95

Trp Asp Trp Asp Arg Thr Ser Arg Asn Asp Phe Met Gly Ala Leu Ser
            100                 105                 110

Phe Gly Ile Ser Glu Ile Ile Lys Asn Pro Thr Asn Gly Trp Phe Lys
        115                 120                 125

Leu Leu Thr Gln Asp Glu Gly Glu
    130                 135
```

(2) INFORMATION FOR SEQ ID NO:19:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Ala Ile Phe Lys Cys Gly Asp Asp Leu Gln Gln Asp Gln Leu Thr Ile
1               5                  10                  15

Gln Leu Ile Arg Ile Met Asn Lys Met Trp Leu Ala Glu Arg Leu Asp
            20                  25                  30

Leu Lys Met Val Thr Phe Asn Cys Val Pro Thr Gly Tyr Lys Ser Gly
        35                  40                  45

Met Ile Glu Leu Val Ser Glu Ala Glu Thr Leu Arg Lys Ile Gln Val
    50                  55                  60

Glu Cys Gly Leu Thr Gly Ser Phe Lys Asp Arg Pro Ile Ala Glu Trp
65                  70                  75                  80

Leu Gly Lys Gln Asn Pro Ser Pro Leu Glu Tyr Gln Ser Ala Val Arg
                85                  90                  95

Asn Phe Thr Leu Ser Cys Ala Gly Tyr Ser Val Ala Thr Tyr Val Leu
            100                 105                 110

Gly Ile Cys Asp Arg His Asn Asp Asn Ile Met Leu Lys Thr Ser Gly
        115                 120                 125

His Leu Phe His Ile Asp Phe Gly Lys Phe Leu Gly Asp Ala Gln Met
    130                 135                 140
```

```
Phe Gly Asn Phe Lys Arg Asp Arg Thr Pro Phe Val Leu Thr Ser Asp
145                 150                 155                 160

Met Ala Tyr Val Ile Asn Gly Gly Asp Lys Pro
                165                 170
```

(2) INFORMATION FOR SEQ ID NO:20:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Val Met Phe Lys Val Gly Glu Asp Leu Arg Gln Asp Met Leu Ala Leu
1               5                   10                  15

Gln Met Ile Lys Ile Met Asp Lys Ile Trp Leu Lys Glu Gly Leu Asp
                20                  25                  30

Leu Arg Met Val Ile Phe Arg Cys Leu Ser Thr Gly Arg Asp Arg Gly
                35                  40                  45

Met Val Glu Leu Val Pro Ala Ser Asp Thr Leu Arg Lys Ile Gln Val
50                  55                  60

Glu Tyr Gly Val Thr Gly Ser Phe Lys Asp Lys Pro Leu Ala Glu Trp
65                  70                  75                  80

Leu Arg Lys Tyr Asn Pro Ser Glu Glu Tyr Glu Lys Ala Ser Glu
                85                  90                  95

Asn Phe Ile Tyr Ser Cys Ala Gly Cys Cys Val Ala Thr Tyr Val Leu
                100                 105                 110

Gly Ile Cys Asp Arg His Asn Asp Asn Ile Met Leu Arg Ser Thr Gly
                115                 120                 125

His Met Phe His Ile Asp Phe Gly Lys Phe Leu Gly His Ala Gln Met
                130                 135                 140

Phe Gly Ser Phe Lys Arg Asp Arg Ala Pro Phe Val Leu Thr Ser Asp
145                 150                 155                 160

Met Ala Tyr Val Ile Asn Gly Gly Glu Lys Pro
                165                 170
```

(2) INFORMATION FOR SEQ ID NO:21:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Ile Ile Phe Lys Asn Gly Asp Asp Ile Arg Gln Asp Met Leu Thr Ile
1               5                   10                  15

Gln Ile Ile Arg Ile Met Glu Asn Ile Trp Gln Asn Gln Gly Leu Asp
                20                  25                  30

Ile Arg Met Leu Pro Tyr Gly Cys Leu Ser Ile Gly Asp Cys Val Gly
                35                  40                  45

Leu Ile Glu Val Val Arg Asn Ser His Thr Ile Met Gln Ile Gln Cys
                50                  55                  60

Lys Gly Gly Leu Lys Gly Ala Leu Gln Phe Asn Ser His Thr Leu His
65                  70                  75                  80
```

```
Gln Trp Leu Lys Asp Lys Asn Lys Gly Glu Ile Tyr Asp Ala Ala Ile
                85                  90                  95

Asp Leu Phe Thr Arg Ser Cys Ala Gly Tyr Cys Val Ala Thr Phe Ile
            100                 105                 110

Leu Gly Ile Gly Asp Arg His Asn Ser Asn Ile Met Val Lys Asp Asp
        115                 120                 125

Gly Cys Leu Phe His Ile Asp Phe Gly His Phe Leu Asp His Lys Lys
    130                 135                 140

Lys Lys Phe Gly Tyr Lys Glu Arg Val Pro Phe Val Leu Thr Gln Asp
145                 150                 155                 160

Phe Leu Ile Val Ile Ser Lys Gly Ala Gln Glu
                165                 170

(2) INFORMATION FOR SEQ ID NO:22:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Val Ile Phe Lys Asn Gly Asp Asp Ile Arg Gln Asp Met Leu Thr Ile
1               5                   10                  15

Gln Met Ile Arg Leu Met Asp Leu Ile Trp Lys Glu Ala Gly Leu Asp
            20                  25                  30

Ile Arg Met Leu Pro Tyr Gly Cys Leu Ala Thr Gly Asp Arg Ser Gly
        35                  40                  45

Leu Ile Glu Val Val Ser Thr Ser Glu Thr Ile Ala Asp Ile Gln Leu
    50                  55                  60

Asn Ser Ser Asn Val Ala Ala Ala Ala Ala Phe Asn Lys Asp Ala
65                  70                  75                  80

Leu Leu Asn Trp Leu Lys Glu Tyr Asn Ser Gly Asp Asp Leu Asp Arg
                85                  90                  95

Ala Ile Glu Glu Phe Thr Leu Ser Cys Ala Gly Tyr Cys Val Ala Ser
            100                 105                 110

Tyr Val Leu Gly Ile Gly Asp Arg His Ser Asp Asn Ile Met Val Lys
        115                 120                 125

Lys Thr Gly Gln Leu Phe His Ile Asp Phe Gly His Ile Leu Gly Asn
    130                 135                 140

Phe Lys Ser Lys Phe Gly Ile Lys Glu Arg Val Pro Phe Ile Leu Thr
145                 150                 155                 160

Tyr Asp Phe Ile His Val Ile Gln Gln Gly Lys
                165                 170

(2) INFORMATION FOR SEQ ID NO:23:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:
```

```
Ile Ile Phe Lys His Gly Asp Asp Ile Arg Gln Asp Met Leu Ile Ile
 1               5                  10                  15

Gln Ile Leu Arg Ile Met Glu Ser Ile Trp Glu Thr Glu Ser Leu Asp
                20                  25                  30

Ile Cys Ile Leu Pro Tyr Gly Cys Ile Ser Thr Gly Asp Lys Ile Gly
                35                  40                  45

Met Ile Glu Ile Val Lys Asp Ala Thr Thr Ile Ala Lys Ile Gln Gln
     50                  55                  60

Ser Thr Val Gly Asn Thr Gly Ala Phe Lys Asp Glu Val Leu Asn His
 65                  70                  75                  80

Trp Leu Lys Glu Lys Ser Pro Thr Glu Glu Lys Glu Gln Ala Ala Val
                85                  90                  95

Glu Arg Phe Val Tyr Ser Cys Ala Gly Tyr Cys Val Ala Thr Phe Val
                100                 105                 110

Leu Gly Ile Gly Asp Arg His Asn Asp Asn Ile Met Ile Thr Glu Thr
                115                 120                 125

Gly Asn Leu Phe His Ile Asp Phe Gly His Ile Leu Gly Asn Tyr Lys
    130                 135                 140

Ser Phe Leu Gly Ile Asn Lys Arg Val Pro Phe Val Leu Thr Pro Asp
145                 150                 155                 160

Phe Leu Phe Val Met Gly Thr Ser Gly Lys Lys
                165                 170

(2) INFORMATION FOR SEQ ID NO:24:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Leu Met Phe Lys Val Gly Asp Asp Leu Arg Gln Asp Gln Leu Val Val
 1               5                  10                  15

Gln Ile Ile Ser Leu Met Asn Glu Leu Leu Lys Asn Glu Asn Val Asp
                20                  25                  30

Leu Lys Leu Thr Pro Tyr Lys Ile Leu Ala Thr Gly Pro Gln Glu Gly
                35                  40                  45

Ala Ile Glu Phe Ile Pro Asn Asp Thr Leu Ala Ser Ile Leu Ser Lys
     50                  55                  60

Tyr His Gly Ile Leu Gly Tyr Leu Lys Leu His Tyr Pro Asp Glu Asn
 65                  70                  75                  80

Ala Thr Leu Gly Val Gln Gly Trp Val Leu Asp Asn Phe Val Lys Ser
                85                  90                  95

Cys Ala Gly Tyr Cys Val Ile Thr Tyr Ile Leu Gly Val Gly Asp Arg
                100                 105                 110

His Leu Asp Asn Leu Leu Val Thr Pro Asp Gly His Phe Phe His Ala
    115                 120                 125

Asp Phe Gly Tyr Leu Gly Gln Asp Pro Lys Pro Phe Pro Pro Leu Met
    130                 135                 140

Lys Leu Pro Pro Gln Ile Ile Glu Ala Phe Gly Gly Ala Glu Ser Ser
145                 150                 155                 160

(2) INFORMATION FOR SEQ ID NO:25:
```

(i) SEQUENCE CHARACTERISTICS:
            (A) LENGTH: 179 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:25:

Val Ile Ala Lys Thr Gly Asp Asp Leu Arg Gln Glu Ala Phe Ala Tyr
1               5                   10                  15

Gln Met Ile Gln Ala Met Ala Asn Ile Trp Val Lys Glu Lys Val Asp
            20                  25                  30

Val Trp Val Lys Arg Met Lys Ile Leu Ile Thr Ser Ala Asn Thr Gly
        35                  40                  45

Leu Val Glu Thr Ile Thr Asn Ala Met Ser Val His Ser Ile Lys Lys
    50                  55                  60

Ala Leu Thr Lys Lys Met Ile Glu Asp Ala Glu Leu Asp Asp Lys Gly
65                  70                  75                  80

Gly Ile Ala Ser Leu Asn Asp His Phe Leu Arg Ala Phe Gly Asn Pro
                85                  90                  95

Asn Gly Phe Lys Tyr Arg Arg Ala Gln Asp Asn Phe Ala Ser Ser Leu
            100                 105                 110

Ala Ala Tyr Ser Val Ile Cys Tyr Leu Leu Gln Val Lys Asp Arg His
        115                 120                 125

Asn Gly Asn Ile Met Ile Asp Asn Glu Gly His Val Ser His Ile Asp
    130                 135                 140

Phe Gly Phe Met Leu Ser Asn Ser Pro Gly Ser Val Gly Phe Glu Ala
145                 150                 155                 160

Ala Pro Phe Lys Leu Thr Tyr Glu Tyr Ile Glu Leu Leu Gly Gly Val
                165                 170                 175

Glu Gly Glu (2) INFORMATION FOR SEQ ID NO:26:

(i) SEQUENCE CHARACTERISTICS:
            (A) LENGTH: 184 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:26:

Tyr Val Leu Lys Gly His Glu Asp Ile Arg Gln Asp Ser Leu Val Met
1               5                   10                  15

Gln Leu Phe Gly Leu Val Asn Thr Leu Leu Gln Asn Asp Ala Glu Cys
            20                  25                  30

Phe Arg Arg His Leu Asp Ile Gln Gln Tyr Pro Ala Ile Pro Leu Ser
            35                  40                  45

Pro Lys Ser Gly Leu Leu Gly Trp Val Pro Asn Ser Asp Thr Phe His
    50                  55                  60

Val Leu Ile Arg Glu His Arg Glu Ala Lys Lys Ile Pro Leu Asn Ile
65                  70                  75                  80

Glu His Trp Val Met Leu Gln Met Ala Pro Asp Tyr Asp Asn Leu Thr
                85                  90                  95

Leu Leu Gln Lys Val Glu Val Phe Thr Tyr Ala Leu Asn Asn Tyr Thr
            100                 105                 110

```
Arg Ser Leu Ala Val Met Ser Met Thr Gly Tyr Ile Leu Gly Leu Gly
        115                 120                 125

Asp Arg His Pro Ser Asn Leu Met Leu Asp Arg Ile Thr Gly Lys Val
    130                 135                 140

Ile His Ile Asp Phe Gly Asp Cys Phe Glu Ala Ala Ile Leu Arg Glu
145                 150                 155                 160

Lys Phe Pro Glu Lys Val Pro Phe Arg Leu Thr Arg Met Leu Thr Tyr
                165                 170                 175

Ala Met Glu Val Ser Gly Ile Glu
            180

(2) INFORMATION FOR SEQ ID NO:27:

(i) SEQUENCE CHARACTERISTICS:
        (A) LENGTH: 6831 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 148..5775

(xi) SEQUENCE DESCRIPTION: SEQ ID NO:27:

GCTTGTTGCA TTCCGTTTTG TGTTATTTCG TGCTCCCCGT CAAGGGAAAA CCTCAACCAA      60

AAAGAGACTA GCAACGGGTG TAAAAAGCAG CGGAGGTGAC ACCTCAAAAA GCAACTCAAC     120

GGACCGGACG CTTTAGACGA GGGGATA ATG TCA AAT CAA GCG CAT ATC GAC         171
                              Met Ser Asn Gln Ala His Ile Asp
                                1               5

TAC GAC AAA CAA TTC CAG GAT GAC CTG GCC AAG GCG ACC GCC CTG AGT       219
Tyr Asp Lys Gln Phe Gln Asp Asp Leu Ala Lys Ala Thr Ala Leu Ser
     10              15                  20

CTA GAG CAG CAT GCC CTC GAT GAC TAC AGG CGA AAC AAG AAG TAC GGC       267
Leu Glu Gln His Ala Leu Asp Asp Tyr Arg Arg Asn Lys Lys Tyr Gly
 25              30                  35                  40

TCC GGG TAT CAG CAA AGC TCC ACC GTT GCT GGC CGA GAT TAC CAG GCG       315
Ser Gly Tyr Gln Gln Ser Ser Thr Val Ala Gly Arg Asp Tyr Gln Ala
                 45                  50                  55

GCG CAA CGT AGT CAG AGC CTA CAT CAA CCA CGA CGG CAC TCG GAG GTG       363
Ala Gln Arg Ser Gln Ser Leu His Gln Pro Arg Arg His Ser Glu Val
             60                  65                  70

CAT CAG GTG GCC ATC AGT CCG GAG AAT GCG GAA CGA TCG CGC ACA CCG       411
His Gln Val Ala Ile Ser Pro Glu Asn Ala Glu Arg Ser Arg Thr Pro
         75                  80                  85

CCG GCC CAG GGA ACG GAT AAC GAT CTG ATC TGC CTC GCA AGT CCC ACC       459
Pro Ala Gln Gly Thr Asp Asn Asp Leu Ile Cys Leu Ala Ser Pro Thr
     90                  95                 100

AGC AAG CAG CCA GAG AGT AGC AGT CCC TTT GGC AAA CTT ATA GAG GAT       507
Ser Lys Gln Pro Glu Ser Ser Ser Pro Phe Gly Lys Leu Ile Glu Asp
105                 110                 115                 120

CTG CAG CGG ATG CAG CCG ACC AAT CCG CAG TCG GCC CTG GTG CCA ATG       555
Leu Gln Arg Met Gln Pro Thr Asn Pro Gln Ser Ala Leu Val Pro Met
                125                 130                 135

GGT CCA GTT GCG TCG GCT TCG ATT CCT CCT CAA TAC GGC TTC CCA CCT       603
Gly Pro Val Ala Ser Ala Ser Ile Pro Pro Gln Tyr Gly Phe Pro Pro
                140                 145                 150

CAT CAG CAA CGT CCA ACG GCT GCT CAG CCC ACA CCG TAC GGC ATG GTT       651
His Gln Gln Arg Pro Thr Ala Ala Gln Pro Thr Pro Tyr Gly Met Val
```

-continued

```
            155                 160                      165
GCA GGT GGA GTT GTT GGT GGA CCG GCT TAC GGT GAC CTG CAG TTG GTG        699
Ala Gly Gly Val Val Gly Gly Pro Ala Tyr Gly Asp Leu Gln Leu Val
    170             175                 180

CCT TAC CAA CCA GCT GCC CAG CAA CAG AGG CCA CTA AAC AGC GAG GAG        747
Pro Tyr Gln Pro Ala Ala Gln Gln Gln Arg Pro Leu Asn Ser Glu Glu
185             190                 195                 200

CTG CAG CGG CTG TAC AGC ATG CCC GCT CAA ATG GCC GTG GTT CCA GTG        795
Leu Gln Arg Leu Tyr Ser Met Pro Ala Gln Met Ala Val Val Pro Val
                205                 210                 215

CCG CAG CCA AAC GCC TAT ATG TAC TAT CCC GGA GCT GTG GTT ACT CCA        843
Pro Gln Pro Asn Ala Tyr Met Tyr Tyr Pro Gly Ala Val Val Thr Pro
            220                 225                 230

TAC ACG GCT CCC ATT GTT CCC GGA TCG GCT GCT TTT ATG CCG CCG CAG        891
Tyr Thr Ala Pro Ile Val Pro Gly Ser Ala Ala Phe Met Pro Pro Gln
        235                 240                 245

TAT CCC GCA CAG GGA TAT GGC TTT GGA GGT GCT TAC ACG CAC ATG GAT        939
Tyr Pro Ala Gln Gly Tyr Gly Phe Gly Gly Ala Tyr Thr His Met Asp
    250                 255                 260

TTG CGT CGA CCC CAA TCG CAA CCA GCT CCC CAA CAA ACA GCA CCG ACA        987
Leu Arg Arg Pro Gln Ser Gln Pro Ala Pro Gln Gln Thr Ala Pro Thr
265             270                 275                 280

ACA AGT CAT CAT CAC AGC CAA CCG TCC AAC CAT TCC ACT TCC TCC CCC       1035
Thr Ser His His His Ser Gln Pro Ser Asn His Ser Thr Ser Ser Pro
                285                 290                 295

GCA GAG GCC AAT GGA GTA GCC TTC CCA GCG CGT CGC CAA GTG CCC TCG       1083
Ala Glu Ala Asn Gly Val Ala Phe Pro Ala Arg Arg Gln Val Pro Ser
            300                 305                 310

ACT GTC GGG GTT AGC TCT AGT AGC CAC ACT GGA AAC AAT GGT CAT TCC       1131
Thr Val Gly Val Ser Ser Ser Ser His Thr Gly Asn Asn Gly His Ser
        315                 320                 325

TCG GTC CCA CGC AGG GGC AAC GAT TTG ATC GAC CTC AAC CAC GAG GAC       1179
Ser Val Pro Arg Arg Gly Asn Asp Leu Ile Asp Leu Asn His Glu Asp
    330                 335                 340

TAC TCC CGT GTG AGT GTG CTG GAG GCA TTC GAT CCC CTG CTA AAC GAC       1227
Tyr Ser Arg Val Ser Val Leu Glu Ala Phe Asp Pro Leu Leu Asn Asp
345             350                 355                 360

AAT ACT GGC AAC GAC ACC GCC TCC GAC AGC ACT TCC TAC TAT GCG GAA       1275
Asn Thr Gly Asn Asp Thr Ala Ser Asp Ser Thr Ser Tyr Tyr Ala Glu
                365                 370                 375

TAC GAT CCC TTT GAT TTT CTG TAC AGC GGA GAT GCA GCA ACC CAA TAT       1323
Tyr Asp Pro Phe Asp Phe Leu Tyr Ser Gly Asp Ala Ala Thr Gln Tyr
            380                 385                 390

TCC GAT CCA ATG TAT GAG GCA GTC AAC AGG TGG GAC AAA ACT GTG GCC       1371
Ser Asp Pro Met Tyr Glu Ala Val Asn Arg Trp Asp Lys Thr Val Ala
        395                 400                 405

ACC GTG AGT CCG AAT GTT GGT CTA ATC GGT TGG CGC CAA GAT TTT CTG       1419
Thr Val Ser Pro Asn Val Gly Leu Ile Gly Trp Arg Gln Asp Phe Leu
    410                 415                 420

AGC CAG CCA TCT ACA TCT TCA TCG CAA TAT GGT GTT GCG CCG CCA GAG       1467
Ser Gln Pro Ser Thr Ser Ser Ser Gln Tyr Gly Val Ala Pro Pro Glu
425             430                 435                 440

GAG AGT CTG AAG CTT GCG GAG AAC GGA TCT GAA ACT ATC TCG CCT CCT       1515
Glu Ser Leu Lys Leu Ala Glu Asn Gly Ser Glu Thr Ile Ser Pro Pro
                445                 450                 455

CCG CCG TTG CCG CCC CGG AAC CAG CAG TGC TAT GAA TCA AAC CAG GCA       1563
Pro Pro Leu Pro Pro Arg Asn Gln Gln Cys Tyr Glu Ser Asn Gln Ala
            460                 465                 470

GCC ATG CCG GTC TCC AGG CCT CCT CAG TCT TCT GTT TTG ACG GAC AGC       1611
Ala Met Pro Val Ser Arg Pro Pro Gln Ser Ser Val Leu Thr Asp Ser
```

```
                -continued

Ala Met Pro Val Ser Arg Pro Gln Ser Ser Val Leu Thr Asp Ser
        475                 480                 485

TAC ACC TCC AGC ATT CCG GCC AAC GTG GTG CTG GAC CGG CGG AAA ACT       1659
Tyr Thr Ser Ser Ile Pro Ala Asn Val Val Leu Asp Arg Arg Lys Thr
490                 495                 500

TGT ACA CGA CTG TAC GAA TTG ATC AGC GAC CAG CGC ACT GAT GAT CCC       1707
Cys Thr Arg Leu Tyr Glu Leu Ile Ser Asp Gln Arg Thr Asp Asp Pro
505                 510                 515                 520

GAA CTT TTG GAA TTT TAC CAC ATG GTA AAG GAG GTG AGG GCA CGC TAT       1755
Glu Leu Leu Glu Phe Tyr His Met Val Lys Glu Val Arg Ala Arg Tyr
                525                 530                 535

CCG CAT GAC GAT GCG CCC ACC AAT GTG GGA CAT GTT GTG GCC GCC GAG       1803
Pro His Asp Asp Ala Pro Thr Asn Val Gly His Val Val Ala Ala Glu
        540                 545                 550

TTT AAT TAT CAC TAC ATG ATG GAC ACC AGC ATC AAA GTG ATT GTG CAT       1851
Phe Asn Tyr His Tyr Met Met Asp Thr Ser Ile Lys Val Ile Val His
        555                 560                 565

CCG GCT CTA AAT ACA CTT CAA TCA ACG GTC CTG GCT GCG TCC ATG GGC       1899
Pro Ala Leu Asn Thr Leu Gln Ser Thr Val Leu Ala Ala Ser Met Gly
570                 575                 580

AAG GAA CAG GTG AAG GGA TAT GGA ATG CCA GTA ACA TTC ACT TGC GAT       1947
Lys Glu Gln Val Lys Gly Tyr Gly Met Pro Val Thr Phe Thr Cys Asp
585                 590                 595                 600

ATT GAT TCG GTT GTG GCA CAG GTG GTG GCA CAA GCT TTG GCC TCG CTG       1995
Ile Asp Ser Val Val Ala Gln Val Val Ala Gln Ala Leu Ala Ser Leu
                605                 610                 615

GAG GGA CAA GTC AAG GGT ACC GTC ACA GAT TAT GCG GTC AAG CCC ATT       2043
Glu Gly Gln Val Lys Gly Thr Val Thr Asp Tyr Ala Val Lys Pro Ile
                620                 625                 630

GGT CTT CTG GAG TGG CTG GCA CCC ACC TCG AGA CTG AGT CAG CTG GAG       2091
Gly Leu Leu Glu Trp Leu Ala Pro Thr Ser Arg Leu Ser Gln Leu Glu
        635                 640                 645

TGC GTG CAC AAT AGC TTC CAA TTG GAG AAG GAT GTA CAT TTG GGC CTG       2139
Cys Val His Asn Ser Phe Gln Leu Glu Lys Asp Val His Leu Gly Leu
        650                 655                 660

TGC CTT AGT ACG GCG GCA AAC ATG CAG GCT ATT GCA CGA ACA GAG CGG       2187
Cys Leu Ser Thr Ala Ala Asn Met Gln Ala Ile Ala Arg Thr Glu Arg
665                 670                 675                 680

GAT GAT GAG CAC GAT GCG GAT TTG CTG CCG GAA CAT CCT CTT CCA AAC       2235
Asp Asp Glu His Asp Ala Asp Leu Leu Pro Glu His Pro Leu Pro Asn
                685                 690                 695

GAG GTT GTG CAA ATT GTG ACC TAC GAC AAT ATG ATG ATA CTC ATC GAA       2283
Glu Val Val Gln Ile Val Thr Tyr Asp Asn Met Met Ile Leu Ile Glu
                700                 705                 710

ACG CTG GAG ATG GAG ATT GAC AAG CTG GAA TCG GCG GCC GAC GGA GTA       2331
Thr Leu Glu Met Glu Ile Asp Lys Leu Glu Ser Ala Ala Asp Gly Val
        715                 720                 725

CCC GGA CGG AGT GTC GTG AGC TGC TCC GGA GTT GTC CAA GCA GTG AAG       2379
Pro Gly Arg Ser Val Val Ser Cys Ser Gly Val Val Gln Ala Val Lys
        730                 735                 740

GCC ATA TGC GCA CTG CTC GGT TCA ATC GAC ACA ATG GAA ATT GCA CGA       2427
Ala Ile Cys Ala Leu Leu Gly Ser Ile Asp Thr Met Glu Ile Ala Arg
745                 750                 755                 760

TGT GTT GCC GAT CTG AAG CGC ATT TGC GAG GTG GAG CAA AAG AAG TAC       2475
Cys Val Ala Asp Leu Lys Arg Ile Cys Glu Val Glu Gln Lys Lys Tyr
                765                 770                 775

TCG ACG GGC GCT AGC AAC CCA GAG ATT GTG AGT GAC TAT GGT GAT TAC       2523
Ser Thr Gly Ala Ser Asn Pro Glu Ile Val Ser Asp Tyr Gly Asp Tyr
                780                 785                 790
```

```
GCT CAA GTT GTA CTC CGC CCG CGC TCC ATG CTG GAG CAG ATC AAG GTC      2571
Ala Gln Val Val Leu Arg Pro Arg Ser Met Leu Glu Gln Ile Lys Val
        795                 800                 805

AAG TGC AAC GAG CTG CGA GAT GCA GTG CAA GAG CTG GTT GAA TTG TAT      2619
Lys Cys Asn Glu Leu Arg Asp Ala Val Gln Glu Leu Val Glu Leu Tyr
810                 815                 820

GCG AAT GTT TTC CGG GTG GCA TTC TCC GTG AAG ACG CCC GAT TAC TCA      2667
Ala Asn Val Phe Arg Val Ala Phe Ser Val Lys Thr Pro Asp Tyr Ser
825                 830                 835                 840

ACA ACA CCC ATA CCC ATT TCC TGC GTG TCC AAA CCA ATT GTG GTA TGC      2715
Thr Thr Pro Ile Pro Ile Ser Cys Val Ser Lys Pro Ile Val Val Cys
                845                 850                 855

ATT AGC TGC CTA CAC AGG CCG CTG CCG AAT TGG AAG TTC GAC GAT TAT      2763
Ile Ser Cys Leu His Arg Pro Leu Pro Asn Trp Lys Phe Asp Asp Tyr
        860                 865                 870

TCC CTG TGC GTA CAA ATC GTT TAT GGA ACG CGC CTG CTG TCG AAG CCG      2811
Ser Leu Cys Val Gln Ile Val Tyr Gly Thr Arg Leu Leu Ser Lys Pro
            875                 880                 885

AAT GTG CTG ACC TGC TCC AAC GAT ACA AGT GGA GGC CTG TTT CCT CGT      2859
Asn Val Leu Thr Cys Ser Asn Asp Thr Ser Gly Gly Leu Phe Pro Arg
    890                 895                 900

CTT AAC TTC AGT GCC TGG CTG ACT TTC GAT CAG CAT CCC ATC TGC ACT      2907
Leu Asn Phe Ser Ala Trp Leu Thr Phe Asp Gln His Pro Ile Cys Thr
905                 910                 915                 920

CTG CCC AGG GAG GCG CGC CTT ACG TTC GTG TTG TAT GGA AAA CAG GCG      2955
Leu Pro Arg Glu Ala Arg Leu Thr Phe Val Leu Tyr Gly Lys Gln Ala
                925                 930                 935

GCC AGC GAA GGC GAA CCC AAC GCC GAT CAG AAT GGA GAG AGG CGT CAG      3003
Ala Ser Glu Gly Glu Pro Asn Ala Asp Gln Asn Gly Glu Arg Arg Gln
        940                 945                 950

GTG ACC ACT GAA CTG GGT TGG TGT TCG ATC CAA CTG TTT GAC TTT AAG      3051
Val Thr Thr Glu Leu Gly Trp Cys Ser Ile Gln Leu Phe Asp Phe Lys
            955                 960                 965

CGA GTG ATG ATC TGC GGC CCC TAC TTA CTG TCT TTA TGG CCA CCA ATG      3099
Arg Val Met Ile Cys Gly Pro Tyr Leu Leu Ser Leu Trp Pro Pro Met
    970                 975                 980

ACG GAC AAA ATG CTT GGA CCA GCT CCG GCT CGA GGC TGT CAT CCG CAA      3147
Thr Asp Lys Met Leu Gly Pro Ala Pro Ala Arg Gly Cys His Pro Gln
985                 990                 995                 1000

CCC GAC TTT TGC CCC GTT TTG AGC ATT GAA GTA CCT CCG TAT GGA GGA      3195
Pro Asp Phe Cys Pro Val Leu Ser Ile Glu Val Pro Pro Tyr Gly Gly
                1005                1010                1015

CGC ATT GAG TTT CCT GAG CAC CAG GAG GTG CCA AAA CCT GCA CCA CAC      3243
Arg Ile Glu Phe Pro Glu His Gln Glu Val Pro Lys Pro Ala Pro His
        1020                1025                1030

TAC GAT TTT GCC TCT CTG GAT GCC AAT CTT CAA GAG GAG CTG CTG GAC      3291
Tyr Asp Phe Ala Ser Leu Asp Ala Asn Leu Gln Glu Glu Leu Leu Asp
            1035                1040                1045

ACC GCA GAG CTG GGC TAC ACA GGA GCC ACA GAA CGA CGT GAA GTG TTC      3339
Thr Ala Glu Leu Gly Tyr Thr Gly Ala Thr Glu Arg Arg Glu Val Phe
    1050                1055                1060

TGG GAA AAA CGG CTC TAC CTG CAG AGC TAT CCC AAT GCC CTG CCA AAG      3387
Trp Glu Lys Arg Leu Tyr Leu Gln Ser Tyr Pro Asn Ala Leu Pro Lys
1065                1070                1075                1080

GTT CTT CAT GCC GCT CAC AGT TGG GAT TAT GCC AAT TTG ATC GAT TTG      3435
Val Leu His Ala Ala His Ser Trp Asp Tyr Ala Asn Leu Ile Asp Leu
                1085                1090                1095

CAT GCG CTG CTG CAC TCC TGG GCA CCA CTC TCG CCA TTG CAG TCG TTG      3483
His Ala Leu Leu His Ser Trp Ala Pro Leu Ser Pro Leu Gln Ser Leu
        1100                1105                1110
```

```
GAG TTA CTT CTG CCA CGA TAT CCG GAT GCT AAG GTT CGC GAG AAA GCC      3531
Glu Leu Leu Leu Pro Arg Tyr Pro Asp Ala Lys Val Arg Glu Lys Ala
            1115                1120                1125

GTG GAG TGG ATC TCC AAG ATG CCC AAC GAC CAG CTC GTC GAC TTT CTG      3579
Val Glu Trp Ile Ser Lys Met Pro Asn Asp Gln Leu Val Asp Phe Leu
1130                1135                1140

CCT CAA TTG GTG CAA AGT TTA AAA CAT GAC ACA TAC GAA GGC TCG GCA      3627
Pro Gln Leu Val Gln Ser Leu Lys His Asp Thr Tyr Glu Gly Ser Ala
1145                1150                1155                1160

ATG GCT CGA TTC TTG CTG TCC AAA TGC CTG GAG TCA CCG CGC TTT GCC      3675
Met Ala Arg Phe Leu Leu Ser Lys Cys Leu Glu Ser Pro Arg Phe Ala
                1165                1170                1175

CAT CAC ATG TAT TGG CTG CTT GTA CAC AGT CTG CCT GAC GAT CCC CAC      3723
His His Met Tyr Trp Leu Leu Val His Ser Leu Pro Asp Asp Pro His
            1180                1185                1190

AAC TCT ATT GGA GCA GCG ATG GTG GAT CAG GAG TAT GAC GAG TCT CAG      3771
Asn Ser Ile Gly Ala Ala Met Val Asp Gln Glu Tyr Asp Glu Ser Gln
            1195                1200                1205

GTT ACC CAG GTC CGT TAC TAC CGC CGG AAC AAA ATG ATG CTG CGT GCT      3819
Val Thr Gln Val Arg Tyr Tyr Arg Arg Asn Lys Met Met Leu Arg Ala
1210                1215                1220

TTA ATG GCG ATT TGC GGC GAA AAG ATG CTT CAG CGA TTT ATG TAC CAG      3867
Leu Met Ala Ile Cys Gly Glu Lys Met Leu Gln Arg Phe Met Tyr Gln
1225                1230                1235                1240

CAC CGA ATG TGT CAG AAA CTT ACT ACT ATT GCG GAG TCG GTT AAA GAG      3915
His Arg Met Cys Gln Lys Leu Thr Thr Ile Ala Glu Ser Val Lys Glu
                1245                1250                1255

GCT AAG GAG TCG ATG CGT CAA AAA AGC CTA GCC GCA GGC ATG GAC GAG      3963
Ala Lys Glu Ser Met Arg Gln Lys Ser Leu Ala Ala Gly Met Asp Glu
                1260                1265                1270

GTG CAC CAA GAC TTA CTG GAG CAA CCC ACT TGC CTA CCG CTG GGA CCA      4011
Val His Gln Asp Leu Leu Glu Gln Pro Thr Cys Leu Pro Leu Gly Pro
            1275                1280                1285

GAA CTG GAG GTA ACT GGA GTG AGT GTG CGT AAC TGT AGC TAC TTT AAC      4059
Glu Leu Glu Val Thr Gly Val Ser Val Arg Asn Cys Ser Tyr Phe Asn
            1290                1295                1300

TCC AAC ACG CTG CCG CTG AAG ATC AAC TTT GTG GGA CCT GAT GCC GAA      4107
Ser Asn Thr Leu Pro Leu Lys Ile Asn Phe Val Gly Pro Asp Ala Glu
1305                1310                1315                1320

TCT TTA CCG GCT ATC TTT AAG TGC GGA GAT GAC TTG CAG CAG GAT CAG      4155
Ser Leu Pro Ala Ile Phe Lys Cys Gly Asp Asp Leu Gln Gln Asp Gln
                1325                1330                1335

TTA ACT ATA CAG CTA ATT AGG ATT ATG AAC AAA ATG TGG TTG GCC GAA      4203
Leu Thr Ile Gln Leu Ile Arg Ile Met Asn Lys Met Trp Leu Ala Glu
            1340                1345                1350

CGA TTG GAC CTG AAG ATG GTC ACC TTT AAT TGT GTG CCT ACG GGA TAC      4251
Arg Leu Asp Leu Lys Met Val Thr Phe Asn Cys Val Pro Thr Gly Tyr
            1355                1360                1365

AAG AGC GGT ATG ATT GAG CTG GTT AGC GAG GCG GAA ACG TTG AGA AAA      4299
Lys Ser Gly Met Ile Glu Leu Val Ser Glu Ala Glu Thr Leu Arg Lys
            1370                1375                1380

ATT CAA GTA GAG TGC GGT CTG ACG GGG TCC TTT AAG GAT CGC CCG ATC      4347
Ile Gln Val Glu Cys Gly Leu Thr Gly Ser Phe Lys Asp Arg Pro Ile
1385                1390                1395                1400

GCT GAG TGG TTA GGC AAG CAG AAT CCC AGT CCT CTC GAG TAC CAG AGT      4395
Ala Glu Trp Leu Gly Lys Gln Asn Pro Ser Pro Leu Glu Tyr Gln Ser
                1405                1410                1415

GCT GTG CGA AAT TTT ACG CTA TCC TGT GCT GGA TAC AGT GTG GCC ACG      4443
Ala Val Arg Asn Phe Thr Leu Ser Cys Ala Gly Tyr Ser Val Ala Thr
```

-continued

```
              1420                1425                1430
TAT GTG CTA GGC ATC TGT GAT CCC CAC AAT GAC AAC ATC ATG TTA AAG    4491
Tyr Val Leu Gly Ile Cys Asp Pro His Asn Asp Asn Ile Met Leu Lys
            1435                1440                1445

ACT TCG GGT CAC TTG TTT CAC ATT GAC TTT GGC AAG TTT CTT GGC GAT    4539
Thr Ser Gly His Leu Phe His Ile Asp Phe Gly Lys Phe Leu Gly Asp
        1450                1455                1460

GCT CAG ATG TTT GGA AAC TTT AAG AGA GAT CGC ACT CCA TTT GTC CTG    4587
Ala Gln Met Phe Gly Asn Phe Lys Arg Asp Arg Thr Pro Phe Val Leu
1465                1470                1475                1480

ACT TCC GAC ATG GCT TAT GTC ATA AAT GGC GGC GAT AAG CCC TCC ACA    4635
Thr Ser Asp Met Ala Tyr Val Ile Asn Gly Gly Asp Lys Pro Ser Thr
            1485                1490                1495

GAC TTT CAC TAT TTC GTG GAC CTA TGT TGT CGA GCC TTT AAT ATC GTG    4683
Asp Phe His Tyr Phe Val Asp Leu Cys Cys Arg Ala Phe Asn Ile Val
        1500                1505                1510

CGG AAA AAT GCT GAT CTA CTC TTG CAC ACC CTG GCC CAC ATG GCT ACA    4731
Arg Lys Asn Ala Asp Leu Leu Leu His Thr Leu Ala His Met Ala Thr
            1515                1520                1525

GCA GGC ATG CCG GGA GTA AAC TCC AAT GCT GTG CAA TAT GTA CGA CGC    4779
Ala Gly Met Pro Gly Val Asn Ser Asn Ala Val Gln Tyr Val Arg Arg
    1530                1535                1540

GCC CTA TTG CCA TCT CAA TCG AAT CCC GAG GCA GCT GCC ACA TTT GCC    4827
Ala Leu Leu Pro Ser Gln Ser Asn Pro Glu Ala Ala Ala Thr Phe Ala
1545                1550                1555                1560

AAG ATG ATT CAA TCC TCT TTG AAA AGC TGG TTC ACG CAA TTC AAT TTC    4875
Lys Met Ile Gln Ser Ser Leu Lys Ser Trp Phe Thr Gln Phe Asn Phe
            1565                1570                1575

TTT CTG CAC AAT CTG GCC CAG ACG CGT TTC ACC CCA GAC GAG GGA TCA    4923
Phe Leu His Asn Leu Ala Gln Thr Arg Phe Thr Pro Asp Glu Gly Ser
        1580                1585                1590

GGA GAG CTG CTA TCG TTC GTG CCA CGA AAA TAT ACA ATG CAG CAG GAT    4971
Gly Glu Leu Leu Ser Phe Val Pro Arg Lys Tyr Thr Met Gln Gln Asp
            1595                1600                1605

GGT CGC TTG AAG ATT GTA AAG GTG GTG TGT TTC CAG AAG CAT TAC AGC    5019
Gly Arg Leu Lys Ile Val Lys Val Val Cys Phe Gln Lys His Tyr Ser
        1610                1615                1620

ATG GAA AAG TTT TAT ATG TAT ATT CTG GAA GTG ACG CGA CAT GGA CAG    5067
Met Glu Lys Phe Tyr Met Tyr Ile Leu Glu Val Thr Arg His Gly Gln
1625                1630                1635                1640

CCC GAT CCG ACA CAT TTG TTC CGG TCA TAT CGG GAA TTC ACG GAA TTC    5115
Pro Asp Pro Thr His Leu Phe Arg Ser Tyr Arg Glu Phe Thr Glu Phe
            1645                1650                1655

CAT CAG AAG TTA TGC ATG CAC TTT CCT TTG GTT AAA CTG CAC AGT CTG    5163
His Gln Lys Leu Cys Met His Phe Pro Leu Val Lys Leu His Ser Leu
        1660                1665                1670

CCG GCT GGT GTG CAT GTG GGC CGT TCC AAT ATC AAA TCC GTG GCA GAA    5211
Pro Ala Gly Val His Val Gly Arg Ser Asn Ile Lys Ser Val Ala Glu
    1675                1680                1685

AAA CGA CTA CCT CTT ATA CAG CGA TTT TTG AAA TCG TTG TTC GAT GCG    5259
Lys Arg Leu Pro Leu Ile Gln Arg Phe Leu Lys Ser Leu Phe Asp Ala
            1690                1695                1700

TCC GAG GAA ATA GCC CAT TCC GAG CTC GTT TAC ACA TTC TTT CAC CCG    5307
Ser Glu Glu Ile Ala His Ser Glu Leu Val Tyr Thr Phe Phe His Pro
1705                1710                1715                1720

CTG CTG CGC GAT CAG CAG GAA GCC AAG CTT GGG ATG CCG AAG ATA AAG    5355
Leu Leu Arg Asp Gln Gln Glu Ala Lys Leu Gly Met Pro Lys Ile Lys
            1725                1730                1735

GAG GTG AAG CAA CAA CCG TCG CGG GAT AAT CCC CAC GAG ATT GGC CAA    5403
```

```
Glu Val Lys Gln Gln Pro Ser Arg Asp Asn Pro His Glu Ile Gly Gln
            1740                1745                1750

ATA CGA CTA TCG CTG CAA TAT CAA CGC GGC GTA CTT ACT GTG ATG ATA       5451
Ile Arg Leu Ser Leu Gln Tyr Gln Arg Gly Val Leu Thr Val Met Ile
        1755                1760                1765

CAC CAC GCC AAA GAA CTG CCC ATG TTA CAG GGC GGT CAG GAG CCC AAC       5499
His His Ala Lys Glu Leu Pro Met Leu Gln Gly Gly Gln Glu Pro Asn
            1770                1775                1780

ACA TAT GTG AAG TGC TAC CTA AAA CCG GAT CCC AAA AAG GAG ACC AAA       5547
Thr Tyr Val Lys Cys Tyr Leu Lys Pro Asp Pro Lys Lys Glu Thr Lys
1785                1790                1795                1800

CGC AAG ACC AAA GTG GTG CGC AAG ACC TGT GTG CCC AGT TTC ATG GAA       5595
Arg Lys Thr Lys Val Val Arg Lys Thr Cys Val Pro Ser Phe Met Glu
                1805                1810                1815

ACT TTG GAG TAC CGA ATG CCA CTG AAT ATT ATT CAA GAG CGC CGC CTT       5643
Thr Leu Glu Tyr Arg Met Pro Leu Asn Ile Ile Gln Glu Arg Arg Leu
            1820                1825                1830

CAG GTT ACG GTT TGG TCG CAC GAC ACC CTG CAG GAG AAC GAG CTG CTT       5691
Gln Val Thr Val Trp Ser His Asp Thr Leu Gln Glu Asn Glu Leu Leu
                1835                1840                1845

GGA GGC TTC GAT ATG GAT CTG TCG AAG TAC GAC CTG CGA CAG GAG CTC       5739
Gly Gly Phe Asp Met Asp Leu Ser Lys Tyr Asp Leu Arg Gln Glu Leu
            1850                1855                1860

GTC GAC TGG TAT CGC CTG GGC GCG GTG TCC AGG AAC TGACCAGATC            5785
Val Asp Trp Tyr Arg Leu Gly Ala Val Ser Arg Asn
1865                1870                1875

CTAGGGACGA GCTATTTTGA ACCTCTTGGG ACACTCTGCC TACCGACAAT CAGGCCTAGG     5845
ATAATGCCAA TACTAATATA TGTTGTGCCT GTCTTCTTTC GATCGCAATA ATACTTACTT     5905
ACTCGAAGTG ATTGTACATT CCATATACCA ATATTAAAAA TAACATAACA GTAGTAGTAT     5965
TATTTCGTAA AATGTGTGCC TCAAATGTAA ATATTTTATA ATGACCGCAA ACAACATTCT     6025
TTTGGACATC TGAATGTAAT TATAACTATA AGTATAGAA CATGCTTACT CTATTTACAT      6085
TTAAAATCAA TCAATTTTAT TGTGCACCTT GGGAATTCAG AAAATGAATT ATATTGGTAG     6145
TTTGTTTGAA TCGTTCTGTC GTCGGCACCT GGCAATTGTT CTTTTGAAGT AGTTAAATAT     6205
AAAAGTTCAG TATTATGGCT TAAATTCTAT AAGAGATTAT TAAAAACCTT CTAGCTCGCT     6265
GGTCTGTAAT ATCTAAAATT AAAACTTGCA CGAAGAATAA TCATTACTAA CTTTTTTGCA     6325
CTTTTCTAAT TACTTAAAGT AAAAAGAGAA CTAAAATTTC CTAAAGAAAT TAGGCATTGC     6385
AAGCAGAATA ACGCACAGAT ACAGATTCTT TCTGATTGTA TTTTGTTTGT CACTTAATAT     6445
TCACAAAATT GCTTTGTCAA AAGCAAACGC CTGACTGGGT CTAAAACAAA TTACAAAGT      6505
TATAGGGAAT TACTATCAGA GAGAACAAGA ACTAAAAGTG TCTTAAAAAT GAAACGAATA     6565
TTGTAAAATA TATAATAAGA GCACACACAC ACCGCAAACA ACAAATTATA TTTTTATAGA     6625
AAAAAGAAAC ATTCAAAAGC TACTTCTGCC TGAGCATTTC AAATAGTACT TTGATACTGA     6685
TTAAAAACTA CCTAAGACGT ATCTGATGTT TTCATAAAAT TATAATTAAT AGGAAAAAAT     6745
TAAATTTCTG AAGTGTTGAG GAATCGTAAA AATGTTAGCT GGCGGTAATC ACTTTTGGCA     6805
CAAATATATG AGCATAAAAA AAGGCA                                          6831

(2) INFORMATION FOR SEQ ID NO:28:

(i) SEQUENCE CHARACTERISTICS:
        (A) LENGTH: 1876 amino acids
        (B) TYPE: amino acid
        (D) TOPOLOGY: linear
```

(ii) MOLECULE TYPE: protein (xi) SEQUENCE DESCRIPTION: SEQ ID NO:28:

```
Met Ser Asn Gln Ala His Ile Asp Tyr Asp Lys Gln Phe Gln Asp Asp
 1               5                  10                  15

Leu Ala Lys Ala Thr Ala Leu Ser Leu Glu Gln His Ala Leu Asp Asp
                20                  25                  30

Tyr Arg Arg Asn Lys Lys Tyr Gly Ser Gly Tyr Gln Ser Ser Thr
             35                  40                  45

Val Ala Gly Arg Asp Tyr Gln Ala Ala Gln Arg Ser Gln Ser Leu His
     50                  55                  60

Gln Pro Arg Arg His Ser Glu Val His Gln Val Ala Ile Ser Pro Glu
 65                  70                  75                  80

Asn Ala Glu Arg Ser Arg Thr Pro Pro Ala Gln Gly Thr Asp Asn Asp
                 85                  90                  95

Leu Ile Cys Leu Ala Ser Pro Thr Ser Lys Gln Pro Glu Ser Ser Ser
            100                 105                 110

Pro Phe Gly Lys Leu Ile Glu Asp Leu Gln Arg Met Gln Pro Thr Asn
            115                 120                 125

Pro Gln Ser Ala Leu Val Pro Met Gly Pro Val Ala Ser Ala Ser Ile
    130                 135                 140

Pro Pro Gln Tyr Gly Phe Pro Pro His Gln Gln Arg Pro Thr Ala Ala
145                 150                 155                 160

Gln Pro Thr Pro Tyr Gly Met Val Ala Gly Val Val Gly Gly Pro
                165                 170                 175

Ala Tyr Gly Asp Leu Gln Leu Val Pro Tyr Gln Pro Ala Ala Gln Gln
                180                 185                 190

Gln Arg Pro Leu Asn Ser Glu Glu Leu Gln Arg Leu Tyr Ser Met Pro
    195                 200                 205

Ala Gln Met Ala Val Val Pro Val Pro Gln Pro Asn Ala Tyr Met Tyr
    210                 215                 220

Tyr Pro Gly Ala Val Val Thr Pro Tyr Thr Ala Pro Ile Val Pro Gly
225                 230                 235                 240

Ser Ala Ala Phe Met Pro Pro Gln Tyr Pro Ala Gln Gly Tyr Gly Phe
                245                 250                 255

Gly Gly Ala Tyr Thr His Met Asp Leu Arg Arg Pro Gln Ser Gln Pro
                260                 265                 270

Ala Pro Gln Gln Thr Ala Pro Thr Thr Ser His His Ser Gln Pro
    275                 280                 285

Ser Asn His Ser Thr Ser Ser Pro Ala Glu Ala Asn Gly Val Ala Phe
    290                 295                 300

Pro Ala Arg Arg Gln Val Pro Ser Thr Val Gly Val Ser Ser Ser Ser
305                 310                 315                 320

His Thr Gly Asn Asn Gly His Ser Ser Val Pro Arg Arg Gly Asn Asp
                325                 330                 335

Leu Ile Asp Leu Asn His Glu Tyr Ser Arg Val Ser Val Leu Glu
            340                 345                 350

Ala Phe Asp Pro Leu Leu Asn Asp Asn Thr Gly Asn Asp Thr Ala Ser
            355                 360                 365

Asp Ser Thr Ser Tyr Tyr Ala Glu Tyr Asp Pro Phe Asp Phe Leu Tyr
    370                 375                 380

Ser Gly Asp Ala Ala Thr Gln Tyr Ser Asp Pro Met Tyr Glu Ala Val
385                 390                 395                 400
```

```
Asn Arg Trp Asp Lys Thr Val Ala Thr Val Ser Pro Asn Val Gly Leu
            405                 410                 415

Ile Gly Trp Arg Gln Asp Phe Leu Ser Gln Pro Ser Thr Ser Ser Ser
            420                 425                 430

Gln Tyr Gly Val Ala Pro Pro Glu Ser Leu Lys Leu Ala Glu Asn
            435                 440                 445

Gly Ser Glu Thr Ile Ser Pro Pro Pro Leu Pro Pro Arg Asn Gln
    450                 455                 460

Gln Cys Tyr Glu Ser Asn Gln Ala Ala Met Pro Val Ser Arg Pro Pro
465                 470                 475                 480

Gln Ser Ser Val Leu Thr Asp Ser Tyr Thr Ser Ser Ile Pro Ala Asn
            485                 490                 495

Val Val Leu Asp Arg Arg Lys Thr Cys Thr Arg Leu Tyr Glu Leu Ile
            500                 505                 510

Ser Asp Gln Arg Thr Asp Asp Pro Glu Leu Leu Glu Phe Tyr His Met
            515                 520                 525

Val Lys Glu Val Arg Ala Arg Tyr Pro His Asp Asp Ala Pro Thr Asn
            530                 535                 540

Val Gly His Val Val Ala Ala Glu Phe Asn Tyr His Tyr Met Met Asp
545                 550                 555                 560

Thr Ser Ile Lys Val Ile Val His Pro Ala Leu Asn Thr Leu Gln Ser
            565                 570                 575

Thr Val Leu Ala Ala Ser Met Gly Lys Glu Gln Val Lys Gly Tyr Gly
            580                 585                 590

Met Pro Val Thr Phe Thr Cys Asp Ile Asp Ser Val Val Ala Gln Val
            595                 600                 605

Val Ala Gln Ala Leu Ala Ser Leu Glu Gly Gln Val Lys Gly Thr Val
            610                 615                 620

Thr Asp Tyr Ala Val Lys Pro Ile Gly Leu Leu Glu Trp Leu Ala Pro
625                 630                 635                 640

Thr Ser Arg Leu Ser Gln Leu Glu Cys Val His Asn Ser Phe Gln Leu
            645                 650                 655

Glu Lys Asp Val His Leu Gly Leu Cys Leu Ser Thr Ala Ala Asn Met
            660                 665                 670

Gln Ala Ile Ala Arg Thr Glu Arg Asp Glu His Asp Ala Asp Leu
            675                 680                 685

Leu Pro Glu His Pro Leu Pro Asn Glu Val Val Gln Ile Val Thr Tyr
            690                 695                 700

Asp Asn Met Met Ile Leu Ile Glu Thr Leu Glu Met Glu Ile Asp Lys
705                 710                 715                 720

Leu Glu Ser Ala Ala Asp Gly Val Pro Gly Arg Ser Val Val Ser Cys
            725                 730                 735

Ser Gly Val Val Gln Ala Val Lys Ala Ile Cys Ala Leu Leu Gly Ser
            740                 745                 750

Ile Asp Thr Met Glu Ile Ala Arg Cys Val Ala Asp Leu Lys Arg Ile
            755                 760                 765

Cys Glu Val Glu Gln Lys Lys Tyr Ser Thr Gly Ala Ser Asn Pro Glu
770                 775                 780

Ile Val Ser Asp Tyr Gly Asp Tyr Ala Gln Val Val Leu Arg Pro Arg
785                 790                 795                 800

Ser Met Leu Glu Gln Ile Lys Val Lys Cys Asn Glu Leu Arg Asp Ala
            805                 810                 815

Val Gln Glu Leu Val Glu Leu Tyr Ala Asn Val Phe Arg Val Ala Phe
```

-continued

```
                820                 825                 830
Ser Val Lys Thr Pro Asp Tyr Ser Thr Thr Pro Ile Pro Ile Ser Cys
            835                 840                 845

Val Ser Lys Pro Ile Val Val Cys Ile Ser Cys Leu His Arg Pro Leu
850                 855                 860

Pro Asn Trp Lys Phe Asp Asp Tyr Ser Leu Cys Val Gln Ile Val Tyr
865                 870                 875                 880

Gly Thr Arg Leu Leu Ser Lys Pro Asn Val Leu Thr Cys Ser Asn Asp
            885                 890                 895

Thr Ser Gly Gly Leu Phe Pro Arg Leu Asn Phe Ser Ala Trp Leu Thr
                900                 905                 910

Phe Asp Gln His Pro Ile Cys Thr Leu Pro Arg Glu Ala Arg Leu Thr
            915                 920                 925

Phe Val Leu Tyr Gly Lys Gln Ala Ala Ser Glu Gly Glu Pro Asn Ala
            930                 935                 940

Asp Gln Asn Gly Glu Arg Arg Gln Val Thr Thr Glu Leu Gly Trp Cys
945                 950                 955                 960

Ser Ile Gln Leu Phe Asp Phe Lys Arg Val Met Ile Cys Gly Pro Tyr
                965                 970                 975

Leu Leu Ser Leu Trp Pro Pro Met Thr Asp Lys Met Leu Gly Pro Ala
                980                 985                 990

Pro Ala Arg Gly Cys His Pro Gln Pro Asp Phe Cys Pro Val Leu Ser
            995                 1000                1005

Ile Glu Val Pro Pro Tyr Gly Gly Arg Ile Glu Phe Pro Glu His Gln
        1010                1015                1020

Glu Val Pro Lys Pro Ala Pro His Tyr Asp Phe Ala Ser Leu Asp Ala
1025                1030                1035                1040

Asn Leu Gln Glu Glu Leu Leu Asp Thr Ala Glu Leu Gly Tyr Thr Gly
                1045                1050                1055

Ala Thr Glu Arg Arg Glu Val Phe Trp Glu Lys Arg Leu Tyr Leu Gln
            1060                1065                1070

Ser Tyr Pro Asn Ala Leu Pro Lys Val Leu His Ala Ala His Ser Trp
            1075                1080                1085

Asp Tyr Ala Asn Leu Ile Asp Leu His Ala Leu Leu His Ser Trp Ala
            1090                1095                1100

Pro Leu Ser Pro Leu Gln Ser Leu Glu Leu Leu Leu Pro Arg Tyr Pro
1105                1110                1115                1120

Asp Ala Lys Val Arg Glu Lys Ala Val Glu Trp Ile Ser Lys Met Pro
            1125                1130                1135

Asn Asp Gln Leu Val Asp Phe Leu Pro Gln Leu Val Gln Ser Leu Lys
            1140                1145                1150

His Asp Thr Tyr Glu Gly Ser Ala Met Ala Arg Phe Leu Leu Ser Lys
            1155                1160                1165

Cys Leu Glu Ser Pro Arg Phe Ala His His Met Tyr Trp Leu Leu Val
            1170                1175                1180

His Ser Leu Pro Asp Asp Pro His Asn Ser Ile Gly Ala Ala Met Val
1185                1190                1195                1200

Asp Gln Glu Tyr Asp Glu Ser Gln Val Thr Gln Val Arg Tyr Tyr Arg
            1205                1210                1215

Arg Asn Lys Met Met Leu Arg Ala Leu Met Ala Ile Cys Gly Glu Lys
            1220                1225                1230

Met Leu Gln Arg Phe Met Tyr Gln His Arg Met Cys Gln Lys Leu Thr
            1235                1240                1245
```

-continued

```
Thr Ile Ala Glu Ser Val Lys Glu Ala Lys Glu Ser Met Arg Gln Lys
    1250                1255                1260
Ser Leu Ala Ala Gly Met Asp Glu Val His Gln Asp Leu Leu Glu Gln
1265                1270                1275                1280
Pro Thr Cys Leu Pro Leu Gly Pro Glu Leu Glu Val Thr Gly Val Ser
            1285                1290                1295
Val Arg Asn Cys Ser Tyr Phe Asn Ser Asn Thr Leu Pro Leu Lys Ile
            1300                1305                1310
Asn Phe Val Gly Pro Asp Ala Glu Ser Leu Pro Ala Ile Phe Lys Cys
            1315                1320                1325
Gly Asp Asp Leu Gln Gln Asp Gln Leu Thr Ile Gln Leu Ile Arg Ile
            1330                1335                1340
Met Asn Lys Met Trp Leu Ala Glu Arg Leu Asp Leu Lys Met Val Thr
1345                1350                1355                1360
Phe Asn Cys Val Pro Thr Gly Tyr Lys Ser Gly Met Ile Glu Leu Val
            1365                1370                1375
Ser Glu Ala Glu Thr Leu Arg Lys Ile Gln Val Glu Cys Gly Leu Thr
            1380                1385                1390
Gly Ser Phe Lys Asp Arg Pro Ile Ala Glu Trp Leu Gly Lys Gln Asn
            1395                1400                1405
Pro Ser Pro Leu Glu Tyr Gln Ser Ala Val Arg Asn Phe Thr Leu Ser
    1410                1415                1420
Cys Ala Gly Tyr Ser Val Ala Thr Tyr Val Leu Gly Ile Cys Asp Pro
1425                1430                1435                1440
His Asn Asp Asn Ile Met Leu Lys Thr Ser Gly His Leu Phe His Ile
            1445                1450                1455
Asp Phe Gly Lys Phe Leu Gly Asp Ala Gln Met Phe Gly Asn Phe Lys
            1460                1465                1470
Arg Asp Arg Thr Pro Phe Val Leu Thr Ser Asp Met Ala Tyr Val Ile
            1475                1480                1485
Asn Gly Gly Asp Lys Pro Ser Thr Asp Phe His Tyr Phe Val Asp Leu
            1490                1495                1500
Cys Cys Arg Ala Phe Asn Ile Val Arg Lys Asn Ala Asp Leu Leu Leu
1505                1510                1515                1520
His Thr Leu Ala His Met Ala Thr Ala Gly Met Pro Gly Val Asn Ser
            1525                1530                1535
Asn Ala Val Gln Tyr Val Arg Arg Ala Leu Leu Pro Ser Gln Ser Asn
            1540                1545                1550
Pro Glu Ala Ala Ala Thr Phe Ala Lys Met Ile Gln Ser Ser Leu Lys
    1555                1560                1565
Ser Trp Phe Thr Gln Phe Asn Phe Phe Leu His Asn Leu Ala Gln Thr
    1570                1575                1580
Arg Phe Thr Pro Asp Glu Gly Ser Gly Glu Leu Leu Ser Phe Val Pro
1585                1590                1595                1600
Arg Lys Tyr Thr Met Gln Gln Asp Gly Arg Leu Lys Ile Val Lys Val
            1605                1610                1615
Val Cys Phe Gln Lys His Tyr Ser Met Glu Lys Phe Tyr Met Tyr Ile
            1620                1625                1630
Leu Glu Val Thr Arg His Gly Gln Pro Asp Pro Thr His Leu Phe Arg
            1635                1640                1645
Ser Tyr Arg Glu Phe Thr Glu Phe His Gln Lys Leu Cys Met His Phe
    1650                1655                1660
```

-continued

```
Pro Leu Val Lys Leu His Ser Leu Pro Ala Gly Val His Val Gly Arg
1665                1670                1675                1680

Ser Asn Ile Lys Ser Val Ala Glu Lys Arg Leu Pro Leu Ile Gln Arg
                1685                1690                1695

Phe Leu Lys Ser Leu Phe Asp Ala Ser Glu Glu Ile Ala His Ser Glu
            1700                1705                1710

Leu Val Tyr Thr Phe Phe His Pro Leu Leu Arg Asp Gln Gln Glu Ala
        1715                1720                1725

Lys Leu Gly Met Pro Lys Ile Lys Glu Val Lys Gln Gln Pro Ser Arg
    1730                1735                1740

Asp Asn Pro His Glu Ile Gly Gln Ile Arg Leu Ser Leu Gln Tyr Gln
1745                1750                1755                1760

Arg Gly Val Leu Thr Val Met Ile His Ala Lys Glu Leu Pro Met
                1765                1770                1775

Leu Gln Gly Gly Gln Glu Pro Asn Thr Tyr Val Lys Cys Tyr Leu Lys
            1780                1785                1790

Pro Asp Pro Lys Lys Glu Thr Lys Arg Lys Thr Lys Val Val Arg Lys
        1795                1800                1805

Thr Cys Val Pro Ser Phe Met Glu Thr Leu Glu Tyr Arg Met Pro Leu
    1810                1815                1820

Asn Ile Ile Gln Glu Arg Arg Leu Gln Val Thr Val Trp Ser His Asp
1825                1830                1835                1840

Thr Leu Gln Glu Asn Glu Leu Leu Gly Gly Phe Asp Met Asp Leu Ser
                1845                1850                1855

Lys Tyr Asp Leu Arg Gln Glu Leu Val Asp Trp Tyr Arg Leu Gly Ala
            1860                1865                1870

Val Ser Arg Asn
        1875
```

(2) INFORMATION FOR SEQ ID NO:29:

(i) SEQUENCE CHARACTERISTICS:
        (A) LENGTH: 5285 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 3..5180

(ix) FEATURE:
        (A) NAME/KEY: CDS
        (B) LOCATION: 5183..5195

(ix) FEATURE:
        (A) NAME/KEY: CDS
        (B) LOCATION: 5198..5285

(xi) SEQUENCE DESCRIPTION: SEQ ID NO:29:

```
TG CAG AGC TCG GCT GGC CGC GGA GTG AGT CGA AGC TCT CCT CAG CGG       47
   Gln Ser Ser Ala Gly Arg Gly Val Ser Arg Ser Ser Pro Gln Arg
   1               5                   10                  15

CCG GCT GAG CCA GCT GAG GCG GGA GAA AAA CAT GGC TCG GAC CTT GGA      95
Pro Ala Glu Pro Ala Glu Ala Gly Glu Lys His Gly Ser Asp Leu Gly
            20                  25                  30

GGG CGC GAA GGC TCG GGT TGC GGT GAA GAC CAA GAC TCC CGC AGC GTG     143
Gly Arg Glu Gly Ser Gly Cys Gly Glu Asp Gln Asp Ser Arg Ser Val
        35                  40                  45
```

```
AGG TCC TGG TAT TTT GGA AGC TAC AAG AAA AAA AGA TTA AGA GGT TTG    191
Arg Ser Trp Tyr Phe Gly Ser Tyr Lys Lys Lys Arg Leu Arg Gly Leu
        50                  55                  60

TTC TCT TTT GTG GAC ATG GCT CAG ATT TCC AAC AAC AGT GAA TTT AAA    239
Phe Ser Phe Val Asp Met Ala Gln Ile Ser Asn Asn Ser Glu Phe Lys
65                  70                  75

CAA TGT TCA TCT TCA CAT CCA GAA CCA ATA AGA ACC AAA GAT GTG AAC    287
Gln Cys Ser Ser Ser His Pro Glu Pro Ile Arg Thr Lys Asp Val Asn
80                  85                  90                  95

AAA GCA GAA GCG TTA CAG ATG GAA GCA GAA GCC TTA GCA AAA CTG CAG    335
Lys Ala Glu Ala Leu Gln Met Glu Ala Glu Ala Leu Ala Lys Leu Gln
                100                 105                 110

AAG GAT AGA CAA ATG ACT GAC AGC CCA AGA GGC TTT GAG CTG TCT AGC    383
Lys Asp Arg Gln Met Thr Asp Ser Pro Arg Gly Phe Glu Leu Ser Ser
            115                 120                 125

AGC ACT AGA CAA AGA ACA CAA GGT TTT AAC AAA CAG GAT TAT GAT CTC    431
Ser Thr Arg Gln Arg Thr Gln Gly Phe Asn Lys Gln Asp Tyr Asp Leu
        130                 135                 140

ATG GTG TTT CCT GAG TTG GAT TCC CAA AAA AGA GCA GTA GAT ATT GAT    479
Met Val Phe Pro Glu Leu Asp Ser Gln Lys Arg Ala Val Asp Ile Asp
145                 150                 155

GTA GAA AAG CTC ACC CAG GCT GAA CTT GAG AAG ATA TTG CTG GAC GAC    527
Val Glu Lys Leu Thr Gln Ala Glu Leu Glu Lys Ile Leu Leu Asp Asp
160                 165                 170                 175

AAT TTT GAA ACT AGA AAA CCT CCT GCA TTG CCA GTT ACT CCT GTT CTG    575
Asn Phe Glu Thr Arg Lys Pro Pro Ala Leu Pro Val Thr Pro Val Leu
                180                 185                 190

AGC CCT TCG TTC TCA ACA CAG CTG TAT CTT AGA CCT AGT GGT CAA AGA    623
Ser Pro Ser Phe Ser Thr Gln Leu Tyr Leu Arg Pro Ser Gly Gln Arg
            195                 200                 205

GGC CAG TGG CCC CCT GGA TTA TGC GGG CCT TCC ACG TAC ACT TTA CCT    671
Gly Gln Trp Pro Pro Gly Leu Cys Gly Pro Ser Thr Tyr Thr Leu Pro
        210                 215                 220

TCT ACT TAT CCT TCA GCA TAC AGT AAA CAG GCC ACA TTC CAG AAT GGC    719
Ser Thr Tyr Pro Ser Ala Tyr Ser Lys Gln Ala Thr Phe Gln Asn Gly
225                 230                 235

TTC AGT CCA AGG ATG CCC ACT TTT CCA TCA ACA GAG TCT GTA TAT TTA    767
Phe Ser Pro Arg Met Pro Thr Phe Pro Ser Thr Glu Ser Val Tyr Leu
240                 245                 250                 255

AGA CTT CCT GGA CAG TCT CCA TAT TTT TCA TAT CCT TTG ACA CCT GCC    815
Arg Leu Pro Gly Gln Ser Pro Tyr Phe Ser Tyr Pro Leu Thr Pro Ala
                260                 265                 270

ACA CCA TTT CAT CCA CAA GGA AGT TTA CCA GTC TAT CGG CCA CTA GTC    863
Thr Pro Phe His Pro Gln Gly Ser Leu Pro Val Tyr Arg Pro Leu Val
            275                 280                 285

AGT CCT GAC ATG GCA AAA CTA TTT GAA AAA ATA GCA AGT ACC TCA GAA    911
Ser Pro Asp Met Ala Lys Leu Phe Glu Lys Ile Ala Ser Thr Ser Glu
        290                 295                 300

TTT TTA AAA AAT GGG AAA GCA AGG ACT GAT TTG GAG ATA GCA AAC TCG    959
Phe Leu Lys Asn Gly Lys Ala Arg Thr Asp Leu Glu Ile Ala Asn Ser
305                 310                 315

AAA GCT TCA GTC TGC AAT CTA CAG ATA TCT CCA AAG TCT GAA GAC ATC    1007
Lys Ala Ser Val Cys Asn Leu Gln Ile Ser Pro Lys Ser Glu Asp Ile
320                 325                 330                 335

AAT AAG TTT GAT TGG TTA GAC TTG GAT CCT TGG GAT GCT GTT CTT CTT    1055
Asn Lys Phe Asp Trp Leu Asp Leu Asp Pro Trp Asp Ala Val Leu Leu
                340                 345                 350

GAA GAG AGA TCG CCA AGT TGT CAC CTA GAA AGA AAG GTG AAT GGA AAA    1103
Glu Glu Arg Ser Pro Ser Cys His Leu Glu Arg Lys Val Asn Gly Lys
            355                 360                 365
```

```
TCC CTT TCT GGG GCA ACT GTA ACA AGA AGC CAG TCT TTA ATC ATT CGG    1151
Ser Leu Ser Gly Ala Thr Val Thr Arg Ser Gln Ser Leu Ile Ile Arg
        370                 375                 380

ACA GCT CAA TTT ACA AAA GCC CAG GGC CAA GTA TCT CAG AAA GAC CCA    1199
Thr Ala Gln Phe Thr Lys Ala Gln Gly Gln Val Ser Gln Lys Asp Pro
385                 390                 395

AAT GGG ACC AGT AGT TTG CCA ACT GGA AGT TCT CTT CTA CAA GAA TTT    1247
Asn Gly Thr Ser Ser Leu Pro Thr Gly Ser Ser Leu Leu Gln Glu Phe
400                 405                 410                 415

GAA GTA CAG AAT GAC GAG GTG GCA GCT TTT TGT CAA TCC ATT ATG AAA    1295
Glu Val Gln Asn Asp Glu Val Ala Ala Phe Cys Gln Ser Ile Met Lys
                420                 425                 430

TTG AAG ACC AAA TTT CCA TAT ACT GAT CAC TGC ACA AAT CCA GGC TAT    1343
Leu Lys Thr Lys Phe Pro Tyr Thr Asp His Cys Thr Asn Pro Gly Tyr
        435                 440                 445

TTG TTA AGT CCA GTG ACA GTG CAA AGA AAC ATG TGT GGG GAG AAT GCC    1391
Leu Leu Ser Pro Val Thr Val Gln Arg Asn Met Cys Gly Glu Asn Ala
            450                 455                 460

AGT GTG AAG GTC TCC ATT GAA ATT GAA GGG CTT CAA CTA CCA GTT ACT    1439
Ser Val Lys Val Ser Ile Glu Ile Glu Gly Leu Gln Leu Pro Val Thr
465                 470                 475

TTT ACA TGT GAT GTG AGT TCT ACT GTA GAA ATA ATT ATA ATG CAA GCC    1487
Phe Thr Cys Asp Val Ser Ser Thr Val Glu Ile Ile Ile Met Gln Ala
480                 485                 490                 495

CTT TCG TGG GTA CAT GAT GAC TTG AAT CAA GTG GAT GTT GGC AGC TAC    1535
Leu Ser Trp Val His Asp Asp Leu Asn Gln Val Asp Val Gly Ser Tyr
                500                 505                 510

ATT CTG AAA GTT TGT GGT CAA GAG GAG GTT CTA CAG AAT AAT CAT TGC    1583
Ile Leu Lys Val Cys Gly Gln Glu Glu Val Leu Gln Asn Asn His Cys
            515                 520                 525

CTT GGA AGT CAC GAA CAT ATT CAA AAT TGT CGA AAA TGG GAC ACA GAG    1631
Leu Gly Ser His Glu His Ile Gln Asn Cys Arg Lys Trp Asp Thr Glu
        530                 535                 540

ATT AAA TTA CAG CTC TTG ACC TTG AGT GCA ATG TGC CAG AAT CTG GCT    1679
Ile Lys Leu Gln Leu Leu Thr Leu Ser Ala Met Cys Gln Asn Leu Ala
545                 550                 555

CGA ACA GCA GAA GAT GAT GAA GCA CCT GTG GAT TTA AAC AAA TAC TTG    1727
Arg Thr Ala Glu Asp Asp Glu Ala Pro Val Asp Leu Asn Lys Tyr Leu
560                 565                 570                 575

TAT CAA ATA GAA AAA CCT TAT AAA GAA GTC ATG ACA AGA CAC CCT GTT    1775
Tyr Gln Ile Glu Lys Pro Tyr Lys Glu Val Met Thr Arg His Pro Val
                580                 585                 590

GAA GAG CTC TTA GAT TCC TAT CAC TAC CAA GTA GAA CTG GCT CTT CAA    1823
Glu Glu Leu Leu Asp Ser Tyr His Tyr Gln Val Glu Leu Ala Leu Gln
            595                 600                 605

ACT GAA AAC CAG CAC CGA GCT GTT GAT CAA GTG ATT AAA GCA GTA AGA    1871
Thr Glu Asn Gln His Arg Ala Val Asp Gln Val Ile Lys Ala Val Arg
        610                 615                 620

AAA ATT TGT AGT GCT TTA GAT GGG GTG GAG ACC CCC TCC GTT ACA GAA    1919
Lys Ile Cys Ser Ala Leu Asp Gly Val Glu Thr Pro Ser Val Thr Glu
625                 630                 635

GCA GTG AAG AAG TTA AAG CGA GCA GTT AAC CTT CCA AGG AAT AAA AGT    1967
Ala Val Lys Lys Leu Lys Arg Ala Val Asn Leu Pro Arg Asn Lys Ser
640                 645                 650                 655

GCT GAT GTG ACT TCA TTA TCT GGA AGT GAC ACA AGG AAG AAC TCA ACT    2015
Ala Asp Val Thr Ser Leu Ser Gly Ser Asp Thr Arg Lys Asn Ser Thr
                660                 665                 670

AAG GGG TCA CTG AAT CCT GAA AAT CCT GTT CAA GTA AGC ATG GAT CAC    2063
Lys Gly Ser Leu Asn Pro Glu Asn Pro Val Gln Val Ser Met Asp His
```

```
                675                 680                 685
CTA ACA ACA CGC ATT TAT GAT CTT CTC AGG CTC CAT GCA AAT TCT AGT    2111
Leu Thr Thr Arg Ile Tyr Asp Leu Leu Arg Leu His Ala Asn Ser Ser
        690                 695                 700

AGG TGT TCT ACA GGC TGT CCC CGA GGG AGC AGG AAC ATC AAG GAA GCA    2159
Arg Cys Ser Thr Gly Cys Pro Arg Gly Ser Arg Asn Ile Lys Glu Ala
    705                 710                 715

TGG ACT GCA ACG GAG CAG CTC CAG TTC ACT GTC TAT GCC GCA CAC GGA    2207
Trp Thr Ala Thr Glu Gln Leu Gln Phe Thr Val Tyr Ala Ala His Gly
720                 725                 730                 735

ATT TCC AGT AAC TGG GTA TCA AAT TAT GAA AAA TAC TAC TTG ATA TGT    2255
Ile Ser Ser Asn Trp Val Ser Asn Tyr Glu Lys Tyr Tyr Leu Ile Cys
            740                 745                 750

TCC CTG TCT CAC AAT GGG AAG GAT CTT TTT AAG CCT ATT CAG TCA AAG    2303
Ser Leu Ser His Asn Gly Lys Asp Leu Phe Lys Pro Ile Gln Ser Lys
        755                 760                 765

AAG GTT GGC ACG TAC AAG AAT TTC TTC TAT CTT ATT AAA TGG GAT GAA    2351
Lys Val Gly Thr Tyr Lys Asn Phe Phe Tyr Leu Ile Lys Trp Asp Glu
    770                 775                 780

CTA ATC ATT TTT CCT ATC CAG ATA TCG CAG TTG CCA TTA GAA TCA GTT    2399
Leu Ile Ile Phe Pro Ile Gln Ile Ser Gln Leu Pro Leu Glu Ser Val
785                 790                 795

CTT CAT CTT ACT CTG TTT GGA GTT TTA AAT CAG AGC AGT GGA AGT TCC    2447
Leu His Leu Thr Leu Phe Gly Val Leu Asn Gln Ser Ser Gly Ser Ser
800                 805                 810                 815

CCT GAT TCT AAT AAA CAG AGA AAG GGG CCA GAA GCT CTG GGC AAA GTT    2495
Pro Asp Ser Asn Lys Gln Arg Lys Gly Pro Glu Ala Leu Gly Lys Val
            820                 825                 830

TCT TTA ACT CTA TTT GAT TTT AAA CGG TTT TTA ACA TGT GGA ACT AAA    2543
Ser Leu Thr Leu Phe Asp Phe Lys Arg Phe Leu Thr Cys Gly Thr Lys
        835                 840                 845

CTT CTC TAC CTT TGG ACT TCA TCA CAT ACA AAT TCT ATT CCT GGA GCA    2591
Leu Leu Tyr Leu Trp Thr Ser Ser His Thr Asn Ser Ile Pro Gly Ala
    850                 855                 860

ATC CCC AAA AAA AGC TAT GTC ATG GAA AGA ATT GTG CTA CAG GTT GAT    2639
Ile Pro Lys Lys Ser Tyr Val Met Glu Arg Ile Val Leu Gln Val Asp
865                 870                 875

TTT CCT TCT CCT GCG TTT GAC ATT ATT TAT ACA TCT CCT CAA ATT GAT    2687
Phe Pro Ser Pro Ala Phe Asp Ile Ile Tyr Thr Ser Pro Gln Ile Asp
880                 885                 890                 895

AGA AAC ATT ATA CAG CAA GAC AAG TTG GAA ACA CTG GAG AGT GAT ATA    2735
Arg Asn Ile Ile Gln Gln Asp Lys Leu Glu Thr Leu Glu Ser Asp Ile
            900                 905                 910

AAG GGG AAA CTT CTG GAT ATT ATT CAC AGA GAT TCA TCA TTT GGA CTT    2783
Lys Gly Lys Leu Leu Asp Ile Ile His Arg Asp Ser Ser Phe Gly Leu
        915                 920                 925

TCT AAA GAA GAT AAG GTC TTT TTG TGG GAA AAC CGC TAT TAT TGC CTA    2831
Ser Lys Glu Asp Lys Val Phe Leu Trp Glu Asn Arg Tyr Tyr Cys Leu
    930                 935                 940

AAA CAT CCA AAT TGT CTT CCG AAG ATA TTA GCA AGT GCT CCA AAC TGG    2879
Lys His Pro Asn Cys Leu Pro Lys Ile Leu Ala Ser Ala Pro Asn Trp
945                 950                 955

AAG TGG GCT AAT CTT GCC AAA ACT TAC TCA TTG CTG CAT CAG TGG CCG    2927
Lys Trp Ala Asn Leu Ala Lys Thr Tyr Ser Leu Leu His Gln Trp Pro
960                 965                 970                 975

CCA TTG TGC CCA CTA GCT GCA TTG GAG CTC CTT GAT GCA AAA TTT GCT    2975
Pro Leu Cys Pro Leu Ala Ala Leu Glu Leu Leu Asp Ala Lys Phe Ala
            980                 985                 990

GAT CAG GGG GTG CGA TCG CTT GCT GTG AGC TGG ATG GAG GCC ATT AGT    3023
```

-continued

```
Asp Gln Gly Val Arg Ser Leu Ala Val Ser Trp Met Glu Ala Ile Ser
        995                 1000                1005

GAT GAT GAG CTA GCA GAT CTG CTC CCA CAG TTC GTA CAG GCT TTG AAA      3071
Asp Asp Glu Leu Ala Asp Leu Leu Pro Gln Phe Val Gln Ala Leu Lys
        1010                1015                1020

TAT GAA ATT TAT TTG AAT AGT TCA CTA GTG CGC TTC CTT CTG TCC AGG      3119
Tyr Glu Ile Tyr Leu Asn Ser Ser Leu Val Arg Phe Leu Leu Ser Arg
        1025                1030                1035

GCA TTG GGA AAC ATC CAG ATA GCA CAC AGT TTG TAT TGG CTT CTC AAG      3167
Ala Leu Gly Asn Ile Gln Ile Ala His Ser Leu Tyr Trp Leu Leu Lys
1040                1045                1050                1055

GAT GCT TTG CAT GAT ACA CAC TTT GGA AGC AGA TAT GAA CAT GTG TTG      3215
Asp Ala Leu His Asp Thr His Phe Gly Ser Arg Tyr Glu His Val Leu
                1060                1065                1070

GGT GCT CTC CTC TCT GTA GGA GGA AAA GGA CTC AGA GAA GAG CTT TCT      3263
Gly Ala Leu Leu Ser Val Gly Gly Lys Gly Leu Arg Glu Glu Leu Ser
                1075                1080                1085

AAG CAG ATG AAA CTT GTA CAG CTT TTA GGA GGA GTG GCA GAA AAA GTA      3311
Lys Gln Met Lys Leu Val Gln Leu Leu Gly Gly Val Ala Glu Lys Val
        1090                1095                1100

AGG CAG GCT AGT GGA TCA ACA AGA CAG GTT GTC CTC CAA AAG AGT ATG      3359
Arg Gln Ala Ser Gly Ser Thr Arg Gln Val Val Leu Gln Lys Ser Met
        1105                1110                1115

GAA CGG GTA CAG TCC TTT TTT CTG AGA AAT AAA TGC CGT CTT CCT CTC      3407
Glu Arg Val Gln Ser Phe Phe Leu Arg Asn Lys Cys Arg Leu Pro Leu
1120                1125                1130                1135

AAA CCA AGT CTA GTG GCA AAA GAA CTG AAT ATT AAG TCA TGT TCG TTC      3455
Lys Pro Ser Leu Val Ala Lys Glu Leu Asn Ile Lys Ser Cys Ser Phe
                1140                1145                1150

TTC AGT TCT AAT GCT ATG CCT CTG AAA GTC ACA ATG GTG AAT GCT GAC      3503
Phe Ser Ser Asn Ala Met Pro Leu Lys Val Thr Met Val Asn Ala Asp
                1155                1160                1165

CCT CTG GGG GAA GAA ATT AAT GTC ATG TTT AAG GTT GGT GAA GAT CTT      3551
Pro Leu Gly Glu Glu Ile Asn Val Met Phe Lys Val Gly Glu Asp Leu
        1170                1175                1180

CGG CAA GAT ATG TTA GCT TTA CAG ATG ATA AAG ATT ATG GAT AAG ATC      3599
Arg Gln Asp Met Leu Ala Leu Gln Met Ile Lys Ile Met Asp Lys Ile
        1185                1190                1195

TGG CTT AAA GAG GGA CTG GAT CTG AGG ATG GTG ATA TTC AGA TGC CTG      3647
Trp Leu Lys Glu Gly Leu Asp Leu Arg Met Val Ile Phe Arg Cys Leu
1200                1205                1210                1215

TCA ACT GGC CGA GAT CGA GGC ATG GTG GAG CTA GTT CCT GCT TCA GAT      3695
Ser Thr Gly Arg Asp Arg Gly Met Val Glu Leu Val Pro Ala Ser Asp
                1220                1225                1230

ACC CTC AGG AAA ATC CAA GTG GAA TAT GGT GTA ACA GGA TCC TTT AAA      3743
Thr Leu Arg Lys Ile Gln Val Glu Tyr Gly Val Thr Gly Ser Phe Lys
        1235                1240                1245

GAT AAA CCA CTT GCT GAG TGG CTG AGG AAA TAC AAT CCT TCT GAA GAA      3791
Asp Lys Pro Leu Ala Glu Trp Leu Arg Lys Tyr Asn Pro Ser Glu Glu
        1250                1255                1260

GAA TAT GAA AAG GCT TCT GAG AAC TTT ATC TAC TCT TGT GCT GGG TGC      3839
Glu Tyr Glu Lys Ala Ser Glu Asn Phe Ile Tyr Ser Cys Ala Gly Cys
        1265                1270                1275

TGT GTA GCC ACC TAT GTT TTA GGC ATT TGT GAT CGG CAC AAT GAC AAT      3887
Cys Val Ala Thr Tyr Val Leu Gly Ile Cys Asp Arg His Asn Asp Asn
1280                1285                1290                1295

ATA ATG CTT CGA AGC ACA GGA CAC ATG TTC CAC ATT GAC TTT GGA AAG      3935
Ile Met Leu Arg Ser Thr Gly His Met Phe His Ile Asp Phe Gly Lys
                1300                1305                1310
```

```
TTT TTG GGC CAT GCA CAG ATG TTT GGT AGC TTC AAA AGG GAC CGA GCT        3983
Phe Leu Gly His Ala Gln Met Phe Gly Ser Phe Lys Arg Asp Arg Ala
            1315                1320                1325

CCT TTT GTG CTT ACC TCT GAC ATG GCG TAT GTC ATT AAT GGA GGT GAA        4031
Pro Phe Val Leu Thr Ser Asp Met Ala Tyr Val Ile Asn Gly Gly Glu
            1330                1335                1340

AAG CCC ACC ATT CGT TTC CAG TTG TTT GTG GAC CTC TGC TGT CAA GCC        4079
Lys Pro Thr Ile Arg Phe Gln Leu Phe Val Asp Leu Cys Cys Gln Ala
    1345                1350                1355

TAC AAC TTG ATA AGA AAG CAA ACA AAC CTC TTT CTT AAC CTT CTC TCA        4127
Tyr Asn Leu Ile Arg Lys Gln Thr Asn Leu Phe Leu Asn Leu Leu Ser
1360                1365                1370                1375

CTG ATG ATT CCT TCA GGA TTG CCA GAA CTC ACA AGT ATT CAG GAT CTG        4175
Leu Met Ile Pro Ser Gly Leu Pro Glu Leu Thr Ser Ile Gln Asp Leu
                1380                1385                1390

AAA TAT GTT AGA GAT GCA CTT CAG CCC CAA ACT ACA GAT GCT GAA GCT        4223
Lys Tyr Val Arg Asp Ala Leu Gln Pro Gln Thr Thr Asp Ala Glu Ala
            1395                1400                1405

ACT ATT TTC TTT ACT AGG CTG ATT GAG TCA AGT TTG GGA AGC ATT GCC        4271
Thr Ile Phe Phe Thr Arg Leu Ile Glu Ser Ser Leu Gly Ser Ile Ala
            1410                1415                1420

ACA AAG TTT AAT TTC TTC ATT CAT AAC CTT GCT CAG CTA CGT TTT TCT        4319
Thr Lys Phe Asn Phe Phe Ile His Asn Leu Ala Gln Leu Arg Phe Ser
    1425                1430                1435

GGC CTT CCT TCT AAT GAT GAG CCC ATC CTT TCA TTC TCA CCG AAA ACA        4367
Gly Leu Pro Ser Asn Asp Glu Pro Ile Leu Ser Phe Ser Pro Lys Thr
1440                1445                1450                1455

TAC TCC TTT AGA CAA GAT GGC CGG ATC AAG GAA GTC TCT GTT TTC ACA        4415
Tyr Ser Phe Arg Gln Asp Gly Arg Ile Lys Glu Val Ser Val Phe Thr
                1460                1465                1470

TAT CAT AAG AAA TAC AAC CCA GAT AAA CAC TAT ATT TAT GTG GTT CGA        4463
Tyr His Lys Lys Tyr Asn Pro Asp Lys His Tyr Ile Tyr Val Val Arg
            1475                1480                1485

ATT CTA AGA GAA GGA CAC CTT GAA CCA TCA TTT GTA TTC CGG ACA TTT        4511
Ile Leu Arg Glu Gly His Leu Glu Pro Ser Phe Val Phe Arg Thr Phe
            1490                1495                1500

GAT GAA TTT CAG GAA CTT CAC AAT AAG CTC AGT ATT ATT TTT CCT CTT        4559
Asp Glu Phe Gln Glu Leu His Asn Lys Leu Ser Ile Ile Phe Pro Leu
    1505                1510                1515

TGG AAA TTA CCT GGC TTT CCT AAT AGG ATG GTT CTT GGA AGA ACA CAC        4607
Trp Lys Leu Pro Gly Phe Pro Asn Arg Met Val Leu Gly Arg Thr His
1520                1525                1530                1535

ATA AAA GAT GTT GCA GCC AAG AGG AAA ATT GAA TTA AAC AGT TAT TTA        4655
Ile Lys Asp Val Ala Ala Lys Arg Lys Ile Glu Leu Asn Ser Tyr Leu
            1540                1545                1550

CAG AGT TTG ATG AAT GCA TCA ACA GAT GTA GCA GAG TGT GAT CTT GTT        4703
Gln Ser Leu Met Asn Ala Ser Thr Asp Val Ala Glu Cys Asp Leu Val
            1555                1560                1565

TGT ACT TTT TTC CAC CCT TTA CTT CGT GAT GAG AAA GCT GAA GGA ATA        4751
Cys Thr Phe Phe His Pro Leu Leu Arg Asp Glu Lys Ala Glu Gly Ile
            1570                1575                1580

GCT AGG TCT GCA GGT GCA GTT CCC TTC AGC CCA ACT CTG GGC CAA ATA        4799
Ala Arg Ser Ala Gly Ala Val Pro Phe Ser Pro Thr Leu Gly Gln Ile
    1585                1590                1595

GGA GGA GCA GTG AAG TTA TCT GTT TCT TAC CGA AAT GGC ACC CTC TTC        4847
Gly Gly Ala Val Lys Leu Ser Val Ser Tyr Arg Asn Gly Thr Leu Phe
1600                1605                1610                1615

ATC ATG GTG ATG CAC ATC AAA GAT CTT GTG ACT GAA GAT GGG GCT GAC        4895
Ile Met Val Met His Ile Lys Asp Leu Val Thr Glu Asp Gly Ala Asp
            1620                1625                1630
```

```
CCA AAT CCC TAT GTC AAA ACA TAC CTG CTT CCA GAT ACC CAC AAA ACG      4943
Pro Asn Pro Tyr Val Lys Thr Tyr Leu Leu Pro Asp Thr His Lys Thr
            1635                1640                1645

TCA AAA CGT AAA ACC AAA ATT TCA CGT AAA ACT AGG AAC CCA ACA TTC      4991
Ser Lys Arg Lys Thr Lys Ile Ser Arg Lys Thr Arg Asn Pro Thr Phe
        1650                1655                1660

AAT GAA ATG CTT GTA TAT AGT GGA TAC AGC AAA GAA ACT CTG AGG CAG      5039
Asn Glu Met Leu Val Tyr Ser Gly Tyr Ser Lys Glu Thr Leu Arg Gln
    1665                1670                1675

AGA GAA CTT CAA CTG AGT GTA CTC AGT GCA GAA TCA CTG CGG GAG AAT      5087
Arg Glu Leu Gln Leu Ser Val Leu Ser Ala Glu Ser Leu Arg Glu Asn
1680                1685                1690                1695

TTC TTC TTG GGT GGA ATA ACC CTG CCA CTG AAA GAT TTC AAC TTG AGC      5135
Phe Phe Leu Gly Gly Ile Thr Leu Pro Leu Lys Asp Phe Asn Leu Ser
                1700                1705                1710

AAA GAG ACA GTT AAG TGG TAT CAG CTG ACT GCG GCA ACG TAT CTA TAA      5183
Lys Glu Thr Val Lys Trp Tyr Gln Leu Thr Ala Ala Thr Tyr Leu
            1715                1720                1725

ACT TCC GAC TTC TGA GCT TTG GAA ACA AGG AGT TAT AAA TGT GTG CGC      5231
Thr Ser Asp Phe     Ala Leu Glu Thr Arg Ser Tyr Lys Cys Val Arg
        1730                1735                1740

ATG CGC ACA TAC ACA CAC TTG GGA ACT TTG TAT AAT TTC ATA CTT TGG      5279
Met Arg Thr Tyr Thr His Leu Gly Thr Leu Tyr Asn Phe Ile Leu Trp
    1745                1750                1755

CAG CCC                                                               5285
Gln Pro
1760

(2) INFORMATION FOR SEQ ID NO:30:

(i) SEQUENCE CHARACTERISTICS:
        (A) LENGTH: 1726 amino acids
        (B) TYPE: amino acid
        (D) TOPOLOGY: linear (ii) MOLECULE TYPE: protein (xi) SEQUENCE DESCRIPTION: SEQ ID NO:30:

Gln Ser Ser Ala Gly Arg Gly Val Ser Arg Ser Ser Pro Gln Arg Pro
1               5                   10                  15

Ala Glu Pro Ala Glu Ala Gly Glu Lys His Gly Ser Asp Leu Gly Gly
            20                  25                  30

Arg Glu Gly Ser Gly Cys Gly Glu Asp Gln Asp Ser Arg Ser Val Arg
        35                  40                  45

Ser Trp Tyr Phe Gly Ser Tyr Lys Lys Arg Leu Arg Gly Leu Phe
    50                  55                  60

Ser Phe Val Asp Met Ala Gln Ile Ser Asn Asn Ser Glu Phe Lys Gln
65                  70                  75                  80

Cys Ser Ser Ser His Pro Glu Pro Ile Arg Thr Lys Asp Val Asn Lys
                85                  90                  95

Ala Glu Ala Leu Gln Met Glu Ala Glu Ala Leu Ala Lys Leu Gln Lys
            100                 105                 110

Asp Arg Gln Met Thr Asp Ser Pro Arg Gly Phe Glu Leu Ser Ser Ser
        115                 120                 125

Thr Arg Gln Arg Thr Gln Gly Phe Asn Lys Gln Asp Tyr Asp Leu Met
    130                 135                 140

Val Phe Pro Glu Leu Asp Ser Gln Lys Arg Ala Val Asp Ile Asp Val
145                 150                 155                 160
```

-continued

```
Glu Lys Leu Thr Gln Ala Glu Leu Glu Lys Ile Leu Leu Asp Asp Asn
            165                 170                 175

Phe Glu Thr Arg Lys Pro Pro Ala Leu Pro Val Thr Pro Val Leu Ser
            180                 185                 190

Pro Ser Phe Ser Thr Gln Leu Tyr Leu Arg Pro Ser Gly Gln Arg Gly
            195                 200                 205

Gln Trp Pro Pro Gly Leu Cys Gly Pro Ser Thr Tyr Thr Leu Pro Ser
            210                 215                 220

Thr Tyr Pro Ser Ala Tyr Ser Lys Gln Ala Thr Phe Gln Asn Gly Phe
225                 230                 235                 240

Ser Pro Arg Met Pro Thr Phe Pro Ser Thr Glu Ser Val Tyr Leu Arg
            245                 250                 255

Leu Pro Gly Gln Ser Pro Tyr Phe Ser Tyr Pro Leu Thr Pro Ala Thr
            260                 265                 270

Pro Phe His Pro Gln Gly Ser Leu Pro Val Tyr Arg Pro Leu Val Ser
            275                 280                 285

Pro Asp Met Ala Lys Leu Phe Glu Lys Ile Ala Ser Thr Ser Glu Phe
290                 295                 300

Leu Lys Asn Gly Lys Ala Arg Thr Asp Leu Glu Ile Ala Asn Ser Lys
305                 310                 315                 320

Ala Ser Val Cys Asn Leu Gln Ile Ser Pro Lys Ser Glu Asp Ile Asn
            325                 330                 335

Lys Phe Asp Trp Leu Asp Leu Asp Pro Trp Asp Ala Val Leu Leu Glu
            340                 345                 350

Glu Arg Ser Pro Ser Cys His Leu Glu Arg Lys Val Asn Gly Lys Ser
            355                 360                 365

Leu Ser Gly Ala Thr Val Thr Arg Ser Gln Ser Leu Ile Ile Arg Thr
            370                 375                 380

Ala Gln Phe Thr Lys Ala Gln Gly Gln Val Ser Gln Lys Asp Pro Asn
385                 390                 395                 400

Gly Thr Ser Ser Leu Pro Thr Gly Ser Ser Leu Leu Gln Glu Phe Glu
            405                 410                 415

Val Gln Asn Asp Glu Val Ala Ala Phe Cys Gln Ser Ile Met Lys Leu
            420                 425                 430

Lys Thr Lys Phe Pro Tyr Thr Asp His Cys Thr Asn Pro Gly Tyr Leu
            435                 440                 445

Leu Ser Pro Val Thr Val Gln Arg Asn Met Cys Gly Glu Asn Ala Ser
            450                 455                 460

Val Lys Val Ser Ile Glu Ile Glu Gly Leu Gln Leu Pro Val Thr Phe
465                 470                 475                 480

Thr Cys Asp Val Ser Ser Thr Val Glu Ile Ile Met Gln Ala Leu
                485                 490                 495

Ser Trp Val His Asp Asp Leu Asn Gln Val Asp Val Gly Ser Tyr Ile
            500                 505                 510

Leu Lys Val Cys Gly Gln Glu Val Leu Gln Asn His Cys Leu
            515                 520                 525

Gly Ser His Glu His Ile Gln Asn Cys Arg Lys Trp Asp Thr Glu Ile
            530                 535                 540

Lys Leu Gln Leu Leu Thr Leu Ser Ala Met Cys Gln Asn Leu Ala Arg
545                 550                 555                 560

Thr Ala Glu Asp Asp Glu Ala Pro Val Asp Leu Asn Lys Tyr Leu Tyr
            565                 570                 575

Gln Ile Glu Lys Pro Tyr Lys Glu Val Met Thr Arg His Pro Val Glu
```

-continued

```
                    580                 585                 590
    Glu Leu Leu Asp Ser Tyr His Tyr Gln Val Glu Leu Ala Leu Gln Thr
                595                 600                 605
    Glu Asn Gln His Arg Ala Val Asp Gln Val Ile Lys Ala Val Arg Lys
                610                 615                 620
    Ile Cys Ser Ala Leu Asp Gly Val Glu Thr Pro Ser Val Thr Glu Ala
    625                 630                 635                 640
    Val Lys Lys Leu Lys Arg Ala Val Asn Leu Pro Arg Asn Lys Ser Ala
                    645                 650                 655
    Asp Val Thr Ser Leu Ser Gly Ser Asp Thr Arg Lys Asn Ser Thr Lys
                    660                 665                 670
    Gly Ser Leu Asn Pro Glu Asn Pro Val Gln Val Ser Met Asp His Leu
                    675                 680                 685
    Thr Thr Arg Ile Tyr Asp Leu Leu Arg Leu His Ala Asn Ser Ser Arg
                    690                 695                 700
    Cys Ser Thr Gly Cys Pro Arg Gly Ser Arg Asn Ile Lys Glu Ala Trp
    705                 710                 715                 720
    Thr Ala Thr Glu Gln Leu Gln Phe Thr Val Tyr Ala Ala His Gly Ile
                    725                 730                 735
    Ser Ser Asn Trp Val Ser Asn Tyr Glu Lys Tyr Tyr Leu Ile Cys Ser
                    740                 745                 750
    Leu Ser His Asn Gly Lys Asp Leu Phe Lys Pro Ile Gln Ser Lys Lys
                    755                 760                 765
    Val Gly Thr Tyr Lys Asn Phe Phe Tyr Leu Ile Lys Trp Asp Glu Leu
            770                 775                 780
    Ile Ile Phe Pro Ile Gln Ile Ser Gln Leu Pro Leu Glu Ser Val Leu
    785                 790                 795                 800
    His Leu Thr Leu Phe Gly Val Leu Asn Gln Ser Ser Gly Ser Ser Pro
                    805                 810                 815
    Asp Ser Asn Lys Gln Arg Lys Gly Pro Glu Ala Leu Gly Lys Val Ser
                    820                 825                 830
    Leu Thr Leu Phe Asp Phe Lys Arg Phe Leu Thr Cys Gly Thr Lys Leu
                    835                 840                 845
    Leu Tyr Leu Trp Thr Ser Ser His Thr Asn Ser Ile Pro Gly Ala Ile
                    850                 855                 860
    Pro Lys Lys Ser Tyr Val Met Glu Arg Ile Val Leu Gln Val Asp Phe
    865                 870                 875                 880
    Pro Ser Pro Ala Phe Asp Ile Ile Tyr Thr Ser Pro Gln Ile Asp Arg
                            885                 890                 895
    Asn Ile Ile Gln Gln Asp Lys Leu Glu Thr Leu Glu Ser Asp Ile Lys
                    900                 905                 910
    Gly Lys Leu Leu Asp Ile Ile His Arg Asp Ser Ser Phe Gly Leu Ser
                    915                 920                 925
    Lys Glu Asp Lys Val Phe Leu Trp Glu Asn Arg Tyr Tyr Cys Leu Lys
                    930                 935                 940
    His Pro Asn Cys Leu Pro Lys Ile Leu Ala Ser Ala Pro Asn Trp Lys
    945                 950                 955                 960
    Trp Ala Asn Leu Ala Lys Thr Tyr Ser Leu Leu His Gln Trp Pro Pro
                    965                 970                 975
    Leu Cys Pro Leu Ala Ala Leu Glu Leu Leu Asp Ala Lys Phe Ala Asp
                    980                 985                 990
    Gln Gly Val Arg Ser Leu Ala Val Ser Trp Met Glu Ala Ile Ser Asp
                    995                 1000                1005
```

-continued

```
Asp Glu Leu Ala Asp Leu Leu Pro Gln Phe Val Gln Ala Leu Lys Tyr
    1010                1015                1020
Glu Ile Tyr Leu Asn Ser Ser Leu Val Arg Phe Leu Leu Ser Arg Ala
1025                1030                1035                1040
Leu Gly Asn Ile Gln Ile Ala His Ser Leu Tyr Trp Leu Leu Lys Asp
                1045                1050                1055
Ala Leu His Asp Thr His Phe Gly Ser Arg Tyr Glu His Val Leu Gly
                1060                1065                1070
Ala Leu Leu Ser Val Gly Gly Lys Gly Leu Arg Glu Glu Leu Ser Lys
                1075                1080                1085
Gln Met Lys Leu Val Gln Leu Leu Gly Val Ala Glu Lys Val Arg
    1090                1095                1100
Gln Ala Ser Gly Ser Thr Arg Gln Val Val Leu Gln Lys Ser Met Glu
1105                1110                1115                1120
Arg Val Gln Ser Phe Phe Leu Arg Asn Lys Cys Arg Leu Pro Leu Lys
                1125                1130                1135
Pro Ser Leu Val Ala Lys Glu Leu Asn Ile Lys Ser Cys Ser Phe Phe
                1140                1145                1150
Ser Ser Asn Ala Met Pro Leu Lys Val Thr Met Val Asn Ala Asp Pro
                1155                1160                1165
Leu Gly Glu Glu Ile Asn Val Met Phe Lys Val Gly Glu Asp Leu Arg
    1170                1175                1180
Gln Asp Met Leu Ala Leu Gln Met Ile Lys Ile Met Asp Lys Ile Trp
1185                1190                1195                1200
Leu Lys Glu Gly Leu Asp Leu Arg Met Val Ile Phe Arg Cys Leu Ser
                1205                1210                1215
Thr Gly Arg Asp Arg Gly Met Val Glu Leu Val Pro Ala Ser Asp Thr
                1220                1225                1230
Leu Arg Lys Ile Gln Val Glu Tyr Gly Val Thr Gly Ser Phe Lys Asp
                1235                1240                1245
Lys Pro Leu Ala Glu Trp Leu Arg Lys Tyr Asn Pro Ser Glu Glu Glu
    1250                1255                1260
Tyr Glu Lys Ala Ser Glu Asn Phe Ile Tyr Ser Cys Ala Gly Cys Cys
1265                1270                1275                1280
Val Ala Thr Tyr Val Leu Gly Ile Cys Asp Arg His Asn Asp Asn Ile
                1285                1290                1295
Met Leu Arg Ser Thr Gly His Met Phe His Ile Asp Phe Gly Lys Phe
                1300                1305                1310
Leu Gly His Ala Gln Met Phe Gly Ser Phe Lys Arg Asp Arg Ala Pro
                1315                1320                1325
Phe Val Leu Thr Ser Asp Met Ala Tyr Val Ile Asn Gly Gly Glu Lys
                1330                1335                1340
Pro Thr Ile Arg Phe Gln Leu Phe Val Asp Leu Cys Cys Gln Ala Tyr
1345                1350                1355                1360
Asn Leu Ile Arg Lys Gln Thr Asn Leu Phe Leu Asn Leu Leu Ser Leu
                1365                1370                1375
Met Ile Pro Ser Gly Leu Pro Glu Leu Thr Ser Ile Gln Asp Leu Lys
                1380                1385                1390
Tyr Val Arg Asp Ala Leu Gln Pro Gln Thr Thr Asp Ala Glu Ala Thr
                1395                1400                1405
Ile Phe Phe Thr Arg Leu Ile Glu Ser Ser Leu Gly Ser Ile Ala Thr
                1410                1415                1420
```

```
Lys Phe Asn Phe Phe Ile His Asn Leu Ala Gln Leu Arg Phe Ser Gly
1425                1430                1435                1440

Leu Pro Ser Asn Asp Glu Pro Ile Leu Ser Phe Ser Pro Lys Thr Tyr
                1445                1450                1455

Ser Phe Arg Gln Asp Gly Arg Ile Lys Glu Val Ser Val Phe Thr Tyr
                1460                1465                1470

His Lys Lys Tyr Asn Pro Asp Lys His Tyr Ile Tyr Val Val Arg Ile
            1475                1480                1485

Leu Arg Glu Gly His Leu Glu Pro Ser Phe Val Phe Arg Thr Phe Asp
1490                1495                1500

Glu Phe Gln Glu Leu His Asn Lys Leu Ser Ile Ile Phe Pro Leu Trp
1505                1510                1515                1520

Lys Leu Pro Gly Phe Pro Asn Arg Met Val Leu Gly Arg Thr His Ile
                1525                1530                1535

Lys Asp Val Ala Ala Lys Arg Lys Ile Glu Leu Asn Ser Tyr Leu Gln
                1540                1545                1550

Ser Leu Met Asn Ala Ser Thr Asp Val Ala Glu Cys Asp Leu Val Cys
                1555                1560                1565

Thr Phe Phe His Pro Leu Leu Arg Asp Glu Lys Ala Glu Gly Ile Ala
1570                1575                1580

Arg Ser Ala Gly Ala Val Pro Phe Ser Pro Thr Leu Gly Gln Ile Gly
1585                1590                1595                1600

Gly Ala Val Lys Leu Ser Val Ser Tyr Arg Asn Gly Thr Leu Phe Ile
                1605                1610                1615

Met Val Met His Ile Lys Asp Leu Val Thr Glu Asp Gly Ala Asp Pro
                1620                1625                1630

Asn Pro Tyr Val Lys Thr Tyr Leu Leu Pro Asp Thr His Lys Thr Ser
                1635                1640                1645

Lys Arg Lys Thr Lys Ile Ser Arg Lys Thr Arg Asn Pro Thr Phe Asn
1650                1655                1660

Glu Met Leu Val Tyr Ser Gly Tyr Ser Lys Glu Thr Leu Arg Gln Arg
1665                1670                1675                1680

Glu Leu Gln Leu Ser Val Leu Ser Ala Glu Ser Leu Arg Glu Asn Phe
                1685                1690                1695

Phe Leu Gly Gly Ile Thr Leu Pro Leu Lys Asp Phe Asn Leu Ser Lys
                1700                1705                1710

Glu Thr Val Lys Trp Tyr Gln Leu Thr Ala Ala Thr Tyr Leu
                1715                1720                1725

(2) INFORMATION FOR SEQ ID NO:31:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:31:

Thr Ser Asp Phe (2) INFORMATION FOR SEQ ID NO:32:

(i) SEQUENCE CHARACTERISTICS:
        (A) LENGTH: 29 amino acids
        (B) TYPE: amino acid
        (D) TOPOLOGY: linear
```

-continued

```
    (ii) MOLECULE TYPE: protein (xi) SEQUENCE DESCRIPTION: SEQ ID NO:32:

Ala Leu Glu Thr Arg Ser Tyr Lys Cys Val Arg Met Arg Thr Tyr Thr
                  5                  10                  15

His Leu Gly Thr Leu Tyr Asn Phe Ile Leu Trp Gln Pro
             20                  25
```

POLYNUCLEOTIDES ENCODING PHOSPHATIDYLINOSITOL 3-KINASES

This application is a division of and claims the benefit of U.S. application Ser. No. 08/609,049, filed Feb. 12, 1996, now U.S. Pat. No. 5,948,664 the disclosure of which is incorporated by reference in its entirety for all purposes.

BACKGROUND OF THE INVENTION

Phosphatidyl Inositol kinases ("PtdIns-kinases") regulate diverse cellular processes including cell signaling, cell cycle progression, and intracellular protein sorting. See, e.g., Herman et al., Nature 358:157–159 (1992), Kapellar et al., Bioessays 16:565–576 (1994), Stephens et al., Nature 351:33–39 (1991) and Kunz et al., Cell 73:585–596 (1993). PtdIns-kinases phosphorylate phosphoinositol lipids at distinct positions on the inositol ring. For example, PtdIns 3-kinases, or "PI 3-kinases", phosphorylate the D3 hydroxyl group on the inositol ring, while PtdIns 4-kinases phosphorylate the D4 hydroxyl group. All of the PtdIns kinases that have been identified to date have been found to contain a core region of sequence similarity, which, without being bound to any particular theory, is believed to be the catalytic domain. This domain, termed the "PtdIns kinase domain", shares limited sequence similarity with the catalytic domain of protein kinases and mutation of conserved residues results in loss of PtdIns kinase activity. See, Carter et al., J. Biochem. 301:415–420 (1994), Dhand et al., EMBO J. 13:522–533 (1994) and Schu et al., Science 260:88–91 (1993).

A number of receptor tyrosine kinases, src-like tyrosine kinases and viral oncoproteins bind and activate one particular cellular PtdIns 3-kinase. Studies of mutants that abrogate the binding of this PtdIns 3-kinase to these molecules indicate that PtdIns 3-kinases mediate mitogenic and cell motility responses of cells to growth factors and oncoproteins. Purification of the polypeptide subunits of this PtdIns 3-kinase reveal that the enzyme exists as a heterodimeric complex composed of a 110 Kd and an 85 Kd subunit. Carpenter et al., J. Biol. Chem. 265:19704–19711 (1990), Fry et al., Biochem. J. 288:383–393 (1992), Morgan et al., Eur. J. Biochem. 191:761–767 (1990), Shibasaki et al., J. Biol. Chem. 266:8108–8114 (1991). The 110 Kd subunit contains a C-terminal PtdIns kinase domain, as well as a small domain at its N-terminus that is sufficient for binding to the 85-Kd subunit (Hiles et al., Cell 70:419–429 (1992), Holt et al., Mol. Cell. Biol. 14:42–49 (1994), Klippel et al., Mol. Cell. Biol. 14:2675–2685 (1994). The 85 Kd subunit serves as an adapter and binds activated growth factor receptors and other tyrosine phosphorylated molecules through two Src homology 2 (SH2) domains. Hu et al., Mol. Cell. Biol. 12:981–990 (1992), McGlade et al., Mol. Cell. Biol. 12:991–997 (1992) Reedijk et al., EMBO J. 11:1365–1372 (1992), Yoakim, J. Virol. 66:5485–5491 (1992), Yonezawa et al., J. Biol. Chem. 267:25958–25966 (1992). The association of the enzyme with activated growth factor receptors is believed to localize it to the plasma membrane where its phospholipid substrates reside.

The p110/p85 complex phosphorylates distinct lipids in vitro and in vivo. In vitro, the p110/p85 complex can phosphorylate phosphatidylinositol (PtdIns), phosphatidylinositol 4-phosphate (PtdIns4P) and phophatidylinositol 4,5-bisphosphate (PtdIns(4,5)$P_2$) on the D3 hydroxyl group of the inositol ring, producing phosphatidylinositol 3-phosphate (PtdIns3P), phosphatidylinositol 3,4-bisphosphate (PtdIns(3,4)$P_2$) and phosphatidylinositol 3,4,5-trisphosphate (PtdIns(3,4,5)$P_3$). Kapellar et al., Bioessays 16:565–576 (1994), Stephens et al., Biochim. Biophys. Acta 1179:27–75 (1993). Activation of the p110/p85 complex in cells results in elevated levels of PtdIns(3,4)$P_2$ and PtdIns (3,4,5)$P_3$, but not PtdIns3P. Auger et al., Cell 57:167–175 (1989), Stephens et al., Nature 351:33–39 (1991), Traynor-Kaplan et al., Nature 334:353–356 (1988), Traynor-Kaplan J. Biol. Chem. 264:15668–15673 (1989). Studies of the pathways in cells that generate these lipids suggest that PtdIns(3,4)$P_2$ is formed by the dephosphorylation of PtdIns (3,4,5)$P_3$ by a PtdIns 5-phosphatase rather than the phosphorylation of PtdIns4P by a PtdIns 3-kinase. Carter et al., Biochem. J. 301:415–420 (1994), Hawkins et al., Nature 358:157–159 (1992).

The stimulation of cells with growth factors or tumor antigens results in a rapid increase in the cellular concentration of PtdIns(3,4)$P_2$ and PtdIns(3,4,5)$P_3$ from a low basal level, indicating that these molecules represent novel second messengers in growth factor activated signaling cascades.

Additionally, several protein kinases have recently been described which appear to represent downstream effectors of the lipid products of PtdIns 3-kinases. The Akt protein kinase can be activated in vivo by treating cells with the mitogen PDGF. The binding of PtdIns 3-kinase to the PDGF receptor is essential for Akt activation (Franke et al., Cell 81:727–736 (1995)). Akt can be directly activated in vitro with PtdIns3P. In addition to Akt, particular isoforms of protein kinase C can be activated by the lipid products of PtdIns 3-kinases. Protein kinase C isoforms $\delta$, $\epsilon$, $\eta$, and $\zeta$ can be activated in vitro with PtdIns(3,4)$P_2$ or PtdIns(3,4,5)$P_3$, but not with PtdIns3P. Nakanishi et al., J. Biol. Chem. 268:13–16 (1993), Toker et al., J. Biol. Chem 269:32358–32367 (1994).

PtdIns 3-kinases have also been implicated in the regulation of intracellular protein sorting. For example, the Vps34 PtdIns 3-kinase was initially identified from a *Saccharomyces cerevisiae* mutant that was defective in the trafficking of proteins to the lysosome-like vacuole. Herman et al., Mol. Cell. Biol. 10:6742–6754 (1990). Vps34 can phosphorylate PtdIns, but not PtdIns4P or PtdIns(4,5)$P_2$ in vitro, which is consistent with absence of detectable PtdIns (3,4,5)$P_3$ in yeast. Schu et al., Science 260:89–91 (1993). Vps34 is the major PtdIns 3-kinase in yeast. VPS34 mutant strains contain no detectable PtdIns3P.

Because disregulation of the cellular processes, such as signaling processes involved in cell cycle progression and intracellular protein sorting, can have disastrous effects, it is important to understand and gain control over these processes. This requires identifying the participants in the signaling events involved in these processes and elucidating their mechanism of function. The identification of these participants is important for a wide range of diagnostic, therapeutic and screening applications. In particular, by knowing the structure and function of a particular participant in a signaling cascade, one can design compounds which affect that cascade, to either activate an otherwise inactive pathway, or inactivate an overly active pathway. Similarly, having identified a particular participant in a signaling cascade, one can also identify situations where that cascade is defective, resulting in a particular pathological state.

PI3-kinases have been identified as playing critical roles in several distinct cellular signaling processes. As a result, it is of particular interest to identify these kinases, their substrates, products and effectors. Once identified, these various elements can be used for a variety of therapeutic, diagnostic and screening applications. For example, these components may be used as therapeutic agents for treating disorders resulting from anomalies in signaling cascades. Alternatively, these components may be used alone or in combination, as model systems for screening compounds that affect signaling cascades. Finally, identification of these components leads to an understanding of the cell signaling processes, anomalies in these processes which are responsible for certain disorders, and by implication, diagnostic systems for identifying these disorders. The present invention meets these and many other needs.

SUMMARY OF THE INVENTION

The present invention generally provides novel PI3-kinase polypeptides, nucleic acids encoding these polypeptides, antibodies that are specifically immunoreactive with these polypeptides and methods of using these polypeptides in screening and therapeutic applications.

In one aspect, the present invention provides substantially pure PI3-kinase polypeptides or biologically active fragments thereof. These polypeptides are generally characterized by their ability to phosphorylate the D3 hydroxyl of an inositol ring in PtdIns and PtdIns4P but not PtdIns(4,5)P$_2$. The polypeptides may further include a C2 domain within their structure. In a more specific aspect, the polypeptides of the invention have an amino acid sequence that is substantially homologous to the sequence of cpk and cpk-m, as shown in FIG. 1 (SEQ ID NOS:12–13), or biologically active fragments thereof.

The polypeptides may, in some aspects, be characterized by their ability to block the interaction between a cpk or cpk-m polypeptide and an antibody that is specifically immunoreactive with cpk or cpk-m. Similarly, the polypeptides may be characterized by their ability to block the interaction between a cpk and/or cpk-m polypeptide and its substrate, such as PtdIns or PtdIns4P.

In another aspect, the present invention provides nucleic acids that encode the polypeptides of the invention. In particular, the nucleic acids of the present invention will typically encode polypeptides which possess the above-described substrate specificity, or biologically active fragments. In a more specific aspect, the nucleic acids of the present invention will have a nucleic acid sequence that is substantially homologous to the nucleic acid sequence for cpk or cpk-m, as shown in FIG. 9 (SEQ ID NOS:27–28). In a related aspect, the present invention provides nucleic acid probes that have at least 15 contiguous nucleotides from the cpk or cpk-m nucleic acid sequences. The present invention also provides expression vectors containing the nucleic acids of the invention, and recombinant host cells that are capable of expressing these nucleic acids.

In a further aspect, the present invention provides methods of using the polypeptides of the present invention. In particular, the present invention provides a method of screening test compounds to identify agonists or antagonists of PI3-kinases and the signalling pathways they control. The methods comprise incubating a mixture of PtdIns or PtdIns4P and a polypeptide selected from the group consisting of cpk, cpk-m or biologically active fragments thereof, in the presence and absence of the test compound. The mixture is assayed to determine the amount of PtdIns3P or PtdIns(3,4)P$_2$ produced in the presence and absence of the test compound. The amount of PtdIns3P or PtdIns(3,4)P$_2$ produced in the presence of the test compound is compared to the amount of PtdIns3P or PtdIns(3,4)P$_2$ produced in the absence of the test compound. An increase or decrease in the amount of PtdIns3P or PtdIns(3,4)P$_2$ in the presence of the test compound is indicative that the test compound is an agonist or antagonist of a PI3-kinase activity, respectively.

The present invention also provides therapeutic methods for treating a symptom of a disorder caused by the dysregulation of a growth factor activation signaling cascade. These methods generally comprise administering to a patient suffering from the disorder, a therapeutically effective amount of a polypeptide or blocking antibody of the present invention.

BRIEF DESCRIPTION OF THE DRAWINGS

FIG. 1 shows a comparison of the amino acid sequences of the Drosophila and murine cpk proteins (SEQ ID NOS:12–13)respectively. Both conserved and identical residues are shaded. The following groups of amino acids were considered to be conserved: A, V, L, I, M; D, E; K, R; N, Q; F, Y; S, T. The amino acid numbers are indicated to the right of the sequence.

FIGS. 2A, 2B and 2C show the domain structure of the cpk proteins. FIG. 2A shows a schematic ribbon diagram comparing the domain structures of cpk with p110, Tor2, Pik1 and Vps34 PtdIns kinases. The PtdIns kinase domains are depicted in black, a region in which cpk and plo are related is depicted with stripes, and the C2 domain and p85 binding domains are indicated. FIG. 2B shows a comparison of the amino acid sequence of the C2 domains in Drosophila and murine cpk (SEQ ID NOS:14–18) with the C2 domains in rabphilin ("rab") (SEQ ID NO:16), synaptotagmin II ("syt II") (SEQ ID NO:17), and protein kinase C ("pkc") (SEQ ID NO:18). Both conserved and identical residues are shaded. FIG. 2C shows a comparison of the amino acid sequences of a part of the catalytic domains of cpk (SEQ ID NO:19) and cpk-m (SEQ ID NO:20) with the catalytic domains of p110α (SEQ ID NO:20), p110β (SEQ ID NO:22), p110γ (SEQ ID NO:23), Vps34 (SEQ ID NO:24), Pik1 (SEQ ID NO:25) and Tor2 (SEQ ID NO:26). Only identical amino acids are indicated, i.e., shaded/boxed. The amino acid numbers are indicated to the right of the sequence.

FIG. 3A is an immunoblot of lysates (30 µg) prepared from 0–12 hr Drosophila embryos probed with α-cpk polyclonal serum. FIG. 3B illustrates the precipitation of cpk protein from embryo lysates. Lysates were precipitated with α-cpk preimmune (lane 1), α-cpk immune (lane 2), α-P6 preimmune (lane 3), and α-P6 immune sera (lane 4). Preimmune and immune sera are indicated by P and I, respectively.

FIG. 5A is an immunoblot of lysates prepared from 0–12 hr Drosophila embryos precipitated with α-cpk preimmune serum (lane 1), α-cpk immune serum (lane 2), α-P6 preimmune serum (lane 4), or α-P6 immune serum (lane 5). Precipitates were divided in half and half was assayed for PI 3-kinase activity by thin layer chromatography (left panel). Lysates were also precipitated with α-cpk serum which had been preincubated with cpk protein (lane 3) or α-P6 serum which had been preincubated with the P6 peptide (lane 6). FIG. 5B is a blot and TLC (left) showing wild-type (lane 1) and kinase deficient (lane 2) cpk proteins which had been tagged with an HA epitope were expressed in COS-7 cells. P and I indicate preimmune and immune sera, respectively. $I^c$ represents either α-cpk or α-P6 sera which had been preincubated for 10 min. with 0.5 μg of competitor (cpk and P6, respectively).

FIG. 8A shows an immunoblot of lysates (30 μg) prepared from 0–12 hr Drosophila embryos and probed with α-cpk.m1 serum. FIG. 8B shows the visualization of 90 Kd and 190 Kd proteins which were coprecipitated with cpk. Drosophila lysates were precipitated with Protein A beads alone (1) or beads upon which α-cpk.m1 had previously been immobilized (2). FIG. 8C shows a blot probed with α-phosphotyrosine showing that both cpk and the 190 Kd protein may be tyrosine phosphorylated.

FIG. 9 shows the nucleic acid sequence and deduced amino acid sequence of cpk (SEQ ID NOS:27–28 respectively).

FIG. 10 shows the nucleic acid sequence (SEQ ID NO:29) and deduced amino acid sequences of cpk-m (SEQ ID NOS:30–32).

DESCRIPTION OF THE PREFERRED EMBODIMENT

I. Abbreviations

Figures 2A, 2B:
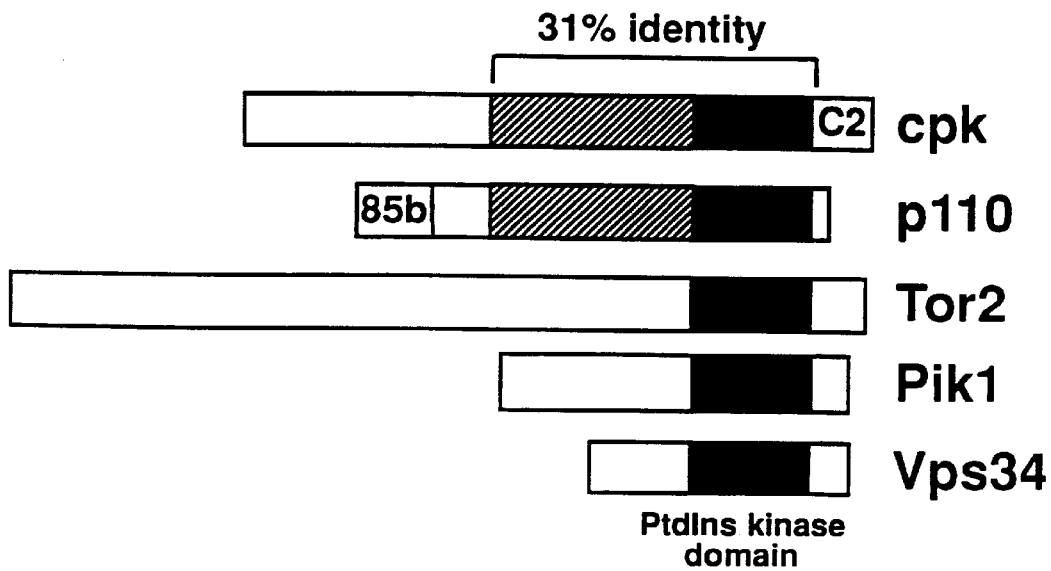

The various embodiments of the present invention may be described with reference to certain abbreviations. Several of the most commonly used abbreviations are as follows:

| | |
|---|---|
| PtdIns | PhosphatidylInositol |
| PtdIns-4P | PhosphatidylInositol 4-phosphate |
| PtdIns(4,5)P$_2$ | PhosphatidylInositol 4,5-bisphosphate |
| PtdIns-Kinase | PhosphatidylInositol kinase (also referred to as PI-kinase) |
| PI3-kinase | PhosphatidylInositol 3-kinase |

II. General Description

The present invention generally provides polypeptides that are related to and/or derived from the family of PI3-kinases. These polypeptides are generally involved in cell signaling cascades which control various cellular processes including cell cycle progression and intracellular protein sorting. The family of PI3-kinases from which the polypeptides of the invention are derived are generally characterized by their structure as well as their unique substrate specificity.

The present invention also provides nucleic acids encoding the above-described PI3-kinase polypeptides, antibodies that are capable of interacting with these polypeptides and methods of utilizing these polypeptides in screening systems for identification of agonists or antagonists of cell signaling pathways, generally, and PtdIns phosphorylation, specifically.

III. Proteins and Polypeptides of the Invention

In a first aspect, the present invention provides isolated, or substantially pure polypeptides that are derived from the family of PI3-kinases. The terms "substantially pure" or "isolated", when referring to proteins and polypeptides, denote those polypeptides that are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up from about 75 to about 90% of the total protein. Preferably, the protein will make up greater than about 90%, and more preferably, greater than about 95% of the total protein in the composition.

The polypeptides of the present invention are typically derived from PI3-kinases that include a C2 domain within their structure. A C2 domain is generally characterized by its structure, e.g., its homology to similar domains in other proteins, is generally believed to mediate binding to phospholipids or other proteins. The PI3-kinases from which the polypeptides of the present invention are derived may be further characterized by their substrate specificity. In particular, the PI3-kinases from which the polypeptides of the present invention are derived have PI3-kinase activity and are capable of phosphorylating the D3 hydroxyl group on the inositol ring of PtdIns and PtdIns4P, but not PtdIns (4,5)P$_2$.

The polypeptides may be further characterized by their relation to a PtdIns 3-kinase isolated from *Drosophila melanogaster*. This Drosophila PI3-kinase contains a C2 domain and is therefore generally referred to herein as "cpk" for C2 containing PtdIns kinase. The cpk gene represents the first PI3-kinase identified from Drosophila. Additional preferred polypeptides are characterized by their relation to a similar PI3-kinase identified from murine sources, termed cpk-m, which contains a C2 domain and shares extensive sequence identity with cpk. The cpk and cpk-m polypeptides represent a new class of PtdIns 3-kinases. The deduced amino acid sequences for the cpk and cpk-m kinases are shown in FIG. 1.

Analysis of the sequence of the Drosophila and murine cpk proteins reveals a similarity to the p110 family of PtdIns 3-kinases. The cpk genes are 31% identical and 43% similar to a large central region of p110. This region includes both the PtdIns kinase domain (FIG. 2A, black box) and an adjacent region in which p110and cpk can be distinguished from other PtdIns kinases (striped box). The cpk proteins are also similar to p110 family of PtdIns kinases in the most conserved portion of the catalytic domain (FIG. 2C) (SEQ ID NOS:19–26). In this region, the cpk proteins share approximately 45–50% identity with either p110α, p110β or p110γ. In contrast, the cpk proteins share 35%, 29% and 26% identity in this region with the Vps34, Pik1, and Tor2 PtdIns kinases, respectively.

The cpk proteins differ from p110 at both their N- and C-termini. The N-termini of the cpk and cpk-m proteins do not contain any recognizable domain, i.e., the N-terminal domain of p110 that is responsible for binding to the p85 adapter molecule (Holt et al., Mol. Cell. Biol. 14:42–49 (1994), Klippel et al., Mol. Cell Biol. 14:2675–2685 (1994)). The C-termini of cpk and cpk-m proteins contain a "C2" domain (FIG. 2C). These C2 domains are found in a diverse group of proteins and are believed to mediate binding to phospholipids or other proteins. The C2 domains in the cpk and cpk-m sequences are 52% similar to each other, and approximately 38% similar to C2 domains present in protein kinase C, synaptotagmin and rabphilin (FIG. 2B) (SEQ ID NOS:14–18).

α-cpk immune serum recognizes a polypeptide from Drosophila lysates which migrates at approximately 210 Kd, the predicted molecular weight of the cpk protein (FIG. 3). This 210 Kd polypeptide is not recognized by pre-immune serum. Further studies using antibodies raised against fragments of cpk have confirmed the identity of the 210 kD polypeptide as cpk.

Preferred polypeptides of the present invention will be derived from PI3-kinases having amino acid sequences that are substantially homologous to the amino acid sequences shown in FIG. 1 or biologically active fragments thereof.

The term "biologically active fragment" as used herein, refers to portions of the proteins or polypeptides, which portions possess a particular biological activity. For example, such biological activity may include the ability to bind a particular protein, substrate or ligand, to have antibodies generated against it, to block or otherwise inhibit an interaction between two proteins, between an enzyme and its substrate, between an epitope and an antibody, or may include a particular catalytic activity. With regard to the polypeptides of the present invention, particularly preferred polypeptides or biologically active fragments include, e.g., polypeptides that possess one or more of the biological activities described above, such as the ability to interact with the PI3-kinase substrates described above, e.g., PtdIns and PtdIns4P, or the ability to affect the phosphorylation of those substrates. Fragments possessing this catalytic activity are also termed "catalytically active fragments." Fragments that are specifically recognized and bound by antibodies raised against the polypeptides of the invention are also included in the definition of biologically active fragments. Such fragments are also referred to herein as "immunologically active fragments."

Biologically active fragments of the polypeptides of the invention will generally be useful where it is desired to analyze a single particular biological activity of the polypeptide. For example, therapeutic applications will generally target a single biological activity of the PI3-kinase signaling operation, e.g., substrate binding or substrate phosphorylation, and as such, peptides having fewer than all of these activities will be desired, as discussed in greater detail, below. Alternatively, such fragments may be useful where use of a full length protein is unsuitable for the particular application.

Generally, biologically active fragments of the above described proteins may include any subsequence of a full length PI 3-kinase protein of the invention. Typically, however, such fragments will be from about 5 to about 1500 amino acids in length. More typically, these peptides will be from about 10 to about 500 amino acids in length, more typically about 10 to about 250 amino acids in length, and preferably from about 15 to about 200 amino acids in length. Generally, the length of the fragment may depend, in part, upon the application for which the particular peptide is to be used. For example, for raising antibodies, the peptides may be of a shorter length, e.g., from about 5 to about 50 amino acids in length, whereas for binding or binding inhibition applications, the peptides will generally have a greater length, e.g., from about 10 to about 1000 amino acids in length, preferably, from about 15 to about 500 amino acids in length, and more preferably, from about 15 to about 200 amino acids in length.

The terms "substantially homologous" when referring to polypeptides, refer comparatively to two amino acid sequences which, when optimally aligned, are at least about 75% homologous, preferably at least about 85% homologous more preferably at least about 90% homologous, and still more preferably at least about 95% homologous. Optimal alignment of sequences for aligning a comparison window may be conducted by the local homology algorithm of Smith and Waterman (1981) Adv. Appl. Math. 2:482, by the homology alignment algorithm of Needleman and Wunsch (1970) J. Mol. Biol. 48:443, by the search for similarity method of Pearson and Lipman (1988) Proc. Natl. Acad. Sci. (USA) 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As noted above, the polypeptides of the invention may also be characterized by their ability to block the interaction between two proteins or a protein and its substrate. In particular, included in the polypeptides of the present invention are PI3-kinase derived peptides that are capable of blocking or otherwise inhibiting the interaction between cpk and/or cpk-m and their substrates, e.g., PtdIns and PtdIns4P. Examples of such polypeptides include fragments of cpk or cpk-m, which encompass the substrate binding regions of cpk and cpk-m. One example of such a fragment is the PI3-kinase domain of the cpk protein, bordered by amino acids 863–1587 of the cpk protein, and homologous regions of the cpk-m protein, as well as larger portions of the cpk and cpk-m proteins.

Also as referenced above, the polypeptides of the present invention may also be characterized by their ability to bind antibodies raised against proteins or polypeptides having the amino acid sequences of cpk and cpk-m, as shown in FIG. 1 (SEQ ID NOS:12–13), or fragments thereof. These antibodies generally recognize polypeptides that are homologous to the cpk or cpk-m proteins or their immunologically active fragments. A variety of immunoassay formats may be used to select antibodies specifically immunoreactive with a particular protein or domain. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. Antibodies to the polypeptides of the present invention are discussed in greater detail, below.

The polypeptides of the present invention may generally be prepared using recombinant or synthetic methods well known in the art. Recombinant techniques are generally described in Sambrook, et al., Molecular Cloning: A Laboratory Manual, (2nd ed.) Vols. 1–3, Cold Spring Harbor Laboratory, (1989). Techniques for the synthesis of polypeptides are generally described in Merrifield, J. Amer. Chem. Soc. 85:2149–2456 (1963), Atherton, et al., Solid Phase Peptide Synthesis: A Practical Approach, IRL Press (1989), and Merrifield, Science 232:341–347 (1986). In preferred aspects, the polypeptides of the present invention may be expressed by a suitable host cell that has been transfected with a nucleic acid of the invention, as described in greater detail below.

Biologically active fragments of the above described polypeptides may generally be identified and prepared using methods well known in the art. For example, selective proteolytic digestion, recombinant deletional methods or de novo peptide synthesis methods may be employed to identify portions of the above described peptides that possess the desired biological activity, e.g., substrate binding, catalytic activity and the like. See, e.g., Sambrook, et al.

Isolation and purification of the polypeptides of the present invention can be carried out by methods that are generally well known in the art. For example, the polypeptides may be purified using readily available chromatographic methods, e.g., ion exchange, hydrophobic interaction, HPLC or affinity chromatography, to achieve the desired purity. Affinity chromatography may be particularly attractive in allowing an individual to take advantage of the specific biological activity of the desired peptide, e.g., ligand binding, presence of antigenic determinants or the like. For example, antibodies raised against the cpk protein or immunologically active fragments may be coupled to a suitable solid support and contacted with a mixture of proteins containing the polypeptides of the invention under conditions conducive to the association of these polypeptides with the antibody. Once bound to the immobilized antibody, the solid support is washed to remove unbound material and/or nonspecifically bound proteins. The desired polypeptides may then be eluted from the solid support in substantially pure form by, e.g., a change in salt, pH or buffer concentration. Suitable solid supports for affinity purifications are well known in the art and are generally commercially available from, e.g., Pharmacia, Inc., or Sigma Chemical Co. Examples of such solid supports include agarose, cellulose, dextran, silica, polystyrene or similar solid supports.

In addition to those polypeptides and fragments described above, the present invention also provides fusion proteins which contain these polypeptides or fragments. The term "fusion protein" as used herein, generally refers to a composite protein, i.e., a single contiguous amino acid sequence, made up of two distinct, heterologous polypeptides which are not normally fused together in a single amino acid sequence. Thus, a fusion protein may include a single amino acid sequence that contains two entirely distinct amino acid sequences or two similar or identical polypeptide sequences, provided that these sequences are not normally found together in a single amino acid sequence. Fusion proteins may generally be prepared using either recombinant nucleic acid methods, i.e., as a result of transcription and translation of a gene fusion, which fusion comprises a segment encoding a polypeptide of the invention and a segment encoding a heterologous protein, or by chemical synthesis methods well known in the art.

Also included within the present invention are amino acid variants of the above described polypeptides. These variants may include insertions, deletions and substitutions with other amino acids. For example, in some aspects, conservative amino acid substitutions may be made, i.e., substitution of selected amino acids with different amino acids having similar structural characteristics, e.g., net charge, hydrophobicity and the like. Glycosylation modifications, either changed, increased amounts or decreased amounts, as well as other sequence modifications are also envisioned.

Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch (1992) Ann. Rev. Biochem. 61:387; for example, by adding internal cysteine residues capable of forming intramolecular disulfide bridges which cyclize the peptide. Similarly, modification of the amino or carboxy terminals may also be used to confer stabilizing properties upon the polypeptides of the invention, e.g., amidation of the carboxy-terminus or acylation of the amino-terminus. Substitution of amino acids involved in catalytic activity can be used to generate dominant negative inhibitors of signaling pathways.

Furthermore, although primarily described in terms of "proteins" or "polypeptides" one of skill in the art, upon reading the instant specification, will appreciate that these terms also include structural analogs and derivatives of the above-described polypeptides, e.g., polypeptides having conservative amino acid insertions, deletions or substitutions, peptidomimetics and the like. For example, in addition to the above described polypeptides which consist only of naturally-occurring amino acids, peptidomimetics of the polypeptides of the present invention are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere, J. (1986) Adv. Drug Res. 15:29; Veber and Freidinger (1985) TINS p.392; and Evans et al. (1987) J. Med. Chem 30:1229, and are usually developed with the aid of computerized molecular modeling. Peptide mimetics that are structurally similar to therapeutically useful peptides may be used to produce an equivalent therapeutic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —CH(OH)$CH_2$—, and —$CH_2SO$—, by methods known in the art and further described in the following references: Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm Sci (1980) pp. 463–468 (general review); Hudson, D. et al., Int J Pept Prot Res (1979) 14:177–185 (—$CH_2NH$—, $CH_2CH_2$—); Spatola, A. F. et al., Life Sci (1986) 38:1243–1249 (—$CH_2$—S); Hann, M. M., J. Chem Soc Perkin Trans I (1982) 307–314 (—CH—CH—, cis and trans); Almquist, R. G. et al., *J Med Chem* (1980) 23:1392–1398 (—$COCH_2$—); Jennings-White, C. et al., Tetrahedron Lett (1982) 23:2533 (—$COCH_2$—); Szelke, M. et al., European Appln. EP 45665 (1982) CA: 97:39405 (1982) (—CH(OH)$CH_2$—); Holladay, M. W. et al., Tetrahedron Lett (1983) 24:4401–4404 (—C(OH)$CH_2$—); and Hruby, V. J., Life Sci (1982) 31:189–199 (—$CH_2$—S—).

Peptide mimetics may have significant advantages over polypeptide embodiments, including, for example: more economical production; greater chemical stability; enhanced pharmacological properties (half-life, absorption, potency, efficacy, etc.); altered specificity (e.g., a broad-spectrum of biological activities); reduced antigenicity; and others.

For many applications, it may also be desirable to provide the polypeptides of the invention as labeled entities, i.e., covalently attached or linked to a detectable group, to facilitate identification, detection and quantification of the polypeptide in a given circumstance. These detectable groups may comprise a detectable protein group, e.g., an assayable enzyme or antibody epitope as described above in the discussion of fusion proteins. Alternatively, the detectable group may be selected from a variety of other detectable groups or labels, such as radiolabels (e.g., $^{125}$I, $^{32}$p or $^{35}$S) or a chemiluminescent or fluorescent group. Similarly, the detectable group may be a substrate, cofactor, inhibitor or affinity ligand. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the molecules to which the peptidomimetic binds (e.g., PtdIns) to produce the therapeutic effect. Derivitization (e.g., labeling) of peptidomimetics should not substantially interfere with the desired biological or pharmacological activity of the peptidomimetic. Generally, peptidomimetics of peptides of the invention bind to their ligands (e.g., PtdIns) with high affinity and/or possess detectable biological activity (i.e., are agonistic or antagonistic to one or more PI3-kinase mediated phenotypic changes).

IV. Nucleic Acids, Expression Vectors and Cell Lines Expressing Same

In another aspect, the present invention provides nucleic acids which encode the polypeptides of the invention, as well as expression vectors that include these nucleic acids, and cell lines and organisms that are capable of expressing these nucleic acids. These nucleic acids, expression vectors and cell lines may generally be used to produce the polypeptides of the invention. Generally, the isolated nucleic acids of the present invention encode a polypeptide which is derived from PI3-kinases that include a C2 domain within their structure. In preferred aspects, the nucleic acids of the invention encode polypeptides having PI3-kinase activity that is characterized by the capability of phosphorylating the D3 hydroxyl group on the inositol ring of PtdIns and PtdIns4P, but not PtdIns(4,5)P$_2$.

In preferred aspects, the nucleic acids of the invention encode a polypeptide having an amino acid sequence that is substantially homologous to the amino acid sequences shown in FIG. 1 (SEQ ID NOS:12–13). More preferred are those isolated nucleic acid sequences that are substantially homologous to the nucleotide sequences shown in FIGS. 9 (SEQ ID NOS:27–28) and 10 (SEQ ID NOS:29–32) or fragments thereof, and most preferred are those nucleic acid sequences having the nucleotide sequences shown in FIGS. 9 and 10.

"Nucleic acids" of the present invention include RNA, cDNA, genomic DNA, synthetic forms and mixed polymers, both sense and antisense strands. Furthermore, different alleles of each isoform are also included. The present invention also provides recombinant nucleic acids which are not otherwise naturally occurring. The nucleic acids described herein also include self replicating plasmids and infectious polymers of DNA or RNA. Unless specified otherwise, conventional notation for nucleic acids is used herein. For example, as written, the left hand end of a single stranded polynucleotide sequence is the 5'-end, whereas the right-hand end is the 3'-end. The left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The nucleic acids of the present invention may be present in whole cells, cell lysates or in partially pure or substantially pure or isolated form. When referring to nucleic acids, the terms "substantially pure" or "isolated" generally refer to the nucleic acid separated from contaminants with which it is generally associated, e.g., lipids, proteins and other nucleic acids. The substantially pure or isolated nucleic acids of the present invention will be greater than about 50% pure. Typically, these nucleic acids will be more than about 60% pure, more typically, from about 75% to about 90% pure and preferably from about 95% to about 98% pure.

The DNA compositions will generally include a coding region which encodes a polypeptide possessing PI3-kinase activity. Preferred nucleic acids will typically encode polypeptides having an amino acid sequence which is substantially homologous to the amino acid sequence shown in FIG. 1 (SEQ ID NOS:12–13), or biologically active fragments thereof. More preferred nucleic acids will comprise a segment having more than about 20 contiguous nucleotides from the nucleotide sequences shown in either of FIGS. 9 (SEQ ID NOS:27–28) or 10 (SEQ ID NOS:29–32), with still more preferred nucleic acids having a nucleotide sequence that is substantially homologous to either of the nucleotide sequences shown in FIGS. 9 (SEQ ID NOS:27–28) or 10 (SEQ ID NOS:29–32). Most preferred nucleic acids are those which include a portion or all of the nucleotide sequence shown in either of FIGS. 9 or 10.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. It being further understood that the sequence includes the degenerate codons of the native sequence or sequences which may be introduced to provide codon preference in a specific host cell.

Substantial homology in the nucleic acid context means that the segments, or their complementary strands, when compared, are the same when properly aligned, with the appropriate nucleotide insertions or deletions, in at least about 60% of the nucleotides, typically, at least about 70%, more typically, at least about 80%, usually, at least about 90%, and more usually, at least about 95% to 98% of the nucleotides. Alternatively, substantial homology exists when the segments will hybridize under selective hybridization conditions to a strand, or its complement, typically using a sequence of at least about 20 contiguous nucleotides derived from the nucleotide sequence shown in FIGS. 9 (SEQ ID NOS:27–28) or 10 (SEQ ID NOS:29–32). However, larger segments will usually be preferred, e.g., at least about 30 contiguous nucleotides, more usually about 40 contiguous nucleotides, and preferably more than about 50 contiguous nucleotides. Selective hybridization exists when hybridization occurs which is more selective than total lack of specificity. See, Kanehisa, Nucleic Acid Res. 12:203–213 (1984). Examples of such selective hybridization conditions include, e.g., hybridization under the hybridization and wash conditions of 50% formamide at 42° C. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

There are various methods of isolating the nucleic acids which encode the polypeptides of the present invention. Typically, the DNA is isolated from a genomic or cDNA library using labeled oligonucleotide probes specific for sequences in the desired DNA. Restriction endonuclease digestion of genomic DNA or cDNA containing the appropriate genes can be used to isolate the DNA encoding the polypeptides of the invention. From the nucleotide sequence given in FIG. 9 (SEQ ID NOS:27–28) or 10 (SEQ ID NOS:29–32), a panel of restriction endonucleases can be constructed to give cleavage of the DNA in desired regions, i.e., to obtain segments which encode biologically active fragments of the polypeptides of the invention. Following restriction endonuclease digestion, DNA encoding the polypeptides of the invention is identified by its ability to hybridize with a nucleic acid probe in, for example, a Southern blot format. These regions are then isolated using standard methods. See, e.g., Sambrook, et al., supra.

The polymerase chain reaction, or "PCR" can also be used to prepare nucleic acids which encode the polypeptides of the present invention. PCR technology is used to amplify nucleic acid sequences of the desired nucleic acid, e.g., the DNA which encodes the polypeptides of the invention, directly from mRNA, cDNA, or genomic or cDNA libraries. Alternatively, solid phase oligonucleotide synthesis methods may also be employed to produce the nucleic acids described herein. Such methods include the phosphoramidite method described by, e.g., Beaucage and Carruthers, Tetrahedron Lett. 22:1859–1862 (1981), or the triester method according to Matteucci, et al., J. Am. Chem. Soc., 103:3185 (1981). A double stranded fragment may then be obtained, if desired, by annealing the chemically synthesized single strands together under appropriate conditions or by synthesizing the complementary strand using DNA polymerase with an appropriate primer sequence.

Appropriate primers and probes for amplifying the nucleic acids described herein, may be generated from analysis of the nucleic acid sequences described herein, e.g., at FIG. 9 or 10. Briefly, oligonucleotide primers complementary to the two 3' borders of the DNA region to be amplified are synthesized. The PCR is then carried out using the two primers. See, e.g., PCR Protocols: A Guide to Methods and Applications (Innis, M., Gelfand, D., Sninsky, J. and White, T., eds.) Academic Press (1990). Primers can be selected to amplify a variety of different sized segments from the nucleic acid sequence.

The present invention also includes fragments of the above described nucleic acids. Such fragments will generally comprise a segment of from about 15 to about 150 nucleotides. These fragments can be useful as oligonucleotide probes in the methods of the present invention, or alternatively to encode the polypeptides or biologically active fragments of the present invention, described herein. Also provided are substantially similar nucleic acid sequences, allelic variations and natural or induced sequences of the above described nucleic acids. Also included are chemically modified and substituted nucleic acids, e.g., those which incorporate modified nucleotide bases or which incorporate a labelling group.

In one aspect, cDNA encoding the polypeptides of the present invention or fragments thereof, may be readily employed as nucleic acid probes useful for obtaining genes which encode the polypeptides of the present invention. "Nucleic acid probes" may be DNA or RNA fragments. DNA fragments can be prepared, for example, by digesting plasmid DNA, or by use of PCR, or synthesized by either the phosphoramidite or phosphotriester methods described in, e.g., Gait, oligonucleotide Synthesis: A Practical Approach, IRL Press (1990). Where a specific sequence for a nucleic acid probe is given, it is understood that the complementary strand is also identified and included. The complementary strand will work equally well in situations where the target is a double-stranded nucleic acid.

Typical nucleic acid probes may be readily derived from the nucleotide sequence shown in FIG. 9 (SEQ ID NOS:27–28) or 10 (SEQ ID NOS:29–32), or alternatively, may be prepared from the amino acid sequence of the cpk or cpk-m proteins, as shown in FIG. 1 (SEQ ID NOS:12–13). In particular, probes may be prepared based upon segments of the amino acid sequence which possess relatively low levels of degeneracy, i.e., few or one possible nucleic acid sequences which encode therefor. Suitable synthetic DNA fragments may then be prepared. Examples of such probes include, e.g., those having the following general sequences PK-1, PK-3 [PK-1: 5'GA(AGTC)GA(TC)(ATC)T(AGTC)(CA)G(AGCT)CA(AG)GA 3' (SEQ ID NO:1); PK-3: 5' CC(GA)AA(GA)TC(TGA)AT(GA)TG (TGA)A(AT)3' (SEQ ID NO:2)], PKIN-N and PKIN-C [PKIN-N:5' AA(AG)(AG)IIGGIGAIGA(CT)TI(AC)GICA(AG)GA 3' (SEQ ID NO:3); PKIN-C: T(ACG)ICC(AG)AA(AG)TCI (AG)(CT)(AG)TGIA(AT)IA 3' (SEQ ID NO:4)].

Such cDNA probes may be used in the design of oligonucleotide probes and primers for screening and cloning genes which encode the polypeptides of the invention or related polypeptides, e.g., using well known PCR techniques. These nucleic acids, or fragments may comprise part or all of the cDNA sequence that encodes the polypeptides of the present invention. Effective cDNA probes may comprise as few as 15 consecutive nucleotides in the cDNA sequence, but will often comprise longer segments. Further, these probes may further comprise an additional nucleotide sequence, such as a transcriptional primer sequence for cloning, or a detectable group for easy identification and location of complementary sequences.

cDNA or genomic libraries of various types may be screened for new alleles or related sequences using the above probes. The choice of cDNA libraries normally corresponds to tissue sources which are abundant in mRNA for the desired polypeptides. Phage libraries are normally preferred, but plasmid libraries may also be used. Clones of a library are spread onto plates, transferred to a substrate for screening, denatured, and probed for the presence of the desired sequences.

In addition to comprising a segment which encodes one or more of the above described polypeptides or biologically active fragments, the nucleic acids of the present invention may also comprise a segment encoding a heterologous protein, such that the gene is expressed to produce the two proteins as a fusion protein, as substantially described above.

Typically, the nucleic acids of the present invention will be used in expression vectors for the preparation of the polypeptides of the present invention, namely those polypeptides which possess the PI3-kinase activity described above. The phrase "expression vector" generally refers to nucleotide sequences that are capable of affecting expression of a structural gene in hosts compatible with such sequences. These expression vectors typically include at least suitable promoter sequences and optionally, transcription termination signals. Additional factors necessary or helpful in effecting expression may also be used as described herein. DNA encoding the polypeptides of the present invention will typically be incorporated into DNA constructs capable of introduction into and expression in an in vitro cell culture. Often, the nucleic acids of the present invention may be used to produce a suitable recombinant host cell. Specifically, DNA constructs will be suitable for replication in a prokaryotic host, such as bacteria, e.g., E. coli, or may be introduced into a cultured mammalian, plant, insect, yeast, fungi or other eukaryotic cell line. DNA constructs prepared for introduction into a particular host, e.g., bacteria or yeast, will typically include a replication system recognized by the host, the intended DNA segment encoding the desired polypeptide, and transcriptional and translational initiation and termination regulatory sequences operably linked to the polypeptide encoding segment. A DNA segment is operably linked when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of the polypeptide. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof. The selection of an appropriate promoter sequence will generally depend upon the host cell selected for the expression of the DNA segment. Examples of suitable promoter sequences include prokaryotic, and eukaryotic promoters well known in the art. See, e.g., Sambrook et al., Molecular Cloning: A Laboratory Manual (2d ed.), vols. 1–3 Cold Spring Harbor Laboratory (1989). The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known and available. See Sambrook et al., (1989).

Conveniently available expression vectors which include the replication system and transcriptional and translational regulatory sequences together with the insertion site for the polypeptide encoding segment may be employed. Examples of workable combinations of cell lines and expression vectors are described in Sambrook et al., and in Metzger et al., Nature 334:31–36 (1988). For example, suitable expression vectors may be expressed in, e.g., COS-7 cells, by providing constructs including the subject nucleic acids and employing, e.g., a cytomegalovirus enhancer/promoter region with the translation initiation region of the herpes simplex virus thymidine kinase gene. Alternatively, an insect cell line may be selected as the host cell of choice to express the polypeptide. In this case, the cDNA encoding the polypeptides of the invention may be cloned into a baculovirus expression vector (e.g. pV-IKS). The recombinant baculovirus may then be used to transfect a suitable insect host cell, e.g., Sf9 cells, which may then express the polypeptide. See, e.g., D. K. Morrison et al., Cell 58:649–657 (1989), M. D. Summers and G. E. Smith, A Manual of Methods for Baculovirus Vectors and Insect Cell Culture Procedures, Texas Agricultural Station, College Station, Tex. (1987).

V. Antibodies

The nucleic acids and polypeptides of the present invention or their immunologically active fragments are also useful in producing antibodies, either polyclonal or monoclonal, which are specifically immunoreactive with the polypeptides of the present invention.

The phrase "specifically immunoreactive," when referring to the interaction between an antibody of the invention and a particular protein, refers to an antibody that specifically recognizes and binds with relatively high affinity to the particular protein, such that this binding is determinative of the presence of the protein in a heterogeneous population of proteins and other biologics. Thus, under designated immunoassay conditions, the specified antibodies bind to a particular protein and do not bind in a significant amount to other proteins present in the sample. A variety of immunoassay formats may be used to select antibodies specifically immunoreactive with a particular protein. For example, solid-phase ELISA immunoassays are routinely used to select monoclonal antibodies specifically immunoreactive with a protein. See, Harlow and Lane (1988) Antibodies, A Laboratory Manual, Cold Spring Harbor Publications, New York, for a description of immunoassay formats and conditions that can be used to determine specific immunoreactivity.

For production of polyclonal antibodies, an appropriate target immune system is selected, typically a mouse or rabbit, but also including goats, sheep, cows, guinea pigs, monkeys and rats. The substantially purified antigen or plasmid is presented to the immune system in a fashion determined by methods appropriate for the animal. These and other parameters are well known to immunologists. Typically, injections are given in the footpads, intramuscularly, intradermally or intraperitoneally. The immunoglobulins produced by the host can be precipitated, isolated and purified by routine methods, including affinity purification.

For monoclonal antibodies, appropriate animals will be selected and the desired immunization protocol followed. After the appropriate period of time, the spleens of these animals are excised and individual spleen cells are fused, typically, to immortalized myeloma cells under appropriate selection conditions. Thereafter, the cells are clonally separated and the supernatants of each clone are tested for the production of an appropriate antibody specific for the desired region of the antigen. Techniques for producing antibodies are well known in the art. See, e.g., Goding et al., Monoclonal Antibodies: Principles and Practice (2d ed.) Acad. Press, N.Y., and Harlow and Lane, Antibodies: A Laboratory Manual, Cold Spring Harbor Laboratory, New York (1988). Other suitable techniques involve the in vitro exposure of lymphocytes to the antigenic polypeptides or alternatively, to selection of libraries of antibodies in phage or similar vectors. Huse et al., Generation of Large Combinatorial Library of the Immunoglobulin Repertoire in Phage Lambda, Science 246:1275–1281 (1989). Monoclonal antibodies with affinities of $10^8$ liters/mole, preferably $10^9$ to $10^{10}$ or stronger, will be produced by these methods.

The antibodies generated can be used for a number of purposes, e.g., as probes in immunoassays, for inhibiting interaction between a PI3-kinase, e.g., cpk or cpk-m, and its substrate or other ligands (thereby inhibiting or reducing the signaling cascade) in diagnostic or therapeutic applications, or in research to further elucidate the mechanism of various signaling pathways. Where the antibodies are used to block the interaction between a polypeptide of the invention and an associating molecule, e.g., protein or substrate, the antibody will generally be referred to as a "blocking antibody." The antibodies of the present invention can be used with or without modification. Frequently, the antibodies will be labeled by joining, either covalently or non-covalently, a substance which provides for a detectable signal. Such labels include those that are well known in the art, such as the labels described previously for the polypeptides of the invention. Additionally, the antibodies of the invention may be chimeric, human-like or humanized, in order to reduce their potential antigenicity, without reducing their affinity for their target. Chimeric, human-like and humanized antibodies have generally been described in the art. Generally, such chimeric, human-like or humanized antibodies comprise hypervariable regions, e.g., complementarity determining regions (CDRS) from a mammalian animal, i.e., a mouse, and a human framework region. See, e.g., Queen, et al., Proc. Nat'l Acad. Sci. USA 86:10029 (1989), Verhoeyan, et al., Science 239:1534–1536 (1988). By incorporating as little foreign sequence as possible in the hybrid antibody, the antigenicity is reduced. Preparation of these hybrid antibodies may be carried out by methods well known in the art.

Preferred antibodies are those monoclonal or polyclonal antibodies which specifically recognize and bind the polypeptides of the invention. Accordingly, these preferred antibodies will specifically recognize and bind the polypeptides which have an amino acid sequence that is substantially homologous to the amino acid sequence shown in FIG. 1, or immunologically active fragments thereof. Still more preferred are antibodies which are capable of forming an antibody-ligand complex with the polypeptides of the invention, whereby the ability of the polypeptide to associate with its substrate or normally associated proteins, in vitro, is reduced, e.g., blocking antibodies.

VI. Methods of Use

The polypeptides, antibodies and nucleic acids of the present invention may be used in a variety of important applications. Such applications include but are not limited to screening applications for identifying compounds that generally affect growth factor signal transduction pathways, also termed "signaling cascades," and therapeutic applications for the treatment of proliferative cell disorders.

A. Screening Applications

In a particular aspect, the present invention provides methods of screening test compounds to determine whether the test compounds are capable of affecting growth cell signal transduction pathways. More particularly, the methods described herein are used to screen compounds for their ability to affect the interactions between the polypeptides of the invention, and their respective substrates and ligands, as these interactions are involved in signal transduction pathways.

In one aspect, the present invention provides a screening system for determining whether a test compound is an agonist or antagonist of PI3-kinase activity. An agonist, antagonist or test compound may be a chemical compound, a mixture of chemical compounds, a biological macromolecule, or an extract made from biological materials such as bacteria, plants, fungi, or animal cells or tissues. Typically, test compounds may include structural analogs or peptidomimetics which are derived from the polypeptides or antibodies described herein, and particularly their biologically active fragments, or substrates or ligands thereof. Test compounds are evaluated for potential activity as agonists or antagonists of functions which result in signal transduction, by inclusion in screening assays described herein. An "agonist" will enhance the particular observed activity, e.g., PtdIns phosphorylation at the D3 hydroxyl, while an "antagonist" will diminish the particular observed activity. The terms "agonist" and "antagonist", as used herein, do not imply any particular mechanism of function. Particularly targeted test compounds include polypeptide fragments of the polypeptides of the present invention and structural analogs or peptidomimetics of these peptides.

The screening methods of the present invention typically involve the incubation of a polypeptide of the present invention, e.g., a cpk or cpk-m polypeptide, in the presence of PtdIns or PtdIns4P, as well as a particular test compound. The mixture is then assayed over time, to determine the amount of PtdIns 3P or PtdIns(3,4)$P_2$ produced in the presence and absence of the test compound. Where the presence of the test compound results in an increase or decrease in the amount of PtdIns 3P or PtdIns(3,4)$P_2$ produced, it will be indicative that the test compound is an agonist or antagonist of the PI3-kinase mediated signal transduction, respectively.

For determination of the amount of PtdIns3P or PtdIns(3,4)$P_2$ formed, one may employ any number of a variety of well known assay methods. For example, HPLC analysis can be readily used to quantitatively identify the above described reaction products, using, e.g., tritiated substrates, and the like. Similarly, on a more qualitative level, thin layer chromatography (TLC) can also be used to identify reaction products. The levels of the above described reaction products produced in the presence and absence of the test compound are then compared. Where the presence of the test compound results in an increase or decrease in the level of the reaction product produced by the polypeptide, it is indicative that the test compound is an agonist or antagonist of PI3-kinase activity, respectively, and more particularly, the activity of the cpk polypeptide and/or cpk-m polypeptide, as described herein.

In a related embodiment, the present invention also provides kits for carrying out the above described screening methods. The kits of the present invention generally include a polypeptide of the present invention, e.g., the cpk polypeptide, cpk-m polypeptide or a biologically active fragment thereof, as well as a substrate of the polypeptide where the catalytic activity is to be screened, e.g., PtdIns or PtdIns4P. One or more of these components may generally be provided in premeasured aliquots. The aliquots can be contained in any suitable container such as a vial or a tube. The polypeptide component can be provided in solution or in lyophilized form, and may be immobilized. The polypeptide preparation may also contain preservatives such as sodium azide or protease inhibitors such as EDTA. A carrier protein such as BSA or ovalbumin, usually between 0.5–5%, may also be included to stabilize the polypeptide. The solution form of cpk or cpk-m polypeptide may contain up to 50% glycerol if the enzyme is to be stored frozen, e.g., at −20° C. to −70° C. If the cpk or cpk-m polypeptide is provided in lyophilized form, the kit can include a reconstitution buffer to reconstitute the polypeptide, as well as a reaction buffer. Alternatively, the polypeptide can be added to the reaction buffer and the solution freeze dried. This form can be readily reconstituted in distilled water with the necessary salt components already present for the particular reaction to be screened, so that no additional reaction buffer need be supplied. Thus, depending on the form and composition of the polypeptide preparation, different buffers may be included in the kit and they may be provided in more than one aliquot. Although described in substantial detail herein, these buffers are generally optional. The appropriate substrate or ligand, depending upon the particular screening method used, may be provided in a similar fashion to that of the polypeptide component. The kits will also typically include additional reagents for carrying out the particular method, e.g., stains for detection, antibodies, solid supports and the like, as well as detailed operating specifications for their use. For example, where binding interactions are being screened, the ligand component may generally be supplied within the kit, already coupled to an appropriate support.

Once identified, particular agonists or antagonists may then be used to enhance or block the activity of the polypeptides of the present invention. This may be particularly useful in therapeutic applications (see discussion, below).

B. Therapeutic Applications

In addition to the above described uses, the polypeptides, nucleic acids and antibodies of the present invention may also be used in therapeutic applications for the treatment of human or non-human mammalian patients. The term "treatment" as used herein, refers to the full spectrum of treatments for a given disorder from which the patient is suffering, including alleviation of one, most or all symptoms resulting from that disorder, outright cure for the particular disorder and prevention of the onset of the disorder.

As described previously herein, the polypeptides of the present invention have been implicated as providing a critical step in cell signal transduction, e.g., involved in the growth factor activation cascades. One such growth factor activation cascade leads to the activation of the Ras oncagene, which has been associated with a variety of proliferative disorders including atherosclerosis, inflammatory joint diseases, psoriasis, restenosis following angioplasty, and cancer. See, e.g., G. Pelicci et al. *Cell* 70, 93–104 (1992); M. Rozakis-Adcock et al. *Nature,* 360:689 (1992), Hu et al., Science 268:100–102 (1995).

Accordingly, treatment of the above described disorders may generally be carried out by blocking or inhibiting activation of Ras. This may be accomplished by blocking or inhibiting one or more of the activities responsible for signal transduction leading to activation of Ras, including, e.g., the phosphoryation of the D3 hydroxyl of PtdIns and PtdIns4P, which compounds are involved in the signal transduction pathway which activates Ras.

Generally, inhibition of the particular activity may be carried out by providing a polypeptide of the invention which will compete with the endogenous PI3-kinases. For example, by administering to a patient an effective amount of a substrate binding portion of a polypeptide of the invention, as described herein, one may block association of endogenous PI3-kinases with their substrates, and thereby reduce the level of Ras activation. Similar strategies may be employed using blocking antibodies of the present invention, i.e., those antibodies capable of inhibiting the interaction between the polypeptides of the invention and their substrates or other ligands.

The quantities of reagents necessary for effective therapy, also referred to herein as an "effective amount," or "therapeutically effective amount," will depend upon many different factors, including means of administration, target site, physiological state of the patient and other medicants administered. Thus, treatment doses will need to be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Generally, therapeutically effective amounts of the GA5Ptase containing polypeptides of the present invention will be from about 0.0001 to about 10 mg/kg, and more usually, from about 0.001 to about 0.1 mg/kg of the host's body weight. Various considerations are described, e.g., in Gilman et al., (Eds.), *Goodman and Gilman's: The Pharmacological Basis of Therapeutics*, (8th ed. 1990), Pergamon Press, and *Remington's Pharmaceutical Sciences* (7th ed. 1985) Mack Publishing Co., Easton, Penn. Methods of administration, also discussed in the above references, include, e.g., oral, intravenous, intraperitoneal or intramuscular administration, and local administration, including topical, transdermal diffusion and aerosol administration, for therapeutic, and/or prophylactic treatment. The active agent, i.e., the polypeptide component, will generally be administered in a composition additionally comprising a pharmaceutically acceptable carrier. Suitable pharmaceutically acceptable carriers include water, saline, buffers and other compounds described in, e.g., the Merck Index, Merck and Co., Rahway, N.J. For some methods of administration, e.g., oral, it may be desirable to provide the active ingredient in a liposomal formulation. This is particularly desirable where the active ingredient may be subject to degradative environments, for example, proteolytic digestive enzymes. Liposomal formulations are well known in the art, and are discussed in, e.g., Remington's Pharmaceutical Sciences, supra. Administration may also be carried out by way of a controlled release composition or device, whereby a slow release of the active ingredient allows continuous administration over a longer period of time.

Constituents of pharmaceutical compositions, in addition to the active agents described herein, include those generally known in the art for the various administration methods used. For example, oral forms generally include powders, tablets, pills, capsules, lozenges and liquids. Similarly, intravenous, intraperitoneal or intramuscular formulations will generally be dissolved or suspended in a pharmaceutically acceptable carrier, e.g., water, buffered water, saline and the like. Additionally, these compositions may include additional constituents which may be required to approximate physiological conditions, such as pH adjusting and buffering agents, tonicity adjusting agents, wetting agents and the like. For solid compositions, conventional nontoxic solid carriers may be used which include, e.g., pharmaceutical grades of mannitol, lactose, starch, magnesium stearate, sodium saccharin, talcum, cellulose, glucose, sucrose, magnesium carbonate and the like.

Administration may also be carried out by way of a controlled release composition or device, whereby a slow release of the active ingredient allows continuous administration over a longer period of time.

Additionally, as PI3-kinases play critical roles in cell signaling pathways, the present invention may also provide an exogenous regulatory mechanism in the treatment of disorders where these regulatory mechanisms are disfunctional. In particular, the treatment of a particular disorder may comprise gene therapy techniques involving the mutation, dysregulation or augmentation of levels of exogenous PI3-kinase. For example, gene therapy techniques may involve the introduction into afflicted cells, of genes which encode a protein or polypeptide which possesses the PI3-kinase activity. These exogenously introduced genes' products may then augment existing levels of this activity in cells that may be otherwise deficient.

Strategies for gene therapy are reviewed in Friedmann, *Science* 244:1275 (9189). Genetic constructs encoding the cpk, cpk-m or functional derivatives, can be used in these gene therapy techniques. Delivery of the genetic construct of interest, i.e., the nucleic acid encoding a PI3-kinase protein or fragment, may be accomplished in vivo by administering the therapy vector to an individual patient, typically by systemic administration (e.g., intravenous, intraperitoneal, intramuscular, subdermal, or intracranial administration). Alternatively, the vector may be used to deliver nucleic acids to cells ex vivo, such as cells explanted from an individual patient or universal donor hematopoietic stem cells, neurons, etc, e.g., by transfection of the cells with nucleic acids of interest cloned into retroviruses. Following transfection, the cells are reimplanted into the patient, usually after selection for cells which have incorporated the nucleic acid. The infusion into the patient of transfected cells can replace cells which are dysfunctional for the particular regulatory scheme which results in the disorder being treated.

The present invention is further illustrated by the following examples. These examples are merely to illustrate aspects of the present invention and are not intended as limitations of this invention.

VII. EXAMPLES

Example 1

Identification of the Drosophila and Murine cpk Genes.

The cpk and cpk-m genes were obtained by PCR amplification of Drosophila and murine cDNA libraries with the degenerate primers PK-1 and PK-3 [PK-1: 5'GA(AGTC)GA(TC)(ATC)T(AGTC)(CA)G(AGCT)CA(AG)GA 3' (SEQ ID NO:1); PK-3: 5' CC(GA)AA(GA)TC(TGA)AT(GA)TG(TGA)A(AT) 3' (SEQ ID NO:2)] for Drosophila. These primers correspond to two regions of conserved amino acids in PtdIns kinase domains, (DE)D(LI)RQD (SEQ ID NO:5) and (FI)HIDFG (SEQ ID NO:6). The murine cpk-m gene was amplified using primers PKIN-N and PKIN-C [PKIN-N:5' AA(AG)(AG)IIGGIGAIGA(CT)TI(AC)GICA(AG)GA 3' (SEQ ID NO:3); PKIN-C: T(ACG)ICC(AG)AA(AG)TCI(AG)(CT)(AG)TGIA(AT)IA 3' (SEQ ID NO:4)]. PCR products of approximately 400 base pairs were recovered and sequencing revealed open reading frames with sequence identity to p110 PtdIns 3-kinases. These DNA fragments were then used as probes to screen cDNA libraries. Large cDNAs, which did not contain the 5' ends of the cpk cDNAs, were recovered from the Drosophila and murine libraries. The 5' ends of the cDNAs were extended using a 5' RACE kit (Gibco BRL). Construction of the Drosophila cDNA library from 4–8 hr Drosophila embryos was previously described in Brown et al., J. Mol. Biol. 203:425–437 (1988). The murine cDNA libraries used were random and oligo(dT) primed mouse brain and mouse liver libraries purchased from Clontech. Standard procedures were used for cloning. The sequence of DNA was determined using an A.L.F. DNA Sequencer (Pharmacia). The size of the cDNA (6.9 kb) is consistent with the size of the mRNA as estimated by northern blot analysis. Conceptual translation of the cDNA revealed a large open reading frame (ORF) encoding a protein with a predicted molecular weight of 210 Kd. The first methionine in this ORF is encoded by the first ATG in the cDNA and it is preceded by an in frame stop codon. The Drosophila and murine cpk proteins are 34% identical and 48% similar (FIG. 1) (SEQ ID NOS:12–13).

Example 2

Generation of α-cpk Polyclonal Sera

A fragment of the Drosophila cpk protein was expressed in the E. coli strain BL21DE3(lysS) as a hexahistidine fusion protein. The Drosophila cpk cDNA was digested with NcoI (cleaving at position 1892) and HpaI (at position 4157) and the resulting 2265 base pair fragment (corresponding to the fragment encoding amino acids 563–1317) was ligated into the NcoI and Ecl136II sites of pet23d (Novagen). This construct drives expression of an 85 Kd cpk hexahistidine fusion protein, named pet.1. This protein was found to reside completely in inclusion bodies. Accordingly, the inclusion bodies were purified, solubilized in 1× Laemmli sample buffer, and electrophoresed on a 8% preparative gel. The pet.1 polypeptide was eluted from a gel slice and then used to immunize rabbits (Berkeley Antibody Company). The resulting polyclonal serum, designated α-cpk, was purified on an affinity column. The affinity column was prepared by coupling two milligrams of pet.1 protein to an affigel 10 solid support, according to the manufacturer's instructions (Biorad). This antigen column was used to immunoaffinity purify α-cpk serum. The affinity purified serum was then incubated with whole cell BL21DE3(lysS) lysates that had been immobilized to a PVDF membrane (Millipore). In this manner, antibodies to E. coli proteins that coelute with pet.1 from the gel slice were eliminated. Preimmune serum was similarly treated, for use as a control.

In order to produce an independent serum that recognizes cpk protein, polyclonal α-peptide serum was also generated by immunizing rabbits with the P6 peptide (NH$_2$—CRQDFLSQPSTSSSQY—COOH) (SEQ ID NO:7), which corresponds to amino acids 419–434 of the cpk protein. The P6 peptide was conjugated to the carrier and then used to immunize rabbits (Berkeley Antibody Company).

Figures 3A, 3B:
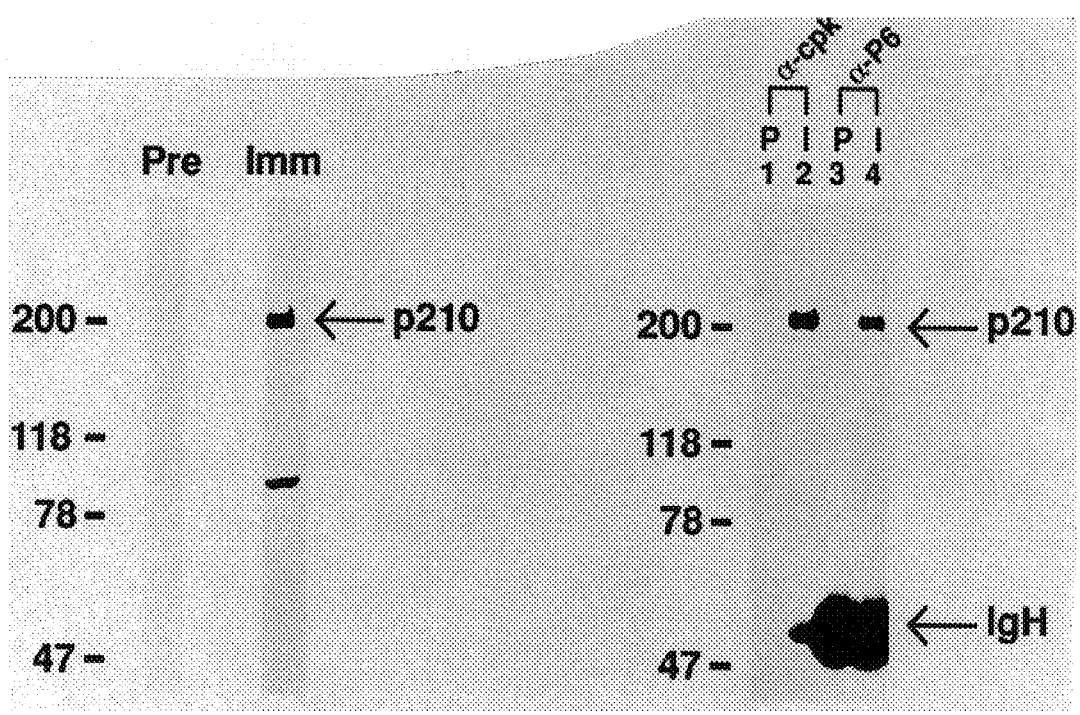
FIGS. 3A and 3B illustrate the detection of cpk protein in lysates prepared from Drosophila embryos.

The resulting α P-6 serum, which was designated α-P6, was used to precipitate protein from Drosophila lysates. The precipitates were resolved by SDS-PAGE, transferred to a PVDF membrane and probed with α-cpk serum (FIG. 3B). Both the α-cpk and α-P6 immune sera precipitated a 210 Kd polypeptide that was recognized by α-cpk serum. p210 was not detected in control precipitates using preimmune sera. Half of each precipitate (e.g., α-cpk and α-P6 precipitates) was assayed for PtdIns kinase activity and the other half was used for the detection of cpk protein on a immunoblot. PtdIns kinase activity was detected in precipitates using the α-cpk and α-P6 immune sera, but not in precipitates using preimmune sera. The PtdIns kinase activity was competed by preincubating the α-cpk serum with the cpk fusion protein or the α-P6 serum with the P6 peptide. Therefore, cpk protein precipitated from Drosophila lysates has a PtdIns kinase activity.

Polyclonal α-peptide serum against murine cpk-m was generated by immunizing rabbits with the NB-70 peptide (NH$_2$—CQGQVSQKDPNGTSS—COOH) (SEQ ID NO:8). This peptide was conjugated with KLH carrier protein before immunizing rabbits (Caltag). The resulting serum, which was designated 4863, was used to precipitate and probe protein from fibroblast cell lysates. A polypeptide with a molecular weight of approximately 210 kDa in the crude cell lysates and precipitates was recognized by the immune serum but not by the preimmune serum. PtdIns kinase activity was detected in precipitates using 4863 immune serum, but not in precipitates obtained using pre-immune serum. Both the PtdIns kinase activity and the 210 kDa protein band on a Western blot were competed bypre-incubating the 4683 serum with the NB-70 peptide.

Figure 5A:
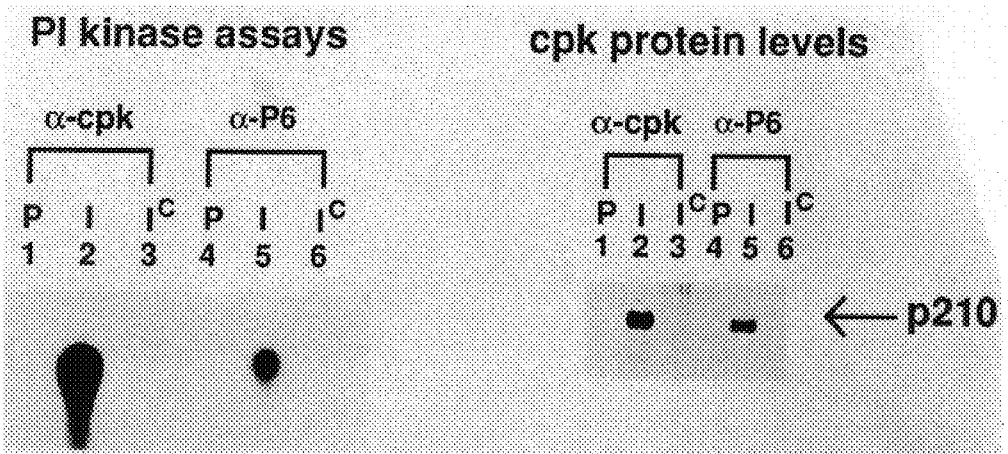
FIGS. 5A and 5B show the precipitation of proteins from Drosophila lysates using α-cpk serum and α-P6 serum.
Figure 5B:
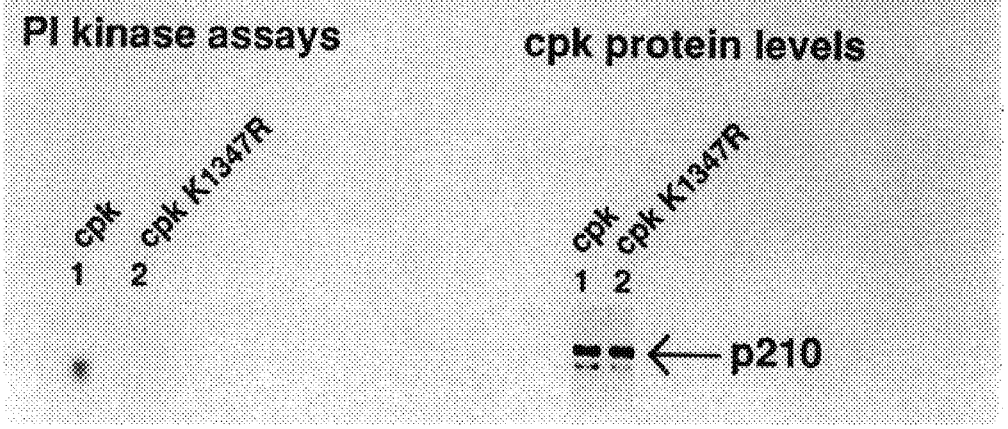

In order to eliminate the possibility that the activity detected in the α-cpk and α-P6 precipitates resulted from a PtdIns kinase coprecipitating with cpk, rather than from cpk protein itself, it was independently determined that cpk can phosphorylate PtdIns. This was accomplished by assaying the activity of cpk protein obtained by exogenous expression in COS-7 cells (FIG. 5B). Wild-type and kinase deficient cpk proteins were tagged with an HA epitope and then expressed in COS-7 cells. A kinase deficient cpk mutant was constructed by changing a conserved lysine in the catalytic domain to arginine. Wild type and mutant cpk proteins were precipitated from COS-7 cell lysates. One half of each precipitate was assayed for PtdIns kinase activity and the other half was used for the detection of cpk protein on an immunoblot. Precipitates containing wild-type cpk protein contained a PtdIns kinase activity, while precipitates containing an equivalent amount of the mutant cpk protein did not (FIG. 5B). These data indicate that cpk protein possesses intrinsic PtdIns kinase activity.

Example 3

Preparation of Drosophila Lysates and Immunochemical Assays

Lysates were prepared by dounce homogenizing 0–12 hr Drosophila embryos in lysis buffer (20 mM N-2-hydroxyethyl piperazine-N'-2-ethanesulfonic acid (HEPES) pH 7.5, 150 mM sodium chloride, 2 mM EDTA 10 mM sodium fluoride, 10 mM sodium phosphate (pH 7.5), 10 mM tetrasodium pyrophosphate, 10 mM sodium orthovanadate, 2 mM phenylmethylsulfonyl fluoride, 10% glycerol, 10 trypsin inhibiting units/ml aprotinin, and 20 $\mu$M leupeptin). The lysates were then frozen in aliquots at $-70°$ C. Immediately prior to use, an aliquot was thawed, diluted with lysis buffer containing 1% Triton X-100, and the insoluble proteins were pelleted in a microfuge. cpk protein was detected by immunoblotting in the following manner: proteins from lysates were resolved by SDS-PAGE on a 6% gel and then transferred to a PVDF membrane (Millipore) using high molecular weight transfer buffer; the blots were incubated with the appropriate serum diluted in TBS-T (TBS-T: 50 mM Tris pH 8.0; 150 mM sodium chloride, and 0.1% Tween-20) containing 5% dry milk and 1% ovalbumin; and then processed using an enhanced chemiluminescence kit (Amersham).

Figure 4:
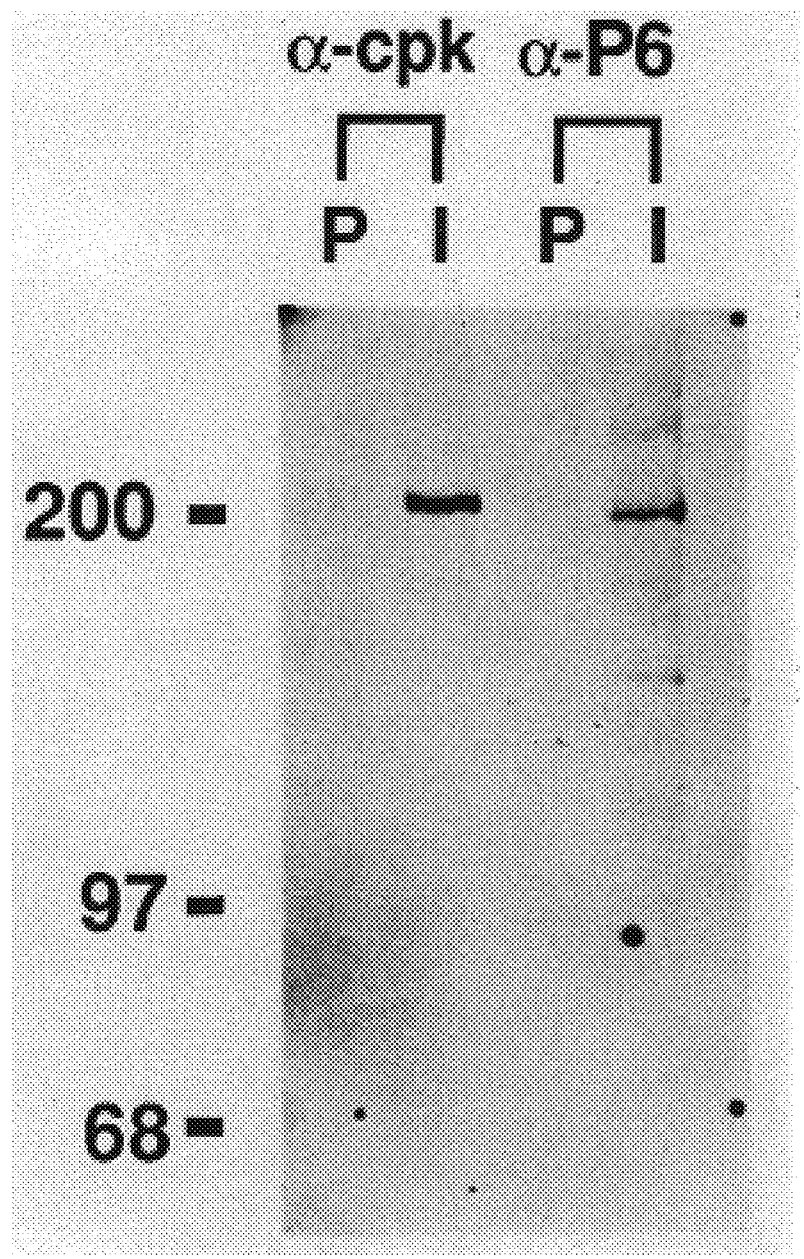
FIG. 4 shows an immunoblot of cpk protein immunoprecipitated from Drosophila lysates and probed with α-phosphotyrosine. Drosophila lysates were precipitated using α-cpk preimmune (lane 1), α-cpk immune (lane 2), α-P6 preimmune (lane 3) or α-P6 immune sera (lane 4).

To determine if the cpk protein is a substrate of a tyrosine kinase, e.g., tyrosine phosphorylated, similar blots were probed with an $\alpha$-phosphotyrosine antibody (FIG. 4). The cpk precipitations contained an $\alpha$-phosphotyrosine reactive polypeptide migrating at 210 Kd, the molecular weight of the cpk protein.

Example 4

PtdIns Kinase Assays cpk protein was precipitated from either COS-7 cell or Drosophila lysates as described in Harlow et al., Antibodies: A Laboratory Manual (Cold Spring Harbor Laboratory Press, Cold Spring Harbor, N.Y. (1988)). The precipitations were washed four times in lysis buffer containing 1.0% Triton X-100 and then two times in PtdIns kinase assay buffer (PtdIns kinase assay buffer: 30 mM HEPES pH 7.5, 30 mM magnesium chloride). PtdIns kinase assays in which PtdIns was used as the substrate were performed as previously described in Kaplan et al., Cell 50:1021–1029 (1987) and Whitman et al., Nature 322:644–646 (1988). The PtdIns kinase assays were modified in the following manner for the determination of PtdIns, PtdIns4P and PtdIns(4,5)P$_2$ substrate specificities. The PtdIns, PtdIns4P, and PtdIns(4,5)P$_2$ lipid substrates were mixed with an equal amount of phosphatidylserine (PS) and then sonicated to form vesicles. Preparation of vesicles with PS assures that the physical properties of the PtdIns, PtdIns4P, and PtdIns(4,5)P$_2$ vesicles are approximately equivalent. The products of these kinase assays were resolved by TLC (Thin Layer Chromatography) using silica gel 60 plates (Whatman) in a buffer consisting of chloroform:acetone:methanol:acetic acid:water (80:30:26:24:14). cpk Kinase assays were further modified by the addition of 0.05% 3-[(3-cholamidopropyl) dimethylammonio]-1-propanesulfonate (CHAPS) to the vesicle substrates and to the PtdIns kinase assay buffer. The addition of CHAPS was determined to stimulate cpk PtdIns kinase activity in vitro.

Example 5

Determination of the Position on the Inositol Ring Phosphorylated by cpk

Since the cpk proteins are related to PtdIns kinases, it was of interest to determine whether they could phosphorylate PtdIns, and whether this phosphorylation occurred on the D3 or D4 position of the inositol ring.

Figures 6A, 6B:
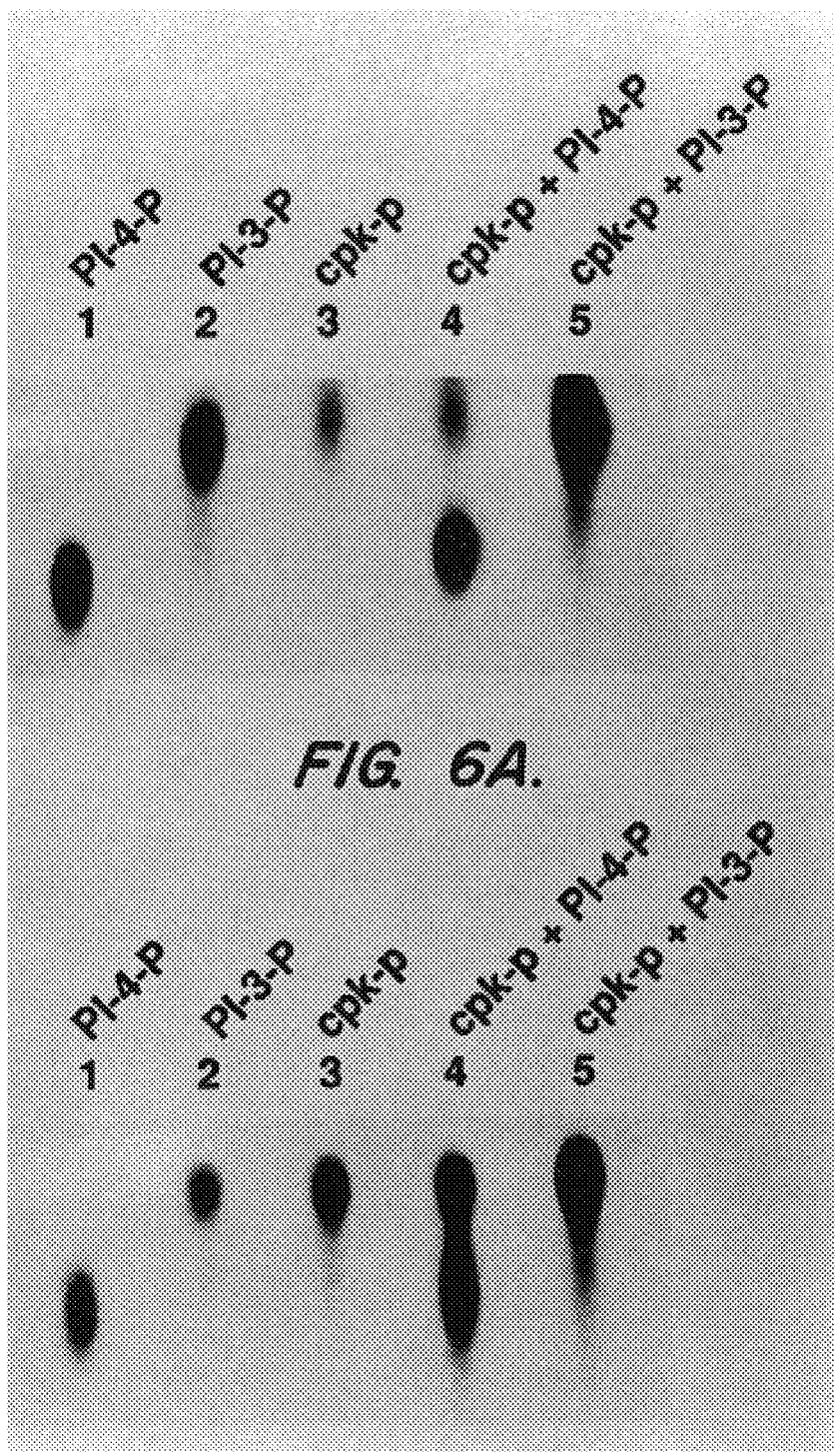
FIGS. 6A and 6B show the results of thin layer chromatography of the products of cpk protein activity on PtdIns substrate. The cpk was precipitated from Drosophila (FIG. 6A) and COS-7 cells (FIG. 6B) using α-cpk or α-HA serum, respectively. The cpk reaction products (lane 3) migrated at approximately the same position as a $[\gamma^{32}P]$-PtdIns3P standard (lane 2), but not a $[\gamma^{32}P]$-PtdIns4P standard (lane 1). Cpk reaction products were also mixed with either $[\gamma^{32}P]$-PtdIns3P (lane 5) or $[\gamma^{32}P]$-PtdIns4P (lane 4) standards and the mixtures were separated. The cpk reaction products comigrated with $[\gamma^{32}P]$-PtdIns3P (lane 5). The cpk reaction products are designated by cpk-p.

PtdIns3P and PtdIns4P were resolved using TLC with a borate buffer system that has previously been described in detail in Walsh et al., Proc. Nat'l Acad. Sci. USA 88:9184–9187 (1991). [$\gamma^{32}$P]-PtdIns3P and [$\gamma^{32}$P]-PtdIns4P standards were generated in the following manner. PtdIns3-$\gamma^{32}$P was produced by phosphorylating PtdIns with [$\gamma^{32}$P]-ATP using a constitutively active p110 mutant protein (p110*) whose construction and expression was previously described in Hu et al., Science 268:100–102 (1995). PtdIns4-$\gamma^{32}$P was produced by phosphorylating PtdIns with [$\gamma^{32}$P]-ATP with lysates (20 $\mu$g) prepared from 0–12 hr Drosophila embryos. PtdIns 4-kinases are generally the most abundant PtdIns kinases found in lysates. In order to verify that the major product of this reaction is indeed PtdIns4P, the reaction products were demonstrated to comigrate with an unlabeled PtdIns4P standard (Sigma), but could be resolved from the PtdIns3-$\gamma^{32}$P standard. The unlabeled PtdIns4P standard was visualized by iodine staining. Cpk protein was precipitated from either Drosophila lysates (FIG. 6A) or COS-7 cell lysates (FIG. 6B) and used to phosphorylate PtdIns. The [$\gamma^{32}$P] labeled products of these reactions were separated by TLC. The cpk products migrated at the position of a [$\gamma^{32}$P] labeled PtdIns3P standard, but not a PtdIns4P standard. The cpk products were then mixed with either PtdIns3P or PtdIns4P standards and the mixtures were resolved by TLC. The lipid products of cpk comigrated with the PtdIns3P standard, but not with the PtdIns4P standard, suggesting that the cpk reaction products are PtdIns3P and that cpk is a PtdIns 3-kinase.

Figure 7:
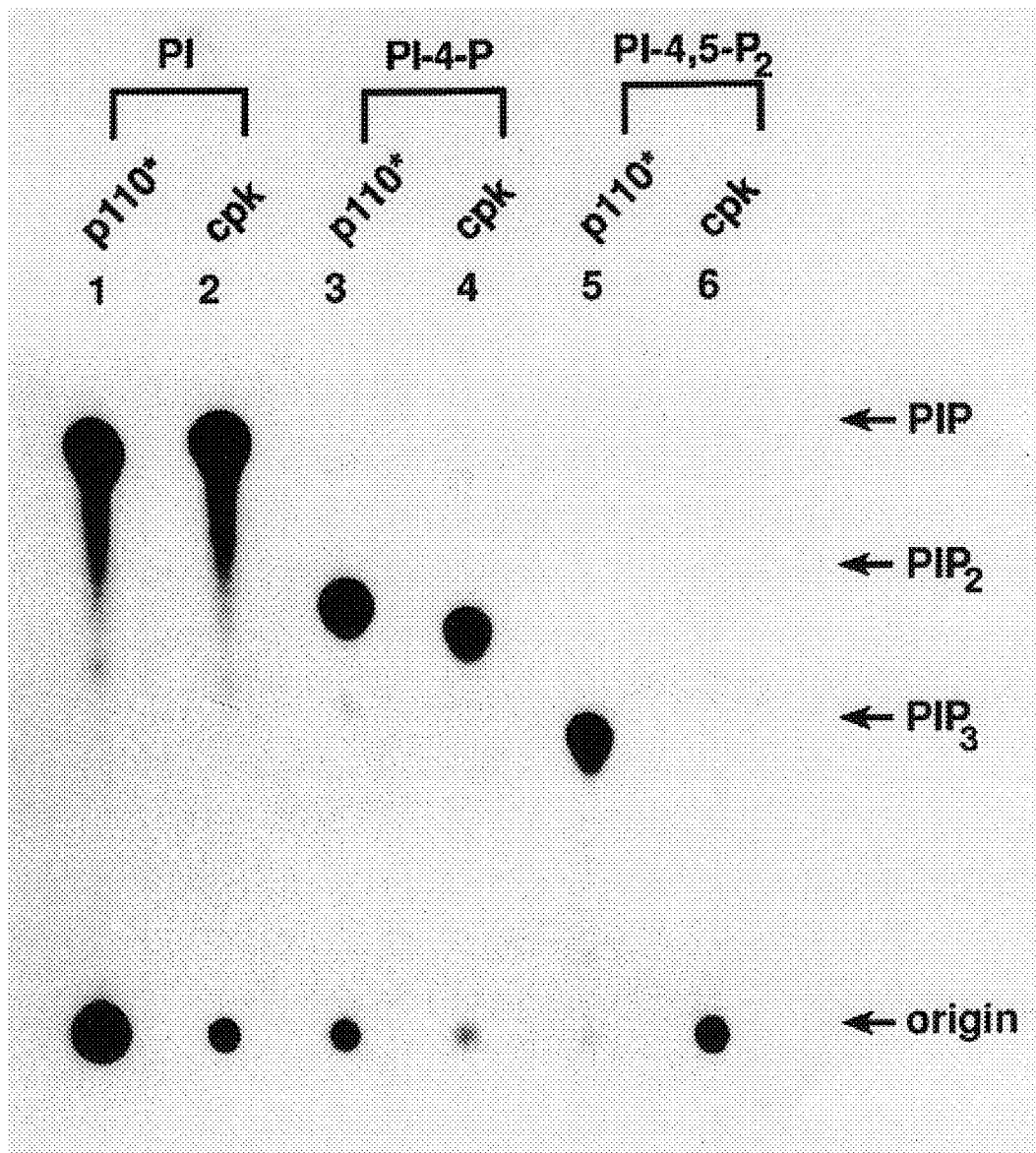
FIG. 7 is a thin layer chromatograph showing phosphorylation of either PtdIns (lane 2), PtdIns4P (lane 4) or PtdIns(4,5)P$_2$ (lane 6) using cpk protein precipitated from Drosophila embryo lysates. A consitutively active p110 protein (p110*) capable of phosphorylating PtdIns (lane 1), PtdIns4P (lane 3) and PtdIns(4,5)P$_2$ (lane 5) substrates was used as a control. PIP, PIP$_2$ and PIP$_3$ refer to phosphatidylinositol phosphate, phosphatidylinositol bisphosphate, and phosphatidylinositol trisphosphate, respectively.

PtdIns 3-kinases have distinct substrate specificities in vitro. For example, Vps34 can only phosphorylate PtdIns, while p110/p85 can phosphorylate PtdIns, PtdIns4P, and PtdIns(4,5)P$_2$. Using in vitro kinase assays, cpk was also determined to have a unique substrate specificity, being capable of phosphorylating PtdIns and PtdIns4P, but not PtdIns(4,5)P$_2$ (FIG. 7). A constitutively active p110(p110*, Hu et al., Science 268:100–102 (1995)) was used as a control and it phosphorylated PtdIns, PtdIns4P, and PtdIns (4,5)P$_2$. It has also been determined that wild-type cpk protein obtained from exogenous expression in COS-7 cells displayed the same substrate specificity as protein derived from Drosophila lysates. A kinase deficient cpk protein obtained from exogenous expression in COS-7 cells served as a control and was unable to phosphorylate any of these substrates.

Example 6

Expression of Proteins in COS-7 Cells

A plasmid was constructed that expressed cpk-HA fusion proteins in COS-7 cells. NotI and SmaI sites were introduced into the cpk cDNA at the position of the stop condon using the primer dPIK 34 (dPIK 34: 5' CCCCGGGTCAG CGGC-CGCCGTTCCTGGACACCGCGCCCAG 3') (SEQ ID NO:10), which corresponds to nucleotides 5755–5795 of the cDNA. A triple tandem copy of HA1 epitope on a NotI DNA fragment was ligated into the NotI site. An SpeI site was introduced at the position of the initiating methionine using the primer dPIK 29 (dPIK29: 5' TTAGACGAGACTAG-TATGTCAAATCAAGCG 3'), which corresponds to nucleotides 132–162 of the cpk cDNA. The resulting 5683 base pair SpeI/SmaI fragment was ligated into the XbaI/SmaI sites of the mammalian expression vector pCG. pCG is a derivative of pEVRF with a modified polylinker that contains the human cytomegalovirus enhancer/promoter region and the translation initiation region of the herpes simplex virus thymidine kinase gene. A kinase deficient cpk protein was constructed by changing lysine 1347 to arginine with the primer dPIK 27 (dPIK27: 5' GTGGGACCTGATGC-CGAATCTTTACCGGCTATCTTTAGGTGCGGA 3') (SEQ ID NO:11. A constitutively active p110 mutant protein (p110*) was expressed as a control.

Example 7

Drug Sensitivity of cpk

Drug sensitivity and divalent cation requirement were determined for the cpk PtdIns kinase activity relative to p110. P110 PtdIns 3-kinase activity is sensitive to wortmannin, a fungal metabolite that has been shown to be a selective inhibitor of PtdIns kinases. In vitro, the wortmannin sensitivity of the cpk PI3-kinase activity is similar to that of p110. The IC-50 (half maximal inhibition) value for p110 was determined to be 7.5 nM, which is a value consistent with previous studies (Woscholski et al., FEBS Lett. 342:109–114 (1994)). The IC-50 for wortmannin inhibition of cpk was 11 nM. Also, p110 requires the addition of either $Mg^{2+}$ or $Mn^{2+}$ to in vitro kinase assays, although the enzyme is more active in the presence of $Mg^{2+}$ (Volinia et al., EMBO J. 14:3339–3348 (1995)). In contrast, cpk strictly requires the presence of $Mg^{2+}$ in in vitro kinase assays, and the enzyme is inactive in the presence of $Mn^{2+}$.

Example 8

Identification of cpk Binding Proteins

Figures 8A, 8B, 8C:
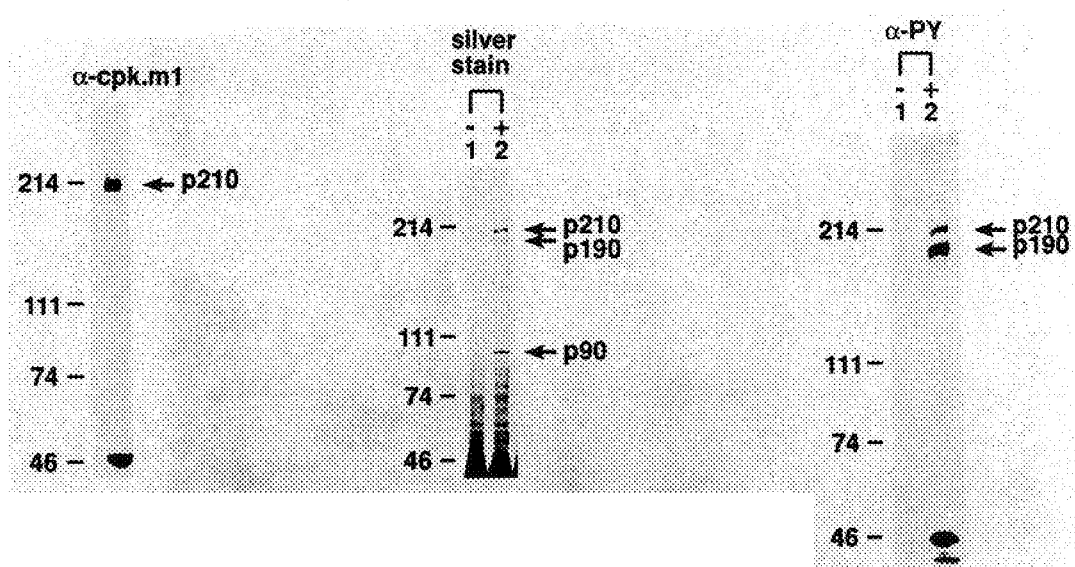
FIGS. 8A, 8B and 8C show the coprecipitation of two protein components with cpk, from Drosophila lysates.

Monoclonal antibody serum was generated which specifically recognizes cpk (α-cpk.m1), for the purpose of identifying cpk binding proteins. The serum recognizes cpk on an immunoblot of lysates prepared from 0–12 hr Drosophila embryos (FIG. 8A). cpk protein was precipitated from Drosophila lysates using α-cpk.m1 and the precipitates were resolved by SDS-PAGE. The proteins were visualized by silver staining (FIG. 8B). In addition to cpk, two other proteins were observed having approximate molecular weights of 90 Kd and 190 Kd (p90 and p190, respectively). These proteins were not recognized by α-cpk.m1 serum on an immunoblot, indicating that these fragments are not related to cpk. This also indicates that these proteins are not independently precipitated by the serum. Blots of cpk precipitates containing cpk, p90 and p190 were probed with α-phosphotyrosine to determine whether these proteins were tyrosine phosphorylated. Proteins migrating at approximately 190 Kd and 210 Kd reacted with the antiphosphotyrosine antibody, indicating tyrosine phosphorylation, and probable regulation by tyrosine kinases (See also FIG. 4).

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. An isolated nucleic acid segment that encodes an amino acid sequence, which amino acid sequence is at least 90% identical to the amino acid sequence of SEQ ID NOs:28 or 30, wherein said nucleic acid segment encodes a polypeptide having phosphatidylinositol 3-kinase (PI3-kinase) activity, whereby said polypeptide phosphorylates the D3 hydroxyl of the inositol ring one or more of the following: phosphatidylinositol and phosphatidylinositol 4-phosphate; but said polypeptide does not phosphorylate the inositol ring of phosphatidylinositol 4,5-bisphosphate.

2. The isolated nucleic acid segment according to claim 1, wherein said amino acid sequence is SEQ ID NOs: 28 or 30.

3. The isolated nucleic acid segment according to claim 1 that is SEQ ID NOs: 27 or 29.

4. The isolated nucleic acid segment according to claim 1, wherein said nucleic acid segment further comprises an additional nucleic acid sequence which encodes a heterologous protein, whereby the expression product of the nucleic acid segment is a fusion protein.

5. An expression vector comprising the nucleic acid segment according to claim 1 or claim 4 operably linked to a promoter sequence.

6. A recombinant host cell, wherein said host cell has been transformed or transfected with an expression vector according to claim 5.

7. The recombinant host cell of claim 6, wherein said host cell is selected from the group consisting of bacterial, mammalian, plant, fungal, and insect cells.

8. The recombinant host cell of claim 7, wherein said host cell is a COS-7 cell.

9. A method for producing a polypeptide comprising:

(a) culturing a host cell, wherein said host cell is according to claim 6, under conditions wherein the polypeptide encoded by the nucleic acid segment contained on the vector is expressed, and (b) recovering said polypeptide from the cultured host cell or its culture medium.

* * * * *